US012616674B2

(12) United States Patent
Gomer et al.

(10) Patent No.: US 12,616,674 B2
(45) Date of Patent: May 5, 2026

(54) ANTI-FIBROTIC NEU3 INHIBITOR COMPOUNDS AND METHODS OF USE

(71) Applicant: The Texas A&M University System, College Station, TX (US)

(72) Inventors: Richard H. Gomer, College Station, TX (US); Thomas Meek, College Station, TX (US); Tejas Karhadkar, College Station, TX (US); Darrell Pilling, Cypress, TX (US)

(73) Assignee: The Texas A&M University System, College Station, TX (US)

( * ) Notice: Subject to any disclaimer, the term of this patent is extended or adjusted under 35 U.S.C. 154(b) by 960 days.

(21) Appl. No.: 17/430,287

(22) PCT Filed: Feb. 10, 2020

(86) PCT No.: PCT/US2020/017504
§ 371 (c)(1),
(2) Date: Aug. 11, 2021

(87) PCT Pub. No.: WO2020/167663
PCT Pub. Date: Aug. 20, 2020

(65) Prior Publication Data

US 2022/0133671 A1 May 5, 2022

Related U.S. Application Data

(60) Provisional application No. 62/804,262, filed on Feb. 12, 2019.

(51) Int. Cl.

| | |
|---|---|
| ***A61K 31/215*** | (2006.01) |
| ***A61K 31/351*** | (2006.01) |
| ***A61K 31/401*** | (2006.01) |
| ***A61K 31/4402*** | (2006.01) |
| ***A61K 31/4406*** | (2006.01) |
| ***A61K 31/4422*** | (2006.01) |
| ***A61K 31/445*** | (2006.01) |
| ***A61K 31/455*** | (2006.01) |
| ***A61K 31/55*** | (2006.01) |
| ***A61K 31/60*** | (2006.01) |
| ***A61P 35/00*** | (2006.01) |

(52) U.S. Cl.
CPC .......... *A61K 31/215* (2013.01); *A61K 31/351* (2013.01); *A61K 31/401* (2013.01); *A61K 31/4402* (2013.01); *A61K 31/4406* (2013.01); *A61K 31/4422* (2013.01); *A61K 31/445* (2013.01); *A61K 31/455* (2013.01); *A61K 31/55* (2013.01); *A61K 31/60* (2013.01); *A61P 35/00* (2018.01)

(58) Field of Classification Search
CPC . A61K 31/4402; A61K 31/215; A61K 31/445
See application file for complete search history.

(56) References Cited

U.S. PATENT DOCUMENTS 9,447,078 B2 9/2016 Kuksa et al.

FOREIGN PATENT DOCUMENTS

| | | |
|---|---|---|
| JP | 2015030715 | 2/2015 |
| WO | 2002/020486 | 3/2002 |
| WO | 2015/185977 | 12/2015 |
| WO | 2018049003 | 3/2018 |

OTHER PUBLICATIONS

PubChem, "PubChem Compound Summary for CID 241, Benzene", first available 2004, National Library of Medicine (Year: 2004).*

Arauz et al., "Nicotinic acid prevents experimental liver fibrosis by attenuating the prooxidant process", 2015, International Immunopharmacology, 28, pp. 244-251 (Year: 2015).*

PubChem, "Nicotinic acid", first available 2004, National Library of Medicine, p. 1-3 (Year: 2004).*

Karhadkar et al., "Sialidase inhibitors attenuate pulmonary fibrosis in a mouse model", 2017, Scientific Reports, 7, pp. 1-12 (Year: 2017).*

Gurujeyalakshmi et al., "Taurine and Niacin Block Lung Injury and Fibrosis by Down-Regulating Bleomycin-Induced Activation of Transcription Nuclear Factor-kB in Mice", 2000, Journal of Pharmacology and Experimental Therapeutics, 293, pp. 82-90 (Year: 2000).*

Çevik et al., "Inhibition of Pseudomonas aeruginosa biofilm formation by 2,2'-bipyridyl, lipoic, kojic and picolinic acids", 2015, Iran J Basic Med Sci, 18, pp. 758-763 (Year: 2015).*

PubChem, "Picolinic acid", created 2004, National Library of Medicine, 65 pgs. (Year: 2004).*

Francois Daubeuf et al., "Performing Bronchoalveolar Lavage in the Mouse", *Current protocols in mouse biology* vol. 2, 167-175, (2012).

European Patent Office, Extended European Search Report for EP Application No. 20755169.8-1112, dated Dec. 9, 2022, 16 pages.

Glanz Victor Yu et al., Inhibition of sialidase activity as a therapeutic approach, Drug Design, Development and Therapy, vol. 12, Oct. 1, 2018, pp. 3431-3437, 7 pages.

Karhadkar Tejas R. et al., Sialidase inhibitors attenuate pulmonary fibrosis in a mouse model, Scientific Reports, vol. 7, No. 1, Nov. 8, 2017, p. 15069, 12 pages.

International Search Report and Written Opinion of International PCT Application No. PCT/US2020/017504; Mailing Date: Jul. 23, 2020, 14 pages.

N. Uzma et al., "In vitro and in vivo evaluation of toxic effect of benzene on lymphocytes and hepatocytes", The Internet Journal of Toxicology, 2008, vol. 6 No. 2, p. 1-7.

(Continued)

*Primary Examiner* — Brenda L Coleman
*Assistant Examiner* — Madeline E Braun
(74) *Attorney, Agent, or Firm* — Jackson Walker L.L.P.; Leisa Talbert Peschel

(57) ABSTRACT

The present disclosure relates to methods of preventing or inhibiting fibrosis using small molecule sialidase inhibitors. The present disclosure also relates to methods treating obesity, liver inflammation, steatosis, and cancer. These methods can involve administering the compounds to a patent at risk of developing fibrosis inflammation, obesity, steatosis, or cancer, in a manner that inhibits NEU3.

11 Claims, 46 Drawing Sheets

(56) References Cited

OTHER PUBLICATIONS

Darrell Pilling et al., "TNF-α-stimulated fibroblasts secrete lumican to promote fibrocyte differentiation", Proceedings of the National Academy of Sciences of the United States of America 112, 11929-11934 (2015).
Darrell Pilling et al., "Fibroblasts secrete Slit2 to inhibit fibrocyte differentiation and fibrosis", Proceedings of the National Academy of Sciences of the United States of America 111, 18291-18296 (2014).
Nehemiah Cox et al., "DC-SIGN activation mediates the differential effects of SAP and CRP on the innate immune system and inhibits fibrosis in mice", Proceedings of the National Academy of Sciences of the United States of America 112, 8385-8390 (2015).
Darrell Pilling et al., "Persistent Lung Inflammation and Fibrosis in Serum Amyloid P Component (Apcs) Knockout Mice," Public Library of Science ONE 9, e93730, vol. 9, Issue 4 (2014).
Yamaguchi, K., et al., "Reduced Susceptibility to Colitis-Associated Colon Carcinogenesis in Mice Lacking Plasma Membrane-Associated Sialidase", PLoS ONE, 2012. 7(7): p. e41132.
Pilling D, et al., "Serum Amyloid P and a Dendritic Cell-Specific Intercellular Adhesion Molecule-3-Grabbing Nonintegrin Ligand Inhibit High-Fat Diet-Induced Adipose Tissue and Liver Inflammation and Steatosis in Mice", Am J Pathol. Dec. 2019;189(12):2400-2413.
Mehlem, A., et al., "Imaging of neutral lipids by oil red O for analyzing the metabolic status in health and disease", Nat. Protoc., 2013. 8(6): p. 1149-54.

* cited by examiner

Total number of cells recovered from BAL (x 10^4)
CD11b positive cells recovered from BAL (x 10^4)
CD11c positive cells recovered from BAL (x 10^4)
CD45 positive cells recovered from BAL (x 10^4)
Ly6G positive cells recovered from BAL (x 10^4)
Ly6C positive cells recovered from BAL (x 10^4)
S B S B S B S B
Ctrl 2AP MP AMPCA

ANTI-FIBROTIC NEU3 INHIBITOR COMPOUNDS AND METHODS OF USE

CROSS-REFERENCE TO RELATED APPLICATIONS

The present application is a U.S. National Stage Application of International Application No. PCT/US2020/017504 filed Feb. 10, 2020, which claims priority to U.S. Provisional Application Ser. No. 62/804,262 filed Feb. 12, 2019, the contents of which are incorporated herein by reference in their entirety for all purposes.

STATEMENT OF GOVERNMENT INTEREST

This invention was made with government support under 1R01HL132919 and awarded by the National Institutes of Health. The government has certain rights in the invention.

FIELD OF THE DISCLOSURE

The present disclosure relates to anti-fibrotic, anti-cancer, anti-steatosis, anti-liver inflammation, and anti-obesity agents, and more specifically, inhibitors of the sialidase NEU3.

BACKGROUND

Fibrocytes are a specialized type of cell that plays an important role in the body's response to injury and in inflammation. Fibrocytes are formed when they differentiate from CD 14+ peripheral blood monocytes. Fibrocytes express markers of both hematopoietic (blood producing) cells (CD45, MHC class II, CD34) and stromal (structural tissue) cells (collagen types I and III and fibronectin). Mature fibrocytes secrete cytokines, extracellular matrix proteins, and pro-angiogenic molecules.

Fibrocytes and the molecules they display extracellularly or release often result in fibrosis, which is the development of scar tissue. Instead of normal wound healing in response to an injury, fibrosis (which may result from inappropriate fibrocyte formation or activity) is harmful if it occurs to too great an extent, for too long, or in an inappropriate location.

As a result, controlling the formation of fibrocytes and their activity in the body may help control harmful fibrosis, thereby avoiding or treating any resulting diseases or disorders.

Obesity is the accumulation of body fat as the result of excessive food intake and/or lack of exercise. Obesity reduces life expectancy and is associated with 300,000 death annually in the U.S. Obesity also increases the likelihood of conditions such as type 2 diabetes, atherosclerosis, and high blood pressure.

Transforming Growth Factor-β1 (TGF-β1) is a protein signal. Increased extracellular levels of active TGF-β1 are strongly associated with fibrosis. TGF-β1 is produced as an inactive protein complex with the latency-associated peptide (LAP), and TGF-β1 only drives fibrotic processes when it is released from the LAP complex.

Sialidases are enzymes that remove sialic acid from glycoconjugates. Sialidases such as NEU1 and NEU3 are upregulated in patients with pulmonary fibrosis. NEU3 is also upregulated in some cancers, such as colon, renal, ovarian, and prostate cancers. Overexpression of NEU3 in human colon cancer cells promotes cell proliferation and adhesion, suggesting that the high levels of NEU3 observed in some tumors may potentiate the tumor. In support of the role of NEU3 in cancer, Neu3−/− knockout mice have a reduced incidence of colitis-associated colon cancer.

In some cancers, high levels of NEU3 increase extracellular accumulation of the cytokine interleukin-6 (IL-6), and IL-6 is also associated with fibrosis. IL-6 also upregulates NEU3 in cultured human cells and some cancers.

Serum amyloid P (SAP) is a blood protein that inhibits fibrocyte differentiation. In support of the hypothesis that sialidases potentiate fibrosis, recombinant human NEU2, NEU3, and NEU4, when added to human peripheral blood mononuclear cells (PBMC), potentiate fibrocyte differentiation and counteract the ability of human SAP to inhibit fibrocyte differentiation.

Sialidases may thus potentiate fibrosis and cancer by a combination of increasing TGF-β1 and IL-6 levels.

In the liver, excess calories leads to Kupffer cell (hepatic macrophages) activation which then promotes inflammation, increased hepatocyte fatty acid synthesis leading to hepatic steatosis (abnormal retention of lipids within the hepatocytes). This, in turn, can lead to fibrosis or cirrhosis.

SUMMARY

The present disclosure provides a method of treating a fibrotic disorder, the method comprising administering a formulation comprising a compound of formula (I):

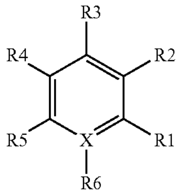

I or its salt, wherein:

In formula (I), $R_1$ may be selected from hydrogen, —$NO_2$, —CN, —COOH, —$CONH_2$, —$COCH_3$, $C_{2-5}$acyl, $C_{1-6}$alkyl ester, aryl ester, —$SO_3H$, —$SO_2NH_2$, —$SO_2NH(C_{1-6}$alkyl), —$SO_2NH(C_{1-6}$aryl), —$SO_3(C_{1-6}$alkyl), —$SO_3(C_{1-6}$aryl), —$PO_3H_2$, —$PO_2H_2$, —$PO_2NH(C_{1-6}$alkyl), —$PO_2NH(C_{1-6}$aryl), —$PO_2H(C_{1-6}$alkyl), —$PO_2H(C_{1-6}$ aryl), —$PO_3H(C_{1-6}$alkyl), —$PO_3H(C_{1-6}$aryl), and tetrazole.

In formula (I), $R_2$, $R_3$, and $R_4$ are independently selected from hydrogen, —$NO_2$, —CN, —$CF_3$, —$NH_2$, —$NH(C_{1-6}$alkyl), —$N(C_{1-6}$alkyl, $C_{1-6}$alkyl), —$CONH_2$, —OH, halo, $C_{1-6}$alkyl, aryl, —COOH, —$NHCO(C_{1-6}$alkyl), $C_{1-6}$alkyl ether, —$CO(C_{1-6}$alkyl, —CO(aryl), —$SO_3H$, —$SO_2NH_2$, —$SO_2NH(C_{1-6}$alkyl), —$SO_2NH(C_{1-6}$aryl), —$SO_3(C_{1-6}$alkyl), —$SO_3(C_{1-6}$aryl), —$PO_3H_2$, —$PO_2H_2$, —$PO_2NH(C_{1-6}$alkyl), —$PO_2NH(C_{1-6}$aryl), —$PO_2H(C_{1-6}$alkyl), —$PO_2H(C_{1-6}$aryl), —$PO_3H(C_{1-6}$alkyl), —$PO_3H(C_{1-6}$aryl), tetrazole, and 2-oxazolyl.

In formula (I), $R_5$ may be selected from hydrogen, —$CH_2OH$, hydroxypropyl, di-hydroxypropyl, tri-hydroxypropyl, —$NO_2$, —CN, —$CF_3$, —$NH_2$, —$NH(C_{1-6}$alkyl), —$N(C_{1-6}$alkyl, $C_{1-6}$alkyl), —$CONH_2$, —OH, halo, $C_{1-6}$alkyl, aryl, —COOH, —$NHCO(C_{1-6}$alkyl), —$CO(C_{1-6}$alkyl), —CO(aryl), —$SO_3H$, —$SO_2NH_2$, —$SO_2NH(C_{1-6}$alkyl), —$SO_2NH(C_{1-6}$aryl), —$SO_3(C_{1-6}$alkyl), —$SO_3(C_{1-6}$aryl), —$PO_3H_2$, —$PO_2H_2$, —$PO_2NH(C_{1-6}$alkyl), —$PO_2NH(C_{1-6}$aryl), —$PO_2H(C_{1-6}$alkyl), —$PO_2H(C_{1-6}$ aryl), —$PO_3H(C_{1-6}$alkyl), —$PO_3H(C_{1-6}$aryl), tetrazole, and 2-oxazolyl.

In formula (I), X may be selected from carbon and nitrogen.

The present disclosure also provides a method of treating a fibrotic disorder, obesity, steatosis, liver inflammation, or cancer by administering a formulation comprising a compound of formula (II):

II

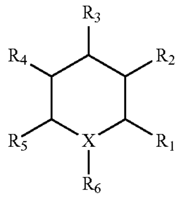

or its salt, wherein:

In formula II, $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2$NH ($C_{1-6}$alkyl), —$SO_2$N($C_{1-6}$alkyl)$_2$, —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$ aryl), —$PO_3$H($C_{1-6}$alkyl), —$PO_3$H($C_{1-6}$aryl), a tetrazole or other heterocycle.

In formula II, $R_2$, $R_3$, and $R_4$ may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2$N($C_{1-6}$aryl)$_2$, —$COCH_3$, $C_{2-5}$acyl, —CO(aryl), —$SO_3H$, —$SO_2NH_2$, —$SO_2$NH($C_{1-6}$alkyl), —$SO_2$NH($C_{1-6}$aryl), —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$ H($C_{1-6}$aryl), —$PO_3$H($C_{1-6}$alkyl), —$PO_3$H($C_{1-6}$aryl), tetrazole, 2-oxazolyl or other heterocycle.

In formula II, $R_5$ may be selected from hydrogen, a halogen, an alkyl group, an aryl group, —$CH_2$OH, hydroxypropyl, di-hydroxypropyl, tri-hydroxypropyl, —$NO_2$, —CN, —$CF_3$, —$NH_2$, —NH($C_{1-6}$alkyl), —N($C_{1-6}$alkyl, $C_{1-6}$alkyl), —$CONH_2$, —CONHOH, —OH, —CON(($C_{1-6}$alkyl)$_2$ or (aryl)$_2$), —CH(OH)$CH_3$, —CH (OH)($CH_2$OH), —CH(OH)(CH(OH)$CH_2$OH), —NHCO ($C_{1-6}$alkyl), $C_{1-6}$alkyl ether, an aryl ether, —$(CH_2)_{1-3}NH_2$, $C_{1-6}$alkyl, aryl, $C_{1-6}$alkyl ester, aryl ester —$(CH_2)_{1-3}NH_2$, —COOH, —NHCO($C_{1-6}$alkyl), —$COCH_3$, $C_{2-5}$acyl, —CO (aryl), —$SO_3H$, —$SO_2NH_2$, —$SO_2$NH($C_{1-6}$alkyl), —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), tetrazole, 2-oxazolyl or other heterocycle.

In formula II, $R_6$ may be selected from hydrogen, methyl, —$CF_3$, $C_{1-6}$alkyl, aryl, —CO($C_{1-6}$alkyl), or nothing.

In formula II, X may be selected from carbon, nitrogen, or oxygen.

The present disclosure also provides a method of treating a fibrotic disorder, obesity, steatosis, liver inflammation, or cancer by administering a formulation comprising a compound of formula (III):

III

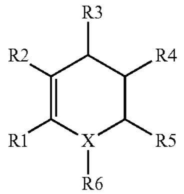

or its salt, wherein:

In formula III, $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2$NH ($C_{1-6}$alkyl), —$SO_2$N($C_{1-6}$alkyl)$_2$, —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), a tetrazole or other heterocycle.

In formula III, $R_2$, $R_3$, and $R_4$ may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2$N($C_{1-6}$aryl)$_2$, —$COCH_3$, $C_{2-5}$acyl, —CO(aryl), —$SO_3H$, —$SO_2NH_2$, —$SO_2$NH($C_{1-6}$alkyl), —$SO_2$NH($C_{1-6}$aryl), —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$ aryl), —$PO_3$H($C_{1-6}$alkyl), —$PO_3$H($C_{1-6}$aryl), tetrazole, 2-oxazolyl or other heterocycle.

In formula III, $R_5$ may be selected from hydrogen, a halogen, an alkyl group, an aryl group, —$CH_2$OH, hydroxypropyl, di-hydroxypropyl, tri-hydroxypropyl, —$NO_2$, —CN, —$CF_3$, —$NH_2$, —NH($C_{1-6}$alkyl), —N($C_{1-6}$alkyl, $C_{1-6}$alkyl), —$CONH_2$, —CONHOH, —OH, —CON(($C_{1-6}$alkyl)$_2$ or (aryl)$_2$), —CH(OH)$CH_3$, —CH (OH)($CH_2$OH), —CH(OH)(CH(OH)$CH_2$OH), —NHCO ($C_{1-6}$alkyl), $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —NHCO($C_{1-6}$alkyl), —$COCH_3$, $C_{2-5}$acyl, —CO (aryl), —$SO_3H$, —$SO_2NH_2$, —$SO_2$NH($C_{1-6}$alkyl), —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), tetrazole, 2-oxazolyl or other heterocycle.

In formula III, $R_6$ may be selected from hydrogen, methyl, —$CF_3$, $C_{1-6}$alkyl, aryl, —CO($C_{1-6}$alkyl), or nothing.

In formula III, X may be selected from carbon, oxygen, or nitrogen.

The present disclosure also provides a method of treating a fibrotic disorder, obesity, steatosis, liver inflammation, or cancer by administering a formulation comprising a compound of formula (IV):

IV

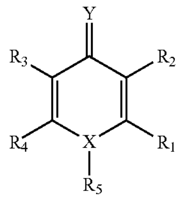

or its salt, wherein:

In formula IV, $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2$NH($C_{1-6}$alkyl), —$SO_2$N($C_{1-6}$alkyl)$_2$, —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), a tetrazole or other heterocycle.

In formula IV, $R_2$, $R_3$, and $R_4$ may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2$N($C_{1-6}$aryl)$_2$, —$COCH_3$, $C_{2-5}$acyl, —CO(aryl), —$SO_3H$, —$SO_2NH_2$, —$SO_2$NH($C_{1-6}$alkyl), —$SO_2$NH($C_{1-6}$aryl), —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$ aryl), —$PO_3$H($C_{1-6}$alkyl), —$PO_3$H($C_{1-6}$aryl), tetrazole, 2-oxazolyl or other heterocycle.

In formula IV, $R_5$ may be selected from hydrogen, methyl, —$CF_3$, $C_{1-6}$alkyl, aryl, —CO($C_{1-6}$alkyl), or nothing.

In formula IV, X may be selected from carbon, oxygen, or nitrogen.

In formula IV, Y may be selected from oxygen, a hydroxyl group, a di-methyl nitrogen, or a methylene group.

The present disclosure provides a method of treating a fibrotic disorder, obesity, steatosis, liver inflammation, or cancer by administrating a formulation comprising a compound of formula (V)

V

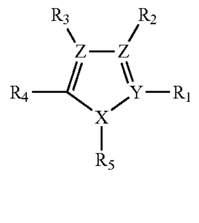

or its salt, wherein:

In formula V $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2$NH($C_{1-6}$alkyl), —$SO_2$N($C_{1-6}$alkyl)$_2$, —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), a tetrazole or other heterocycle.

In formula V, $R_2$ and $R_3$, may be independently selected from hydrogen, a halogen, an alkyl group, an aryl group, —$NO_2$, —CN, —$CF_3$, —$NH_2$, —NH($C_{1-6}$alkyl), $C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$ alkyl), $C_{1-6}$alkyl ether, an aryl ether, —$(CH_2)_{1-3}NH_2$, —$SO_2$N($C_{1-6}$aryl)$_2$, —$COCH_3$, $C_{2-5}$acyl, —CO(aryl), —$SO_3H$, —$SO_2NH_2$, —$SO_2$NH($C_{1-6}$alkyl), —$SO_2$NH($C_{1-6}$aryl), —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), tetrazole, 2-oxazolyl or other heterocycle.

In formula V, $R_4$ may be selected from hydrogen, a halogen, an alkyl group, an aryl group, —$CH_2$OH, hydroxypropyl, di-hydroxypropyl, tri-hydroxypropyl, —$NO_2$, —CN, —$CF_3$, —$NH_2$, —NH($C_{1-6}$alkyl), —N($C_{1-6}$alkyl, $C_{1-6}$alkyl), —$CONH_2$, —CONHOH, —OH, —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —NHCO($C_{1-6}$alkyl), —$COCH_3$, $C_{2-5}$acyl, —CO(aryl), —$SO_3H$, —$SO_2NH_2$, —$SO_2$NH($C_{1-6}$alkyl), —$SO_2$NH($C_{1-6}$aryl), —$SO_2$N($C_{1-6}$aryl)$_2$, —$SO_3$($C_{1-6}$alkyl), —$SO_3$($C_{1-6}$aryl), —$PO_3H_2$, —$PO_2H_2$, —$PO_2$NH($C_{1-6}$alkyl), —$PO_2$NH($C_{1-6}$aryl), —$PO_2$H($C_{1-6}$alkyl), —$PO_2$H($C_{1-6}$aryl), —$PO_3$H($C_{1-6}$alkyl), —$PO_3$H($C_{1-6}$aryl), tetrazole, 2-oxazolyl or other heterocycle.

In formula V, $R_5$ may be selected from hydrogen, methyl, —$CF_3$, $C_{1-6}$alkyl, aryl, —CO($C_{1-6}$alkyl), or nothing.

In formula V, X may be selected from carbon, oxygen, or nitrogen.

In formula V, Y may be selected from carbon or nitrogen.

In formula V, Z may be selected from carbon, nitrogen, oxygen, or sulfur.

The present disclosure provides a method of treating a fibrotic disorder, obesity, steatosis, liver inflammation, or cancer by administrating a formulation comprising a compound of formula (VI):

VI

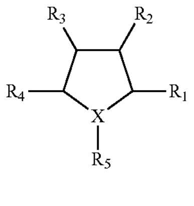

or its salt, wherein:

In formula VI, $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2NH$($C_{1-6}$alkyl), —$SO_2N$($C_{1-6}$alkyl)$_2$, —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), a tetrazole or other heterocycle.

In formula VI, $R_2$ and $R_3$, may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2N$($C_{1-6}$aryl)$_2$, —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VI, $R_4$ may be selected from hydrogen, a halogen, an alkyl group, an aryl group, —$CH_2$OH, hydroxypropyl, di-hydroxypropyl, tri-hydroxypropyl, —$NO_2$, —CN, —$CF_3$, —$NH_2$, —NH($C_{1-6}$alkyl), —N($C_{1-6}$alkyl, $C_{1-6}$alkyl), —$CONH_2$, —CONHOH, —OH, —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —NHCO($C_{1-6}$alkyl), —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VI, $R_5$ may be selected from hydrogen, methyl, —$CF_3$, $C_{1-6}$alkyl, aryl, —CO($C_{1-6}$alkyl), or nothing.

In formula VI, X may be selected from carbon, oxygen, or nitrogen.

The present disclosure provides a method of treating a fibrotic disorder, obesity, steatosis, liver inflammation, or cancer by administrating a formulation comprising a compound of formula (VII):

VII

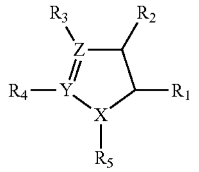

or its salt, wherein:

In formula VII, $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2NH$($C_{1-6}$alkyl), —$SO_2N$($C_{1-6}$alkyl)$_2$, —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$ aryl), —$PO_3H$($C_{1-6}$alkyl), —$PO_3H$($C_{1-6}$aryl), a tetrazole or other heterocycle.

In formula VII, $R_2$ and $R_3$, may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2N$($C_{1-6}$aryl)$_2$, —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VII, $R_4$ may be selected from hydrogen, a halogen, an alkyl group, an aryl group, —$CH_2$OH, hydroxypropyl, di-hydroxypropyl, tri-hydroxypropyl, —$NO_2$, —CN, —$CF_3$, —$NH_2$, —NH($C_{1-6}$alkyl), —N($C_{1-6}$alkyl, $C_{1-6}$alkyl), —$CONH_2$, —CONHOH, —OH, —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —NHCO($C_{1-6}$alkyl), —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VII, $R_5$ may be selected from hydrogen, methyl, —$CF_3$, $C_{1-6}$alkyl, aryl, —CO($C_{1-6}$alkyl), or nothing.

In formula VII, X may be selected from carbon, oxygen, or nitrogen.

In formula VII, Y may be selected from carbon or nitrogen.

In formula VII, Z may be selected from carbon, nitrogen, oxygen, or sulfur.

The present disclosure provides a method of treating a fibrotic disorder, obesity, steatosis, liver inflammation, or cancer by administrating a formulation comprising a compound of formula (VIII):

VIII

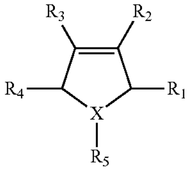

or its salt, wherein:

In formula VIII, $R_1$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2NH$($C_{1-6}$alkyl), —$SO_2N$($C_{1-6}$alkyl)$_2$, —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$ aryl), —$PO_3H$($C_{1-6}$alkyl), —$PO_3H$($C_{1-6}$aryl), a tetrazole or other heterocycle.

In formula VIII, $R_2$ and $R_3$, may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2N$($C_{1-6}$aryl)$_2$, —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VIII, $R_4$ may be selected from hydrogen, a halogen, an alkyl group, an aryl group, —$CH_2$OH, hydroxypropyl, di-hydroxypropyl, tri-hydroxypropyl, —$NO_2$, —CN, —$CF_3$, —$NH_2$, —NH($C_{1-6}$alkyl), —N($C_{1-6}$alkyl, $C_{1-6}$alkyl), —$CONH_2$, —CONHOH, —OH, —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —NHCO($C_{1-6}$alkyl), —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VIII, $R_5$ may be selected from hydrogen, methyl, —$CF_3$, $C_{1-6}$alkyl, aryl, —CO($C_{1-6}$alkyl), or nothing.

In formula VIII, X may be selected from carbon, oxygen, or nitrogen.

The present disclosure provides a method of treating a fibrotic disorder, obesity, steatosis, liver inflammation, or cancer by administrating a formulation comprising a compound of formula (IX):

IX

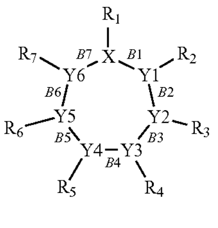

or its salt, wherein:

In formula IX, B1, B2, B3, B4, B5, B6, and/or B7 may be selected from a single or double (olefin) bonds;

In formula IX, $R_1$ may be selected from hydrogen, methyl, —$CF_3$, $C_{1-6}$alkyl, aryl, —CO($C_{1-6}$alkyl), or nothing.

In formula IX, $R_2$-$R_6$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2NH$($C_{1-6}$alkyl), —$SO_2N$($C_{1-6}$alkyl)$_2$, —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$ aryl), —$PO_3H$($C_{1-6}$alkyl), —$PO_3H$($C_{1-6}$aryl), a tetrazole or other heterocycle.

In formula IX, $R_7$ may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$alkyl), $C_{1-6}$alkyl ether, an aryl ether, —$(CH_2)_{1-3}NH_2$, —$SO_2N$($C_{1-6}$aryl)$_2$, —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula IX, X may be selected from carbon, oxygen, or nitrogen.

In formula IX, Y may be selected from carbon, nitrogen, oxygen, or sulfur.

The above methods may be combined with one another and alone or in combination may further include one or more of the following additional features, unless clearly mutually exclusive:

i. the method may inhibit desialylation of LAP;
ii. the method may inhibit desialylation of SAP;
iii. the method may inhibit the formation or activation of fibrocytes;
iv. the method may decrease the level or activity of TGF-β1 in a human;
v. the compound may decrease the level of interleukin-6 in a human;
vi. the method may decrease the level or activity of a sialidase in a human;
vii. the method may inhibit more than one sialidase;
viii. the compound may be administered to a human locally in an area in which human sialidase activity is abnormally high;
ix. the formulation may be administered via intravenous or intraperitoneal injection, orally, topically, via inhalation, or via other means of enteral or parenteral administration;
x. the compound used in the method is DANA;
xi. the compound used in the method is 4-hydroxypyridine-2-carboxylic acid;
xii. the compound used in the method is 5-acetamidopyridine-2-carboxylic acid;
xiii. the compound used in the method is picolinic acid;
xiv. the compound used in the method is 2-acetylpyridine;
xv. the compound used in the method is methyl picolinate;

xvi. the compound used in the method is 4-amino picolinic acid;
xvii. the compound used in the method is 5-nitro picolinic acid;
xviii. the compound used in the method is 4-methoxy picolinic acid;
xix. the compound used in the method is picolinamide;
xx. the compound used in the method is 5-acetylamino-4-amino picolinic acid;
xxi. the compound used in the method is 1,4,5,6-tetrahydropyridine-2-carboxylate;
xxii. the compound used in the method is L-pipecolinic acid;
xxiii. the compound used in the method is nicotinic acid;
xxiv. the compound used in the method is salicylic acid;
xxv. the compound used in the method is O-(tetrahydro-2H-pyran-2-yl)-hydroxylamine;
xxvi. the compound used in the method is 6-(hydroxymethyl) picolinic acid;
xxvii. the compound used in the method is 5-aminopyridine-2-carboxylic acid;
xxviii. the compound used in the method is 2-Nitropyridine;
xxix. the compound used in the method is 1-methyl-2-piperidine carboxylic acid;
xxx. the compound used in the method is 4-(triflurommethyl) picolinic acid;
xxxi. the compound used in the method is 4-methylpicolinic acid;
xxxii. the compound used in the method is 4-aminonicotinic acid;
xxxiii. the compound used in the method is 4-oxo-1,4-dihydropyridine-2-carboxylic acid;
xxxiv. the compound used in the method is 2-piperidinecarboxylic acid, 4-amino;
xxxv. the compound used in the method is 2-piperidinecarboxylic acid, 4-amino-1-methyl;
xxxvi. the compound used in the method is 2-pyridinecarboxylic acid, 6-methyl;
xxxvii. the compound used in the method is oseltamivir;
xxxviii. the compound used in the method is D-proline;
xxxix. the compound used in the method is pyrrole-2-carboxylic acid;
xl. the compound used in the method is azepane-2-carboxylic acid; and
xli. the dose administered may be sufficient to establish a systemic concentration or a concentration in the area of administration of at least 3 μM. Dosing may be daily for at least one week, at least two weeks, at least three weeks, or indefinitely;
xlii. the dose administered may be sufficient to decrease the amount of neutral lipids in the liver of a human; and
xliii. the dose administered may be sufficient to decrease the level of activity of a sialidase in a human.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The figures form part of the present specification and are included to further demonstrate certain aspects of the present invention. The figures are not intended to and should not be interpreted to encompass the entirety of the invention. In addition, different aspects of the invention are often illustrated as separate figures for clarity; these aspects may be combined with one another unless clearly not compatible.

FIG. 5B shows IL-6 accumulation after 48 hours. FIG. 5C shows IL-6 accumulation after 5 days. Values are mean±SEM, n=3. $*=p\leq 0.05$, $**=p\leq 0.01$ compared to 0 NEU3 (t test).

FIG. 5D shows IL-6 accumulation after 48 hours. FIG. 5E shows IL-6 accumulation after 5 days. Values are mean±SEM, n=3. $*=p\leq 0.05$ compared to 0 NEU3 (t test).

FIG. 8A shows total cell count in bronchoalveolar lavage after different treatments: saline (S), bleomycin (B), saline+2-acetylpyridine (2AP), bleomycin+2-acetyl pyridine, saline+methyl picolinate (MP), bleomycin+methyl picolinate, saline+2-piperidinecarboxylic acid, 4-amino-1-methyl (AMPCA) and bleomycin+2-piperidinecarboxylic acid, 4-amino-1-methyl. FIG. 8B-F breaks down the total cell count by cell type: CD11b-positive cells (FIG. 8B), CD11c-positive cells (FIG. 8C), CD45-positive cells (FIG. 8D), Ly6G-positive cells (FIG. 8E) and Ly6C-positive cells (FIG. 8F). Values are mean±SEM, n≥3. $*=p\leq 0.05$, $=p\leq 0.01$, $*=p\leq 0.001$, $****=p\leq 0.0001$ (1-way ANOVA, Bonferroni's test), #=p≤0.05, ##=p≤0.01, ###=p≤0.001 (t-test).

FIG. 9A is the control saline treated, FIG. 9B is bleomycin treated, FIG. 9C is saline and 2-acetyl pyridine treated, FIG. 9D bleomycin and 2-acetyl pyridine treated, FIG. 9E is saline and methyl picolinate treated, FIG. 9F is bleomycin and methyl picolinate treated, FIG. 9G is saline and 2-piperidinecarboxylic acid, 4-amino-1-methyl treated and FIG. 9H is bleomycin and 2-piperidinecarboxylic acid, 4-amino-1-methyl treated. Bar in FIG. 9A is 200 μM.

FIG. 11A is saline and bleomycin with no drugs, FIG. 11B is saline and bleomycin with 2AP, FIG. 11C is saline and bleomycin with MP, and FIG. 11D is saline and bleomycin with AMPCA. Values are mean±SEM, n=3. *=p≤0.05, =p≤0.01, *=p≤0.001 (t-test).

DETAILED DESCRIPTION

Figure 1:
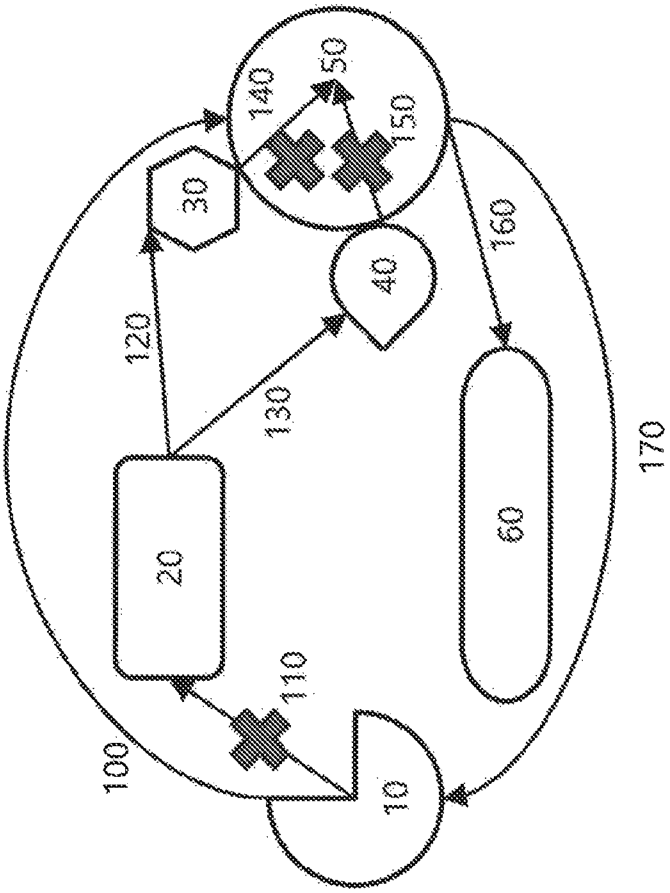
FIG. 1 is a not-to-scale schematic diagram of feedback pathways between sialidases and fibrosis.

The present disclosure relates to anti-fibrotic compounds and methods of preventing or inhibiting fibrosis using such compounds. The compounds and methods may also prevent or inhibit fibrocyte formation, including proliferation, or fibrocyte activity, including activation, that may give rise to fibrosis.

The compounds may inhibit a sialidase, particularly human NEU3.

The methods may involve administering the compounds to a patient with or at risk of developing fibrosis or with abnormal fibrocyte formation, including proliferation, or activity, including activation. The amount of compound administered, the mode of administration, the dose, and frequency of any repetitions may vary depending on the compound and effect to be achieved.

The methods may also include administering the compounds to a patient with or at risk of steatosis or Nonalcoholic Steatohepatitis. The amount of compound administered, the mode of administration, the dose, and frequency of any repetitions may vary depending on the compound and effect to be achieved.

The methods may also include administering the compounds to a patent with or at risk of cancer, including cancers with upregulated NEU3. The amount of compound administered, the mode of administration, the dose, and frequency of any repetitions may vary depending on the compound and effect to be achieved.

The methods may also include administering the compounds to a patient with or at risk of obesity, including obesity caused by high-fat diet. The amount of compound administered, the mode of administration, the dose, and frequency of any repetitions may vary depending on the compound and effect to be achieved.

Sialidases and Fibrosis

A protein with an attached polysaccharide is referred to as a glycosylated protein. Many of the polysaccharides on glycosylated proteins have a sialic acid monosaccharide, particularly at the end distal to the protein (referred to as a terminal sialic acid). Sialidases (also called neuraminidases) are enzymes that remove sialic acid from polysaccharides found on glycosylated proteins.

Sialidases are used by a wide variety of organisms, including harmful viruses and bacteria. Mammals have four sialidases, designated NEU1, NEU2, NEU3, and NEU4.

NEU1 is generally expressed at higher levels than the other three sialidases and it is expressed in most tissues, with higher levels in the lung and airway epithelial cells than in most other cells. NEU1 is located in lysosomes and in some conditions on the plasma membrane, with its catalytic domain outside the cell. NEU1 preferentially desialylates terminal sialic acids with α(2,3)-linkages and to a lesser extent α(2,6)-linkages, with also some activity for α(2,8)-linkages.

NEU2 is a soluble, cytosolic enzyme. NEU2 preferentially desialylates terminal sialic acids with α(2,3)-linkages, α(2,6)-linkages, and α(2,8)-linkages.

NEU3 is a plasma membrane-associated sialidase, and is the only sialidase that is found extracellularly. NEU3 preferentially desialylates terminal sialic acids with α(2,6)-linkages.

NEU4 has two isoforms, one with a mitochondrial localization, while the other is associated with intracellular membranes. NEU4 preferentially desialylates terminal sialic acids with α(2,3)-linkages, α(2,6)-linkages, and α(2,8)-linkages.

Variants of these four sialidases are known in humans and in other mammals. In particular, variants with single nucleotide polymorphisms (SNPs) are known.

Sialidases are associated with inflammation in mammals and inflammation increases the presence of sialidases. Thus, a positive feedback loop exists between inflammation and sialidases in mammals.

The present disclosure exploits a newly discovered feedback pathway between sialidases and fibrosis in mammals, including humans. At least a portion of this pathway is illustrated in FIG. 1.

SAP 20, when in its normal glycosylated form, binds to DC-SIGN 30 via binding pathway 120. This causes DC-SIGN 30 to inhibit activation of profibrotic innate immune system cell 50 via inhibition pathway 140.

SAP 20, when in its normal glycosylated from, may also bind to Fc gamma Receptor 1 (FcγRl) 40 via binding pathway 130. This causes RcγRl to inhibit activation of profibrotic innate immune system cell 50 via inhibition pathway 150.

In the absence of inhibition, profibrotic innate immune system cell 50 may secrete cytokines, including TGF-β1, Tumor Necrosis Factor α (TNFα), Interleukin-4 (IL-4), IL-6, and IL-13. These cytokines act via pathways 160 to cause the formation or activation of fibroblasts 60. Fibroblasts 60 may then go on to cause fibrosis.

In addition, TGF-β1 secreted by innate immune system cell 50, present internally in innate immune system cell 50 in increased amounts, or otherwise present in the extracellular environment, may increase the expression of sialidase 10 via pathway 170.

Sialidase 10, in turn, may activate TGF-β1. TGF-β1 may be bound by LAP, which inactivates TGF-β1. Sialidase 10 can cleave the sialic acid from LAP, which releases and activates TGF-β1.

When SAP 20 binds to either DC-SIGN 30, RcγRl 40, or both, causing inhibition of profibrotic innate immune system cell 50, then the secretion of profibrotic cytokines is reduced and formation or activation of fibroblasts 60 is reduced.

Sialidase 10 may act via general pathway 100 to promote the secretion of cytokines by profibrotic innate immune system cell 50 and the formation or activation of fibroblasts 60.

Pathway 100 may include a variety of subpathways, but in at least one subpathway, sialidase 10 acts upon glycosylated SAP 20 to cleave the terminal sialic acid from the SAP polysaccharide. Sialidase 10 may be NEU1, which is able to cleave the type of sialic acid linkage present on glycosylated SAP. It may also be NEU2, NEU3, NEU4, or a combination of any sialidases.

Cleaving the sialic acid from glycosylated SAP 20 is an inhibitory process, as illustrated by pathway 110. SAP 20 lacking sialic acid is not able to effectively bind to DC-SIGN 30 or RcγRl 40 via pathway 120 or pathway 130, and thus SAP 20 is not able to inhibit profibrotic innate immune system cell 50 via inhibitory pathways 140 and 150. This leaves profibrotic innate immune system cell 50 free to promote the formation or activation of fibroblasts 60.

In addition to promoting the formation or activation of fibroblasts 60, profibrotic innate immune system cell 50, or possibly fibroblasts 60, also act via pathway 170 to further active sialidase 10. Thus, via pathways 100 and 170, fibrocyte formation or activation and sialidase activity form a positive feedback loop.

This positive feedback loop may be beneficial in some biological contexts, but it may also contribute to runaway fibrosis in fibrosing diseases and disorders. The present disclosure, therefore, provides compounds to disrupt this positive feedback look and methods of using them to prevent or control the damaging effects of fibrocyte formation or activation.

As an example of this positive feedback loop, NEU3 causes human PBMC to accumulate IL-6, which in turn induces human PBMC to accumulate NEU3. For this reason, NEU3 is a preferential, but not the only, target for compounds 1-31.

Similarly, TGF-β1 can induce a positive feedback loop. TGF-β1 is synthesized as inactive complex L-TGF-β1, where TGF-β1 is bound to two inactive latency-associated peptides (LAPs). These LAPs are sialylated, and release TGF-β1 when desialylated. NEU3 can desialylate LAP, thus releasing TGF-β1. Just like IL-6 above, active TGF-β1 induces human PBMCs to accumulate NEU3, forming a feedback look. This is another reason NEU3 is a preferential, but not the only, target for compounds 1-31.

As a third example of this positive feedback loop, one sialidase, such as NEU2, may increase expression of another sialidase, such as NEU3. These example feedback loops may all be present in the same cells or biological system and other feedback loops may further be present as well.

Sialidases and Steatosis

Steatosis (fatty liver, generally caused by obesity, diabetes, or alcohol intake) affects approximately 25-30% of the US population. A subset of the population with steatosis, comprising ~5% of the US population, has a more severe form of liver disease called Nonalcoholic Steatohepatitis ("NASH"). NASH involves liver damage and an excess of immune cells in the liver (inflammation). Patients with NASH can develop liver fibrosis (cirrhosis) and liver cancer.

In the liver, excess calories leads to Kupffer cell (hepatic macrophages) activation which then promotes inflammation, increased hepatocyte fatty acid synthesis leading to hepatic steatosis (abnormal retention of lipids within the hepatocytes), and eventual fibrosis or cirrhosis. Because sialidase inhibition reduces inflammation and fibrosis, and steatosis is related to inflammation and fibrosis, this specification also relates to use of sialidase inhibitors to treat steatosis and NASH.

Sialidases and Cancer

NEU3 is markedly up-regulated in many types of cancers including colon, ovarian, prostate, and renal carcinomas and suppresses apoptosis of cancer cells. In the human renal cell carcinoma cell line ACHN, IL-6 treatment enhanced NEU3 promoter activity and sialidase activity. Thus, the specification relates to using inhibitors of NEU3 to treat cancer, including cancers with elevated NEU3 activity.

Sialidases and Obesity

In obese rodents and humans, there are altered levels of NEU1 and NEU3 mRNAs, altered levels of NEU1 and NEU3 proteins, and altered levels of neuraminidase enzymic activity in white fat, intestines, and liver. Compared to non-obese control mice (db/+), obese (db/db) mice on a regular diet have reduced NEU1 mRNA levels and reduced NEU1 enzyme activity in liver tissue, but increased NEU1 enzyme activity in epididymal white fat. Compared to non-obese humans, obese patients have higher NEU3 mRNA in the small intestine, and NEU3 protein was also increased in the small intestines of HFD-treated mice as compared to regular diet mice. In addition, oral administration of the sialidase inhibitor DANA inhibited NEU3 enzymic activity in the small intestine, but not in the liver and white adipose tissue, and oral administration of DANA attenuated hepatic steatosis and HFD-induced weight gain, in mice. NEU3 overexpression in the liver using adenovirus-mediated expression improved glucose tolerance and insulin sensitivity, but increased hepatic triglyceride and glycogen accumulation and induced hyperlipidemia. Together, these disparate results suggest some connection between obesity and sialidases.

Altered sialidase levels appear to lead to altered insulin signaling. NEU1 can desialylate both insulin and insulin-like growth factor 1 receptors, leading to increased insulin receptor signaling at lower concentrations of insulin. Long-term hepatic NEU1 overexpression through adenovirus-based gene transfer increases glucose intolerance and insulin resistance in mice exposed to HFD. Reduced liver NEU3 protein levels also appear to be associated with reduced insulin signaling, whereas increased NEU3 protein in the liver increases insulin sensitivity and glucose tolerance in mice.

The sialidase inhibitor DANA prevents weight gain in mice fed a high fat diet. Furthermore, DANA had no effect on mice fed a normal diet, suggesting that DANA has a low risk of side effects.

Sialidase Inhibitors

The present disclosure includes sialidase inhibitors, particularly human NEU3 inhibitors, and their use in preventing or inhibiting fibrosis, obesity, liver inflammation, steatosis, and cancer.

Human NEU3 inhibitors may inhibit the enzymatic activity of all human sialidases, a subset of human sialidases, or only NEU3, all in wild type form alone or also including one or more active variants. Enzymatic activity may be defined as inhibited if the rate in an in vitro assay using a substrate with a terminal sialic acid is inhibited by at least 50%. More specifically, a NEU3 inhibitor may be a compound that inhibits the rate of NEU3 by at least 50% in an in vitro assay using the fluorometric substrate 4MU-NANA [2'-(4-Methylumbelliferyl)-α-D-N-acetylneuraminic acid.

Human NEU3 inhibitors may also inhibit TGF-β1 activity or level, which may interrupt the positive feedback loop described in FIG. 1 and thus also prevent or inhibit fibrosis.

Human NEU3 inhibitors may also inhibit extracellular IL-6 accumulation or concentration, which may decrease inflammation.

Human NEU3 inhibitors may also reduce the elevated NEU3 activity observed in many cancers, which may treat the cancer.

Human sialidase inhibitors may also reduce weight gain and improve glucose tolerance.

Human sialidase inhibitors may also inhibit liver inflammation.

Human sialidase inhibitors may also inhibit steatosis.

Small Molecule NEU3 Inhibitors

Small molecule NEU3 inhibitors, particularly human NEU3 inhibitors, may include the compound having the following structural formula:

(Compound 1)

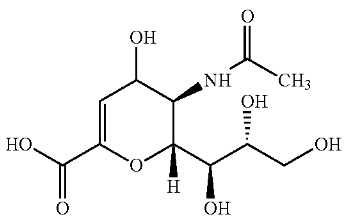

Compound 1, also known as DANA, inhibits human NEU3 with an inhibitor concentration that reduces enzymatic activity to 50% ($IC_{50}$) of 250 μM in the TGF-β1 release assay.

Small molecule NEU3 inhibitors may also include compounds having the following structural formula:

(Compound 2)

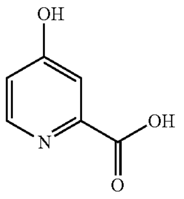

Compound 2, also known as 4-hydroxypyridine-2-carboxylic acid, inhibits human NEU3 with an $IC_{50}$ of 2.1 μM in the TGF-β1 concentration assay. Compound 2 has an $IC_{50}$ of >300 μM in the IL-6 concentration assay.

Small molecule NEU3 inhibitors may also include compounds having the following structural formula:

(Compound 3)

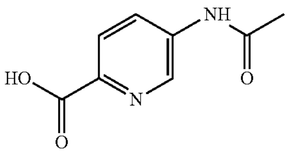

Compound 3, also known as 5-acetamidopyridine-2-carboxylic acid, inhibits human NEU3 with an $IC_{50}$ of 11 nM in the TGF-β1 concentration assay. Compound 3 has an $IC_{50}$ of 6.2 μM in the IL-6 concentration assay.

Small molecule NEU3 inhibitors may also include compounds having the following structural formula:

(Compound 4)

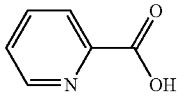

Compound 4, also known as picolinic acid, inhibits human NEU3 with an $IC_{50}$ of <10 pM in the TGF-β1 concentration assay. Compound 4 has an $IC_{50}$ of >100 μM in the IL-6 concentration assay.

Small molecule NEU3 inhibitors may also include compounds having the following structural formula:

(Compound 5)

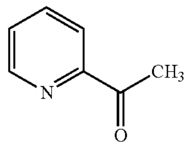

Compound 5, also known as 2-acetylpyridine, inhibits human NEU3 with an $IC_{50}$ of 42 nM in the TGF-β1 concentration assay. Compound 5 has an $IC_{50}$ of 32 μM in the IL-6 concentration assay.

Small molecule NEU3 inhibitors may also include compounds having the following structural formula:

(Compound 6)

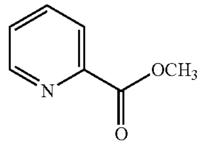

Compound 6, also known as methyl picolinate, inhibits human NEU3 with an $IC_{50}$ of 14 pM in the TGF-β1 concentration assay. Compound 6 has an $IC_{50}$ of >100 μM in the IL-6 concentration assay.

Small molecule NEU3 inhibitors may also include compounds having the following structural formula:

(Compound 7)

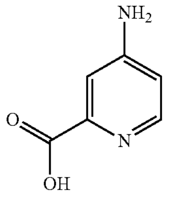

Compound 7, also known as 4-amino picolinic acid, inhibits human NEU3 with an $IC_{50}$ of 4.0 nM in the TGF-β1 concentration assay. Compound 7 has an $IC_{50}$ of >100 μM in the IL-6 concentration assay.

Small molecule NEU3 inhibitors may also include compounds having the following structural formula:

(Compound 8)

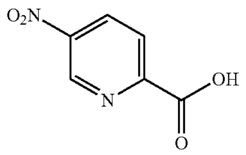

Compound 8, also known as 5-nitro picolinic acid, inhibits human NEU3 with an $IC_{50}$ of 43 nM in the TGF-β1 concentration assay. Compound 8 has an $IC_{50}$ of 79 nM in the IL-6 concentration assay.

Small molecule NEU3 inhibitors may also include compounds having the following structural formula:

(Compound 9)

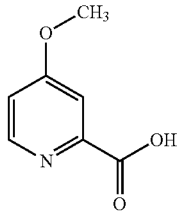

Compound 9, also known as 4-methoxy picolinic acid, inhibits human NEU3 with an $IC_{50}$ of 3.2 nM in the TGF-β1 concentration assay. Compound 9 has an $IC_{50}$ of >100 μM in the IL-6 concentration assay.

Small molecule NEU3 inhibitors may also include compounds having the following structural formula:

(Compound 10)

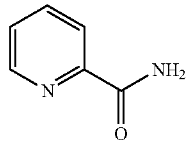

Compound 10, also known as picolinamide, inhibits human NEU3 with an $IC_{50}$ of 22 nM in the TGF-β1 concentration assay. Compound 10 has an $IC_{50}$ of >100 μM in the IL-6 concentration assay.

Small molecule NEU3 inhibitors may also include compounds having the following structural formula:

(Compound 11)

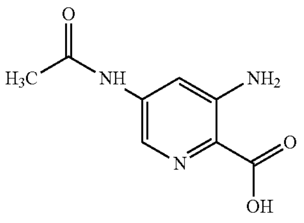

Compound 11, also known as 5-acetylamino-4-amino picolinic acid, inhibits human NEU3 with an $IC_{50}$ of 0.11 μM in the TGF-β1 concentration assay.

Small molecule NEU3 inhibitors may also include compounds having the following structural formula:

(Compound 12)

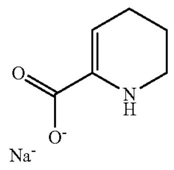

Compound 12, also known as sodium 1,4,5,6-tetrahydropyridine-2-carboxylate, inhibits human NEU3 with an $IC_{50}$ of 120 μM in the TGF-β1 concentration assay.

Small molecule NEU3 inhibitors may also include compounds having the following structural formula:

(Compound 13)

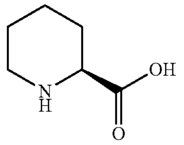

Compound 13, also known as L-pipecolinic acid, inhibits human NEU3 with an $IC_{50}$ of 0.49 nM in the TGF-β1 concentration assay. Compound 13 has an $IC_{50}$ of 7.9 μM in the IL-6 concentration assay.

Small molecule NEU3 inhibitors may also include compounds having the following structural formula:

(Compound 14)

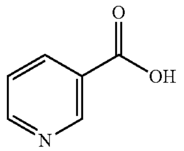

Compound 14, also known as nicotinic acid, inhibits human NEU3 with an $IC_{50}$ of 11 pM in the TGF-β1 concentration assay. Compound 14 has an $IC_{50}$ of 1.5 μM in the IL-6 concentration assay.

Small molecule NEU3 inhibitors may also include compounds having the following structural formula:

(Compound 15)

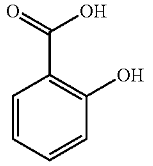

Compound 15, also known as salicylic acid, inhibits human NEU3 with an $IC_{50}$ of 1.8 μM in the TGF-β1 concentration assay.

Small molecule NEU3 inhibitors may also include compounds having the following structural formula:

(Compound 16)

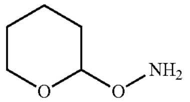

Compound 16, also known as O-(tetrahydro-2H-pyran-2-yl)-hydroxylamine, inhibits human NEU3 with an $IC_{50}$ of 2.6 μM in the TGF-β1 concentration assay.

(Compound 17)

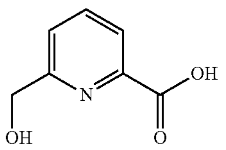

Compound 17, also known as 6-(hydroxymethyl) picolinic acid, inhibits human NEU3 with an $IC_{50}$ of 50 pM in the TGF-β1 concentration assay. Compound 17 has an $IC_{50}$ of 0.038 μM in the IL-6 concentration assay.

(Compound 18)

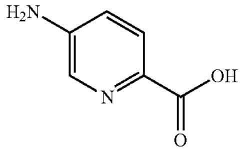

Compound 18, also known as 5-aminopyridine-2-carboxylic acid, inhibits human NEU3 with an $IC_{50}$ of 40 nM in the TGF-β1 concentration assay. Compound 18 has an $IC_{50}$ of 0.14 μM in the IL-6 concentration assay.

(Compound 19)

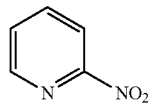

Compound 19, also known as 2-Nitropyridine, inhibits human NEU3 with an $IC_{50}$ of 40 nM in the TGF-β1 concentration assay. Compound 19 has an $IC_{50}$ of 0.02 μM in the IL-6 concentration assay.

(Compound 20)

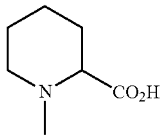

Compound 20, also known as 1-methyl-2-piperidine carboxylic acid, inhibits human NEU3 with an $IC_{50}$ of 0.50 μM in the TGF-β1 concentration assay. Compound 20 has an $IC_{50}$ of 0.03 μM in the IL-6 concentration assay.

(Compound 21)

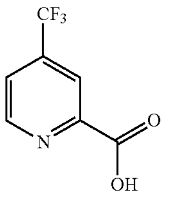

Compound 21, also known as 4-(trifluoromethyl) picolinic acid, has an $IC_{50}$ of 0.08 nM in the IL-6 concentration assay.

(Compound 22)

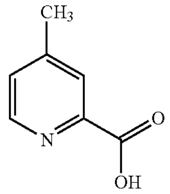

Compound 22, also known as 4-methylpicolinic acid, inhibits human NEU3 with an $IC_{50}$ of 0.13 μM in the TGF-β1 concentration assay. Compound 22 has an $IC_{50}$ of 4.7 μM in the IL-6 concentration assay.

(Compound 23)

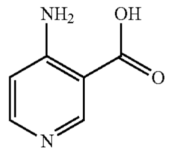

Compound 23, also known as 4-aminonicotinic acid, inhibits human NEU3 with an $IC_{50}$ of 5.0 nM in the TGF-β1 concentration assay. Compound 23 has an $IC_{50}$ of 10 μM in the IL-6 concentration assay.

(Compound 24)

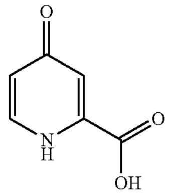

Compound 24, also known as 4-oxo-1,4-dihydropyridine-2-carboxylic acid, inhibits human NEU3 with an $IC_{50}$ of 0.13 μM in the TGF-β1 concentration assay. Compound 24 has an $IC_{50}$ of 8.5 μM in the IL-6 concentration assay.

(Compound 25)

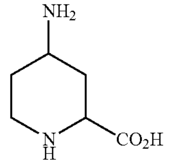

Compound 25, also known as 2-piperidinecarboxylic acid, 4-amino, inhibits human NEU3 with an $IC_{50}$ of 2.0 nM in the TGF-β1 concentration assay. Compound 25 has an $IC_{50}$ of 0.13 nM in the IL-6 concentration assay.

(Compound 26)

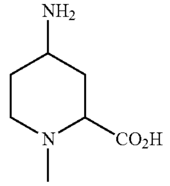

Compound 26, also known as 2-piperidinecarboxylic acid, 4-amino-1-methyl, inhibits human NEU3 with an $IC_{50}$ of <10 pM in the TGF-β1 concentration assay. Compound 26 has an $IC_{50}$ of 10 pM in the IL-6 concentration assay.

(Compound 27)

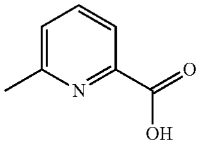

Compound 27, also known as 6-methyl-2-pyridinecarboxylic acid inhibits human NEU3 with an $IC_{50}$ of <10 pM in the TGF-β1 concentration assay. Compound 27 has an $IC_{50}$ of 4.1 nM in the IL-6 concentration assay.

Small molecule NEU3 inhibitors may also include compounds having the following structural formula:

(Compound 28)

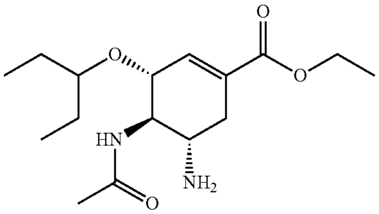

Compound 28, also known as oseltamivir, inhibits human NEU3 with an $IC_{50}$ of 570 nM in the TGF-β1 concentration assay. Compound 28 has an $IC_{50}$ of 47 μM in the IL-6 concentration assay.

Small molecule NEU3 inhibitors may also include compounds having the following structural formula:

(Compound 29)

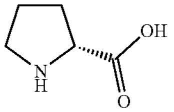

Compound 29, also known as D-proline, inhibits human NEU3 with an $IC_{50}$ of 63 nM in the TGF-β1 concentration assay. Compound 29 has an $IC_{50}$ of 4.2 μM in the IL-6 concentration assay.

Small molecule NEU3 inhibitors may also include compounds having the following structural formula:

(Compound 30)

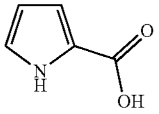

Compound 30, also known as pyrrole-2-carboxylic acid, inhibits human NEU3 with an $IC_{50}$ of 164 μM in the TGF-β1 concentration assay. Compound 30 has an $IC_{50}$ of 9.5 μM in the IL-6 concentration assay.

Small molecule NEU3 inhibitors may also include compounds having the following structural formula:

(Compound 31)

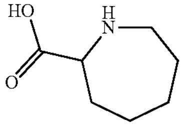

Compound 31, also known as azepane-2-carboxylic acid, inhibits human NEU3 with an $IC_{50}$ of 2.4 nM in the TGF-β1 concentration assay. Compound 31 has an $IC_{50}$ of 35 nM in the IL-6 concentration assay.

The present disclosure also provides a method of treating a fibrotic disorder, obesity, steatosis, liver inflammation, or cancer by administering a formulation comprising a compound of formula (I)

I

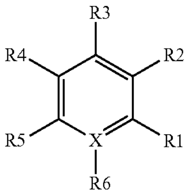

or its salt.

In formula I, $R_1$ may be selected from hydrogen, a halogen, an alkyl group, an aryl group, —$NH_2$, —$NH(C_{1-6}alkyl)$, —$N(C_{1-6}alkyl, C_{1-6}alkyl)$, —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —$CONH(C_{1-6}$alkyl or aryl), —$CON((C_{1-6}alkyl)_2$ or $(aryl)_2)$, —$(CH_2)_{1-3}NH_2$, —$SO_3H$, —$SO_2NH_2$, —$SO_2NH(C_{1-6}alkyl)$, —$SO_2N(C_{1-6}alkyl)_2$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}$ aryl), —$PO_3H(C_{1-6}alkyl)$, —$PO_3H(C_{1-6}aryl)$, a tetrazole or other heterocycle.

In formula I, $R_2$, $R_3$, and $R_4$ may be independently selected from hydrogen, a halogen, an alkyl group, an aryl group, —$NO_2$, —CN, —$CF_3$, —$NH_2$, —$NH(C_{1-6}alkyl)$, —$N(C_{1-6}alkyl, C_{1-6}alkyl)$, —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —$CONH(C_{1-6}$alkyl or aryl), —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, —$SO_2N(C_{1-6}aryl)_2$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}$ aryl), —$PO_3H(C_{1-6}alkyl)$, —$PO_3H(C_{1-6}aryl)$, tetrazole, 2-oxazolyl or other heterocycle.

In formula I, $R_5$ may be selected from hydrogen, a halogen, an alkyl group, an aryl group, —$CH_2OH$, hydroxypropyl, di-hydroxypropyl, tri-hydroxypropyl, —$NO_2$, —CN, —$CF_3$, —$NH_2$, —$NH(C_{1-6}alkyl)$, —$N(C_{1-6}alkyl, C_{1-6}alkyl)$, —$CONH_2$, —CONHOH, —OH, —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —$NHCO(C_{1-6}alkyl)$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula I, $R_6$ may be selected from hydrogen, methyl, —$CF_3$, $C_{1-6}$alkyl, aryl, —$CO(C_{1-6}alkyl)$, or nothing.

In formula I, X may be selected from carbon, oxygen, or nitrogen.

The present disclosure also provides a method of treating a fibrotic disorder, obesity, steatosis, liver inflammation, or cancer by administering a formulation comprising a compound of formula (II):

II

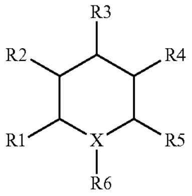

or its salt, wherein:

In formula II, $R_1$ may be selected from hydrogen, a halogen, an alkyl group, an aryl group, —$NH_2$, —$NH(C_{1-6}alkyl)$, —$N(C_{1-6}alkyl, C_{1-6}alkyl)$, —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —$CONH(C_{1-6}$alkyl or aryl), —$CON((C_{1-6}alkyl)_2$ or $(aryl)_2)$, —$(CH_2)_{1-3}NH_2$, —$SO_3H$, —$SO_2NH_2$, —$SO_2NH(C_{1-6}alkyl)$, —$SO_2N(C_{1-6}alkyl)_2$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}$ aryl), —$PO_3H(C_{1-6}alkyl)$, —$PO_3H(C_{1-6}aryl)$, a tetrazole or other heterocycle.

In formula II, $R_2$, $R_3$, and $R_4$ may be independently selected from hydrogen, a halogen, an alkyl group, an aryl group, —$NO_2$, —CN, —$CF_3$, —$NH_2$, —$NH(C_{1-6}alkyl)$, —$N(C_{1-6}alkyl, C_{1-6}alkyl)$, —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —$CONH(C_{1-6}$alkyl or aryl), —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, —$SO_2N(C_{1-6}aryl)_2$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula II, $R_5$ may be selected from hydrogen, a halogen, an alkyl group, an aryl group, —$CH_2OH$, hydroxypropyl, di-hydroxypropyl, tri-hydroxypropyl, —$NO_2$, —CN, —$CF_3$, —$NH_2$, —$NH(C_{1-6}alkyl)$, —$N(C_{1-6}alkyl, C_{1-6}alkyl)$, —$CONH_2$, —CONHOH, —OH, —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —$NHCO(C_{1-6}alkyl)$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula II, $R_6$ may be selected from hydrogen, methyl, —$CF_3$, $C_{1-6}$alkyl, aryl, —$CO(C_{1-6}alkyl)$, or nothing.

In formula II, X may be selected from carbon, nitrogen, or oxygen.

The present disclosure also provides a method of treating a fibrotic disorder, obesity, steatosis, liver inflammation, or cancer by administering a formulation comprising a compound of formula (III):

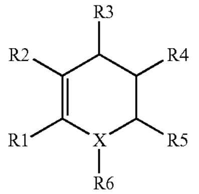

III or its salt, wherein:

In formula III, $R_1$ may be selected from hydrogen, a halogen, an alkyl group, an aryl group, —$NH_2$, —$NH(C_{1-6}alkyl)$, —$N(C_{1-6}alkyl, C_{1-6}alkyl)$, —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —$CONH(C_{1-6}alkyl$ or aryl), —$CON((C_{1-6}alkyl)_2$ or $(aryl)_2)$, —$(CH_2)_{1-3}NH_2$, —$SO_3H$, —$SO_2NH_2$, —$SO_2NH(C_{1-6}alkyl)$, —$SO_2N(C_{1-6}alkyl)_2$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, a tetrazole or other heterocycle.

In formula III, $R_2$, $R_3$, and $R_4$ may be independently selected from hydrogen, a halogen, an alkyl group, an aryl group, —$NO_2$, —CN, —$CF_3$, —$NH_2$, —$NH(C_{1-6}alkyl)$, —$N(C_{1-6}alkyl, C_{1-6}alkyl)$, —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —$CONH(C_{1-6}alkyl$ or aryl), —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, —$SO_2N(C_{1-6}aryl)_2$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula III, $R_5$ may be selected from hydrogen, a halogen, an alkyl group, an aryl group, —$CH_2OH$, hydroxypropyl, di-hydroxypropyl, tri-hydroxypropyl, —$NO_2$, —CN, —$CF_3$, —$NH_2$, —$NH(C_{1-6}alkyl)$, —$N(C_{1-6}alkyl, C_{1-6}alkyl)$, —$CONH_2$, —CONHOH, —OH, —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, $C_{1-6}$alkyl, aryl, $C_{1-6}$alkyl ester, aryl ester —$(CH_2)_{1-3}NH_2$, —COOH, —$NHCO(C_{1-6}alkyl)$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula III, $R_6$ may be selected from hydrogen, methyl, —$CF_3$, $C_{1-6}$alkyl, aryl, —$CO(C_{1-6}alkyl)$, or nothing.

In formula III, X may be selected from carbon, oxygen, or nitrogen.

The present disclosure also provides a method of treating a fibrotic disorder, obesity, steatosis, liver inflammation, or cancer by administering a formulation comprising a compound of formula (IV):

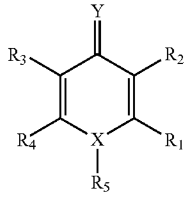

(IV)

or its salt, wherein:

In formula IV, $R_1$ may be selected from hydrogen, a halogen, an alkyl group, an aryl group, —$NH_2$, —$NH(C_{1-6}alkyl)$, —$N(C_{1-6}alkyl, C_{1-6}alkyl)$, —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —$CONH(C_{1-6}alkyl$ or aryl), —$CON((C_{1-6}alkyl)_2$ or $(aryl)_2)$, —$(CH_2)_{1-3}NH_2$, —$SO_3H$, —$SO_2NH_2$, —$SO_2NH(C_{1-6}alkyl)$, —$SO_2N(C_{1-6}alkyl)_2$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, a tetrazole or other heterocycle.

In formula IV, $R_2$, $R_3$, and $R_4$ may be independently selected from hydrogen, a halogen, an alkyl group, an aryl group, —$NO_2$, —CN, —$CF_3$, —$NH_2$, —$NH(C_{1-6}alkyl)$, —$N(C_{1-6}alkyl, C_{1-6}alkyl)$, —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —$CONH(C_{1-6}alkyl$ or aryl), —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, —$SO_2N(C_{1-6}aryl)_2$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula IV, $R_5$ may be selected from hydrogen, methyl, —$CF_3$, $C_{1-6}$alkyl, aryl, —$CO(C_{1-6}alkyl)$, or nothing.

In formula IV, X may be selected from carbon, oxygen, or nitrogen.

In formula IV, Y may be selected from oxygen, a hydroxyl group, a di-methyl nitrogen, or a methylene group.

The present disclosure provides a method of treating a fibrotic disorder, obesity, steatosis, liver inflammation, or cancer by administrating a formulation comprising a compound of formula (V):

V

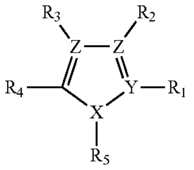

or its salt, wherein:

In formula V $R_1$ may be selected from hydrogen, a halogen, an alkyl group, an aryl group, —$NH_2$, —$NH(C_{1-6}alkyl)$, —$N(C_{1-6}alkyl, C_{1-6}alkyl)$, —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —$CONH(C_{1-6}$alkyl or aryl), —$CON((C_{1-6}alkyl)_2$ or $(aryl)_2)$, —$(CH_2)_{1-3}NH_2$, —$SO_3H$, —$SO_2NH_2$, —$SO_2NH(C_{1-6}alkyl)$, —$SO_2N(C_{1-6}alkyl)_2$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, a tetrazole or other heterocycle.

In formula V, $R_2$ and $R_3$, may be independently selected from hydrogen, a halogen, an alkyl group, an aryl group, —$NO_2$, —CN, —$CF_3$, —$NH_2$, —$NH(C_{1-6}alkyl)$, —$N(C_{1-6}alkyl, C_{1-6}alkyl)$, —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —$CONH(C_{1-6}$alkyl or aryl), —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, —$SO_2N(C_{1-6}aryl)_2$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula V, $R_4$ may be selected from hydrogen, a halogen, an alkyl group, an aryl group, —$CH_2OH$, hydroxypropyl, di-hydroxypropyl, tri-hydroxypropyl, —$NO_2$, —CN, —$CF_3$, —$NH_2$, —$NH(C_{1-6}alkyl)$, —$N(C_{1-6}alkyl, C_{1-6}alkyl)$, —$CONH_2$, —CONHOH, —OH, —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —$NHCO(C_{1-6}alkyl)$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula V, $R_5$ may be selected from hydrogen, methyl, —$CF_3$, $C_{1-6}$alkyl, aryl, —$CO(C_{1-6}alkyl)$, or nothing.

In formula V, X may be selected from carbon, oxygen, or nitrogen.

In formula V, Y may be selected from carbon or nitrogen.

In formula V, Z may be selected from carbon, nitrogen, oxygen, or sulfur.

The present disclosure provides a method of treating a fibrotic disorder, obesity, steatosis, liver inflammation, or cancer by administrating a formulation comprising a compound of formula (VI):

VI

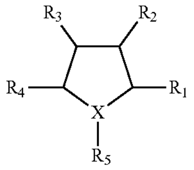

or its salt, wherein:

In formula VI, $R_1$ may be selected from hydrogen, a halogen, an alkyl group, an aryl group, —$NH_2$, —$NH(C_{1-6}alkyl)$, —$N(C_{1-6}alkyl, C_{1-6}alkyl)$, —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —$CONH(C_{1-6}$alkyl or aryl), —$CON((C_{1-6}alkyl)_2$ or $(aryl)_2)$, —$(CH_2)_{1-3}NH_2$, —$SO_3H$, —$SO_2NH_2$, —$SO_2NH(C_{1-6}alkyl)$, —$SO_2N(C_{1-6}alkyl)_2$, —$SO_2NH(C_{1-6}aryl)$, —$SO_2N(C_{1-6}aryl)_2$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, a tetrazole or other heterocycle.

In formula VI, $R_2$ and $R_3$, may be independently selected from hydrogen, a halogen, an alkyl group, an aryl group, —$NO_2$, —CN, —$CF_3$, —$NH_2$, —$NH(C_{1-6}alkyl)$, —$N(C_{1-6}alkyl, C_{1-6}alkyl)$, —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —$CONH(C_{1-6}$alkyl or aryl), —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, —$SO_2N(C_{1-6}aryl)_2$, —$COCH_3$, $C_{2-5}$acyl, —CO(aryl), —$SO_3H$, —$SO_2NH_2$, —$SO_2NH(C_{1-6}alkyl)$, —$SO_2NH(C_{1-6}aryl)$, —$SO_3(C_{1-6}alkyl)$, —$SO_3(C_{1-6}aryl)$, —$PO_3H_2$, —$PO_2H_2$, —$PO_2NH(C_{1-6}alkyl)$, —$PO_2NH(C_{1-6}aryl)$, —$PO_2H(C_{1-6}alkyl)$, —$PO_2H(C_{1-6}aryl)$, —$PO_3H(C_{1-6}alkyl)$, —$PO_3H(C_{1-6}aryl)$, tetrazole, 2-oxazolyl or other heterocycle.

In formula VI, $R_4$ may be selected from hydrogen, a halogen, an alkyl group, an aryl group, —$CH_2OH$, hydroxypropyl, di-hydroxypropyl, tri-hydroxypropyl, —$NO_2$, —CN, —$CF_3$, —$NH_2$, —$NH(C_{1-6}alkyl)$, —$N(C_{1-6}alkyl, C_{1-6}alkyl)$, —$CONH_2$, —CONHOH, —OH, —$CON((C_{1-6}alkyl)_2$ or $(aryl)_2)$, —$CH(OH)CH_3$, —$CH(OH)(CH_2OH)$, —$CH(OH)(CH(OH)CH_2OH)$, —$NHCO(C_{1-6}alkyl)$, $C_{1-6}$alkyl ether, an aryl ether, —$(CH_2)_{1-3}NH_2$, $C_{1-6}$alkyl, aryl, $C_{1-6}$alkyl ester, aryl ester, —$(CH_2)_{1-3}NH_2$, —COOH, —$NHCO(C_{1-6}alkyl)$, —$COCH_3$, $C_{2-5}$acyl, —CO (aryl), $—SO_3H$, $—SO_2NH_2$, $—SO_2NH(C_{1-6}alkyl)$, $—SO_2NH(C_{1-6}aryl)$, $—SO_2N(C_{1-6}aryl)_2$, $—SO_3(C_{1-6}alkyl)$, $—SO_3(C_{1-6}aryl)$, $—PO_3H_2$, $—PO_2H_2$, $—PO_2NH(C_{1-6}alkyl)$, $—PO_2NH(C_{1-6}aryl)$, $—PO_2H(C_{1-6}alkyl)$, $—PO_2H(C_{1-6}aryl)$, $—PO_3H(C_{1-6}alkyl)$, $—PO_3H(C_{1-6}aryl)$, tetrazole, 2-oxazolyl or other heterocycle.

In formula VI, $R_5$ may be selected from hydrogen, methyl, $—CF_3$, $C_{1-6}alkyl$, aryl, $—CO(C_{1-6}alkyl)$, or nothing.

In formula VI, X may be selected from carbon, oxygen, or nitrogen.

The present disclosure provides a method of treating a fibrotic disorder obesity, steatosis, liver inflammation, or cancer by administrating a formulation comprising a compound of formula (VII):

VII

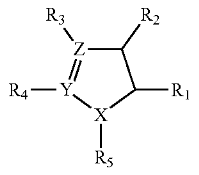

or its salt, wherein:

In for In formula VII, $R_1$ may be selected from hydrogen, a halogen, an alkyl group, an aryl group, $—NH_2$, $—NH(C_{1-6}alkyl)$, $—N(C_{1-6}alkyl, C_{1-6}alkyl)$, —C(O)—NHOH, $—NO_2$, —OH, —O-alkyl, —O-aryl, —CN, —COOH, $—CONH_2$, —CHO, $—COCH_3$, —CO(alkyl), —CO(aryl), $—COCF_3$, $—COCHF_2$, $—CO_2$-alkyl, $—CO_2$-aryl, $—CONH(C_{1-6}alkyl$ or aryl), $—CON((C_{1-6}alkyl)_2$ or $(aryl)_2)$, $—(CH_2)_{1-3}NH_2$, $—SO_3H$, $—SO_2NH_2$, $—SO_2NH(C_{1-6}alkyl)$, $—SO_2N(C_{1-6}alkyl)_2$, $—SO_2NH(C_{1-6}aryl)$, $—SO_2N(C_{1-6}aryl)_2$, $—SO_3(C_{1-6}alkyl)$, $—SO_3(C_{1-6}aryl)$, $—PO_3H_2$, $—PO_2H_2$, $—PO_2NH(C_{1-6}alkyl)$, $—PO_2NH(C_{1-6}aryl)$, $—PO_2H(C_{1-6}alkyl)$, $—PO_2H(C_{1-6}aryl)$, $—PO_3H(C_{1-6}alkyl)$, $—PO_3H(C_{1-6}aryl)$, a tetrazole or other heterocycle.

In formula VII, $R_2$ and $R_3$, may be independently selected from hydrogen, a halogen, an alkyl group, an aryl group, $—NO_2$, —CN, $—CF_3$, $—NH_2$, $—NH(C_{1-6}alkyl)$, $—N(C_{1-6}alkyl, C_{1-6}alkyl)$, $—CONH_2$, —C(O)—NHOH, —OH, $C_{1-6}alkyl$, aryl, —COOH, $—CONH_2$, $—COCH_3$, $—COCF_3$, $—COCHF_2$, $—CO_2$-aryl, $—CONH(C_{1-6}alkyl$ or aryl), $—CON((C_{1-6}alkyl)_2$ or $(aryl)_2)$, $—CH(OH)CH_3$, $—CH(OH)(CH_2OH)$, $—CH(OH)(CH(OH)CH_2OH)$, $—NHCO(C_{1-6}alkyl)$, $C_{1-6}alkyl$ ether, an aryl ether, $—(CH_2)_{1-3}NH_2$, $—SO_2N(C_{1-6}aryl)_2$, $—COCH_3$, $C_{2-5}acyl$, —CO(aryl), $—SO_3H$, $—SO_2NH_2$, $—SO_2NH(C_{1-6}alkyl)$, $—SO_2NH(C_{1-6}aryl)$, $—SO_3(C_{1-6}alkyl)$, $—SO_3(C_{1-6}aryl)$, $—PO_3H_2$, $—PO_2H_2$, $—PO_2NH(C_{1-6}alkyl)$, $—PO_2NH(C_{1-6}aryl)$, $—PO_2H(C_{1-6}alkyl)$, $—PO_2H(C_{1-6}aryl)$, $—PO_3H(C_{1-6}alkyl)$, $—PO_3H(C_{1-6}aryl)$, tetrazole, 2-oxazolyl or other heterocycle.

In formula VII, $R_4$ may be selected from hydrogen, a halogen, an alkyl group, an aryl group, $—CH_2OH$, hydroxypropyl, di-hydroxypropyl, tri-hydroxypropyl, $—NO_2$, —CN, $—CF_3$, $—NH_2$, $—NH(C_{1-6}alkyl)$, $—N(C_{1-6}alkyl, C_{1-6}alkyl)$, $—CONH_2$, —CONHOH, —OH, $—CON((C_{1-6}alkyl)_2$ or $(aryl)_2)$, $—CH(OH)CH_3$, $—CH(OH)(CH_2OH)$, $—CH(OH)(CH(OH)CH_2OH)$, $—NHCO(C_{1-6}alkyl)$, $C_{1-6}alkyl$ ether, an aryl ether, $—(CH_2)_{1-3}NH_2$, $C_{1-6}alkyl$, aryl, $C_{1-6}alkyl$ ester, aryl ester, $—(CH_2)_{1-3}NH_2$, —COOH, $—NHCO(C_{1-6}alkyl)$, $—COCH_3$, $C_{2-5}acyl$, —CO(aryl), $—SO_3H$, $—SO_2NH_2$, $—SO_2NH(C_{1-6}alkyl)$, $—SO_2NH(C_{1-6}aryl)$, $—SO_2N(C_{1-6}aryl)_2$, $—SO_3(C_{1-6}alkyl)$, $—SO_3(C_{1-6}aryl)$, $—PO_3H_2$, $—PO_2H_2$, $—PO_2NH(C_{1-6}alkyl)$, $—PO_2NH(C_{1-6}aryl)$, $—PO_2H(C_{1-6}alkyl)$, $—PO_2H(C_{1-6}aryl)$, $—PO_3H(C_{1-6}alkyl)$, $—PO_3H(C_{1-6}aryl)$, tetrazole, 2-oxazolyl or other heterocycle.

In formula VIII, $R_5$ may be selected from hydrogen, methyl, $—CF_3$, $C_{1-6}alkyl$, aryl, $—CO(C_{1-6}alkyl)$, or nothing.

In formula VIII, X may be selected from carbon, oxygen, or nitrogen.

In formula VII, Y may be selected from carbon or nitrogen.

In formula VII, Z may be selected from carbon, nitrogen, oxygen, or sulfur.

The present disclosure also provides a method of treating a fibrotic disorder, obesity, steatosis, liver inflammation, or cancer by administrating a formulation comprising a compound of formula (VIII):

VIII

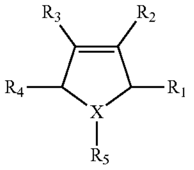

or its salt, wherein:

In formula VIII, $R_1$ may be selected from hydrogen, a halogen, an alkyl group, an aryl group, $—NH_2$, $—NH(C_{1-6}alkyl)$, $—N(C_{1-6}alkyl, C_{1-6}alkyl)$, —C(O)—NHOH, $—NO_2$, —OH, —O-alkyl, —O-aryl, —CN, —COOH, $—CONH_2$, —CHO, $—COCH_3$, —CO(alkyl), —CO(aryl), $—COCF_3$, $—COCHF_2$, $—CO_2$-alkyl, $—CO_2$-aryl, $—CONH(C_{1-6}alkyl$ or aryl), $—CON((C_{1-6}alkyl)_2$ or $(aryl)_2)$, $—(CH_2)_{1-3}NH_2$, $—SO_3H$, $—SO_2NH_2$, $—SO_2NH(C_{1-6}alkyl)$, $—SO_2N(C_{1-6}alkyl)_2$, $—SO_2NH(C_{1-6}aryl)$, $—SO_2N(C_{1-6}aryl)_2$, $—SO_3(C_{1-6}alkyl)$, $—SO_3(C_{1-6}aryl)$, $—PO_3H_2$, $—PO_2H_2$, $—PO_2NH(C_{1-6}alkyl)$, $—PO_2NH(C_{1-6}aryl)$, $—PO_2H(C_{1-6}alkyl)$, $—PO_2H(C_{1-6}aryl)$, $—PO_3H(C_{1-6}alkyl)$, $—PO_3H(C_{1-6}aryl)$, a tetrazole or other heterocycle.

In formula VIII, $R_2$ and $R_3$, may be independently selected from hydrogen, a halogen, an alkyl group, an aryl group, $—NO_2$, —CN, $—CF_3$, $—NH_2$, $—NH(C_{1-6}alkyl)$, $—N(C_{1-6}alkyl, C_{1-6}alkyl)$, $—CONH_2$, —C(O)—NHOH, —OH, $C_{1-6}alkyl$, aryl, —COOH, $—CONH_2$, $—COCH_3$, $—COCF_3$, $—COCHF_2$, $—CO_2$-aryl, $—CONH(C_{1-6}alkyl$ or aryl), $—CON((C_{1-6}alkyl)_2$ or $(aryl)_2)$, $—CH(OH)CH_3$, $—CH(OH)(CH_2OH)$, $—CH(OH)(CH(OH)CH_2OH)$, $—NHCO(C_{1-6}alkyl)$, $C_{1-6}alkyl$ ether, an aryl ether, $—(CH_2)_{1-3}NH_2$, $—SO_2N(C_{1-6}aryl)_2$, $—COCH_3$, $C_{2-5}acyl$, —CO(aryl), $—SO_3H$, $—SO_2NH_2$, $—SO_2NH(C_{1-6}alkyl)$, $—SO_2NH(C_{1-6}aryl)$, $—SO_3(C_{1-6}alkyl)$, $—SO_3(C_{1-6}aryl)$, $—PO_3H_2$, $—PO_2H_2$, $—PO_2NH(C_{1-6}alkyl)$, $—PO_2NH(C_{1-6}aryl)$, $—PO_2H(C_{1-6}alkyl)$, $—PO_2H(C_{1-6}aryl)$, $—PO_3H(C_{1-6}alkyl)$, $—PO_3H(C_{1-6}aryl)$, tetrazole, 2-oxazolyl or other heterocycle.

In formula VIII, $R_4$ may be selected from hydrogen, a halogen, an alkyl group, an aryl group, $—CH_2OH$, hydroxypropyl, di-hydroxypropyl, tri-hydroxypropyl, $—NO_2$, —CN, $—CF_3$, $—NH_2$, $—NH(C_{1-6}alkyl)$, $—N(C_{1-6}alkyl, C_{1-6}alkyl)$, $—CONH_2$, —CONHOH, —OH, $—CON((C_{1-6}alkyl)_2$ or $(aryl)_2)$, $—CH(OH)CH_3$, $—CH(OH)(CH_2OH)$, $—CH(OH)(CH(OH)CH_2OH)$, $—NHCO(C_{1-6}alkyl)$, $C_{1-6}alkyl$ ether, an aryl ether, $—(CH_2)_{1-3}NH_2$, $C_{1-6}$alkyl, aryl, $C_{1-6}$alkyl ester, aryl ester, —$(CH_2)_{1-3}NH_2$, —COOH, —NHCO($C_{1-6}$alkyl), —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$aryl), —$PO_3H$($C_{1-6}$alkyl), —$PO_3H$($C_{1-6}$aryl), tetrazole, 2-oxazolyl or other heterocycle.

In formula VIII, $R_5$ may be selected from hydrogen, methyl, —$CF_3$, $C_{1-6}$alkyl, aryl, —CO($C_{1-6}$alkyl), or nothing.

In formula VIII, X may be selected from carbon, oxygen, or nitrogen.

The present disclosure also provides a method of treating a fibrotic disorder, obesity, steatosis, liver inflammation, or cancer by administrating a formulation comprising a compound of formula (IX):

IX

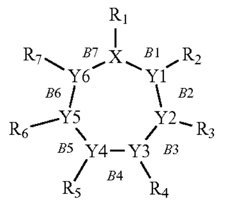

or its salt.

In formula IX, B1, B2, B3, B4, B5, B6, and/or B7 may be selected from a single or double (olefin) bonds;

In formula IX, $R_1$ may be selected from hydrogen, methyl, —$CF_3$, $C_{1-6}$alkyl, aryl, —CO($C_{1-6}$alkyl), or nothing.

In formula IX, $R_2$-$R_6$ may be selected from hydrogen, a halogen, an alkyl group, an aryl group, —$NH_2$, —NH($C_{1-6}$alkyl), —N($C_{1-6}$alkyl, $C_{1-6}$alkyl), —C(O)—NHOH, —$NO_2$, —OH, —O-alkyl, —O-aryl, —CN, —COOH, —$CONH_2$, —CHO, —$COCH_3$, —CO(alkyl), —CO(aryl), —$COCF_3$, —$COCHF_2$, —$CO_2$-alkyl, —$CO_2$-aryl, —CONH($C_{1-6}$alkyl or aryl), —CON(($C_{1-6}$alkyl)$_2$ or (aryl)$_2$), —$(CH_2)_{1-3}NH_2$, —$SO_3H$, —$SO_2NH_2$, —$SO_2NH$($C_{1-6}$alkyl), —$SO_2N$($C_{1-6}$alkyl)$_2$, —$SO_2NH$($C_{1-6}$aryl), —$SO_2N$($C_{1-6}$aryl)$_2$, —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$ aryl), —$PO_3H$($C_{1-6}$alkyl), —$PO_3H$($C_{1-6}$aryl), a tetrazole or other heterocycle.

In formula IX, $R_7$ may be independently selected from hydrogen, a halogen, an alkyl group, an aryl group, —$NO_2$, —CN, —$CF_3$, —$NH_2$, —NH($C_{1-6}$alkyl), —N($C_{1-6}$alkyl, $C_{1-6}$alkyl), —$CONH_2$, —C(O)—NHOH, —OH, $C_{1-6}$alkyl, aryl, —COOH, —$CONH_2$, —$COCH_3$, —$COCF_3$, —$COCHF_2$, —$CO_2$-aryl, —CONH($C_{1-6}$alkyl or aryl), —CON(($C_{1-6}$alkyl)$_2$ or (aryl)$_2$), —CH(OH)$CH_3$, —CH(OH)($CH_2$OH), —CH(OH)(CH(OH)$CH_2$OH), —NHCO($C_{1-6}$ alkyl), $C_{1-6}$alkyl ether, an aryl ether, —$(CH_2)_{1-3}NH_2$, —$SO_2N$($C_{1-6}$aryl)$_2$, —$COCH_3$, $C_{2-5}$acyl, —CO(aryl), —$SO_3H$, —$SO_2NH_2$, —$SO_2NH$($C_{1-6}$alkyl), —$SO_2NH$($C_{1-6}$aryl), —$SO_3$($C_{1-6}$alkyl), —$SO_3$($C_{1-6}$aryl), —$PO_3H_2$, —$PO_2H_2$, —$PO_2NH$($C_{1-6}$alkyl), —$PO_2NH$($C_{1-6}$aryl), —$PO_2H$($C_{1-6}$alkyl), —$PO_2H$($C_{1-6}$ aryl), —$PO_3H$($C_{1-6}$alkyl), —$PO_3H$($C_{1-6}$aryl), tetrazole, 2-oxazolyl or other heterocycle.

In formula IX, X may be selected from carbon, oxygen, or nitrogen.

In formula IX, Y may be selected from carbon, nitrogen, oxygen, or sulfur.

The above methods may be combined with one another and alone or in combination may further include one or more of the following additional features, unless clearly mutually exclusive:

i. the method may inhibit desialylation of LAP;
ii. the method may inhibit the extracellular accumulation of IL-6;
iii. the method may inhibit desialylation of SAP;
iv. the method may inhibit the formation or activation of fibrocytes;
v. the method may decrease the level or activity of TGF-β1;
vi. the method may decrease the level or activity of a sialidase in a human;
vii. the method may inhibit more than one sialidase;
viii. the compound may be administered to a human locally in an area in which human sialidase activity is abnormally high;
ix. the formulation may be administered via intravenous or intraperitoneal injection, orally, topically, via inhalation, or via other means of enteral or parenteral administration;
x. the compound used in the method is DANA;
xi. the compound used in the method is 4-hydroxypyridine-2-carboxylic acid;
xii. the compound used in the method is 5-acetamidopyridine-2-carboxylic acid;
xiii. the compound used in the method is picolinic acid;
xiv. the compound used in the method is 2-acetylpyridine;
xv. the compound used in the method is methyl picolinate;
xvi. the compound used in the method is 4-amino picolinic acid;
xvii. the compound used in the method is 5-nitro picolinic acid;
xviii. the compound used in the method is 4-methoxy picolinic acid;
xix. the compound used in the method is picolinamide;
xx. the compound used in the method is 5-acetylamino-4-amino picolinic acid;
xxi. the compound used in the method is 1,4,5,6-tetrahydropyridine-2-carboxylate;
xxii. the compound used in the method is L-pipecolinic acid;
xxiii. the compound used in the method is nicotinic acid;
xxiv. the compound used in the method is salicylic acid;
xxv. the compound used in the method is O-(tetrahydro-2H-pyran-2-yl)-hydroxylamine;
xxvi. the compound used in the method is 6-(hydroxymethyl) picolinic acid;
xxvii. the compound used in the method is 5-aminopyridine-2-carboxylic acid;
xxviii. the compound used in the method is 2-Nitropyridine;
xxix. the compound used in the method is 1-methyl-2-piperidine carboxylic acid;
xxx. the compound used in the method is 4-(triflurommethyl) picolinic acid;
xxxi. the compound used in the method is 4-methylpicolinic acid;
xxxii. the compound used in the method is 4-aminonicotinic acid;
xxxiii. the compound used in the method is 4-oxo-1,4-dihydropyridine-2-carboxylic acid;
xxxiv. the compound used in the method is 2-piperidinecarboxylic acid, 4-amino;
xxxv. the compound used in the method is 2-piperidinecarboxylic acid, 4-amino-1-methyl;

xxxvi. the compound used in the method is 2-pyridinecarboxylic acid, 6-methyl;

xxxvii. the compound used in the method is oseltamivir;

xxxviii. the compound used in the method is D-proline;

xxxix. the compound used in the method is pyrrole-2-carboxylic acid;

xl. the compound used in the method is azepane-2-carboxylic acid, and;

xli. the dose administered may be sufficient to establish a systemic concentration or a concentration in the area of administration of at least 3 μM. Dosing may be daily for at least one week, at least two weeks, at least three weeks, or indefinitely;

xlii. the dose administered may be sufficient to establish a systemic concentration or a concentration in the area of administration of at least 0.6 μM. Dosing may be daily for at least one week, at least two weeks, at least three weeks, or indefinitely;

xliii. the dose administered may be sufficient to decrease fibrosis in a human;

xliv. the dose administered may be sufficient to decrease fibrosis in an animal;

xlv. the dose administered may be sufficient to decrease tumor growth in a human;

xlvi. the dose administered may be sufficient to decrease tumor growth in an animal;

xlvii. the dose administered may be sufficient to inhibit cancer in a human;

xlviii. the dose administered may be sufficient to inhibit cancer in an animal;

xlix. the dose administered may be sufficient to inhibit liver inflammation in a human;

l. the dose administered may be sufficient to inhibit liver inflammation in an animal;

li. the dose administered may be sufficient to inhibit weight gain in a human;

lii. the dose administered may be sufficient to decrease the amount of neutral lipids in the liver of an animal;

liii. the dose administered may be sufficient to decrease the level of activity of a sialidase in an animal, liv. the dose administered may be sufficient to decrease the amount of neutral lipids in the liver of a human; and lv. the dose administered may be sufficient to decrease the level of activity of a sialidase in a human.

Fibrosing Diseases

NEU3 inhibitors may be used to prevent or inhibit fibrosis in any of a number of fibrosing diseases in a mammal, particularly in a human.

For example, they may prevent or inhibit fibrosis occurring in the liver, gall bladder, kidney, lung, upper respiratory tract including but not limited to the nose, esophagus, and larynx, heart and pericardium, blood or lymphatic vessels, lymph nodes, eye, skin, mouth, pancreas, gastrointestinal tract, brain, spinal cord, breast, bone marrow, bone and joints, genitourinary system, thyroid, parathyroid or adrenal gland, musculoskeletal system, a tumor, including a cancerous tumor, or a wound.

Generally, they may prevent or inhibit fibrosis resulting from conditions including but not limited to rheumatoid arthritis, lupus, psoriatic arthritis, ankylosing spondylitis, pathogenic fibrosis, fibrosing disease, fibrotic lesions such as those formed after *Schistosoma japonicum* infection, radiation damage, autoimmune diseases, Lyme disease, chemotherapy induced fibrosis, HIV or infection-induced focal sclerosis, failed back syndrome due to spinal surgery scarring, abdominal adhesion post-surgery scarring, fibrocystic formations, fibrosis after spinal injury, surgery-induced fibrosis, mucosal fibrosis, peritoneal fibrosis caused by dialysis, tumor-associated fibrosis, and anti-TNF-associated pulmonary fibrosis.

Specifically, in the liver, they may prevent or inhibit fibrosis resulting from conditions including but not limited to alcohol, drug, and/or chemically induced cirrhosis, ischemia-reperfusion injury after hepatic transplant, necrotizing hepatitis, hepatitis B, hepatitis C, hepatitis D, hepatitis E, other virally-induced hepatitis, hepatitis caused by bacterial or parasitic infections, primary biliary cirrhosis, primary sclerosing cholangitis, steatosis, autoimmune hepatitis such as but not limited to auto antibody driven hepatitis, or hepatitis caused by genetic conditions such as alpha-1-antitrypsin deficiency, and Wilson's disease.

Relating to the gall bladder, they may prevent or inhibit fibrosis resulting from conditions including but not limited to fibrosis associated with chronic cholecystitis.

Relating to the kidney, they may prevent or inhibit fibrosis resulting from conditions including but not limited to proliferative and sclerosing glomerulonephritis, nephrogenic fibrosing dermopathy, diabetic nephropathy, Lupus nephritis, renal tubulointerstitial fibrosis, focal segmental glomerulosclerosis, and fibrosis caused by kidney or urinary tract infections.

Relating to the lung and respiratory tract including but not limited to the nose, esophagus, and larynx, they may prevent or inhibit fibrosis resulting from conditions including but not limited to pulmonary interstitial fibrosis, sarcoidosis, pulmonary fibrosis, idiopathic pulmonary fibrosis, asthma, chronic obstructive pulmonary disease, diffuse alveolar damage disease, pulmonary hypertension, neonatal bronchopulmonary dysplasia, chronic asthma, eosinophilic esophagitis, laryngeal fibrosis, and emphysema. There are several sub-names or synonyms for pulmonary fibrosis including, but not limited to, cryptogenic fibrosing alveolitis, diffuse interstitial fibrosis, idiopathic interstitial pneumonitis, Hamman-Rich syndrome, silicosis, asbestosis, berylliosis, coal worker's pneumoconiosis, black lung disease, coal miner's disease, miner's asthma, anthracosis, and anthracosilicosis.

Relating to the heart and/or pericardium, they may prevent or inhibit fibrosis resulting from conditions including but not limited to myocardial fibrosis, atherosclerosis, coronary artery restenosis, congestive cardiomyopathy, dilated cardiomyopathy, heart failure, and other post-ischemic conditions.

Relating to the lymphatic system, they may prevent or inhibit fibrosis resulting from conditions including but not limited to fibrosis associated with chronic Lymphedema, Lymphostatic fibrosis, fibrosis linked to autoimmune diseases, cancer, or infections.

Relating to the eye, they may prevent or inhibit fibrosis resulting from conditions including but not limited to exophthalmos of Grave's disease, proliferative vitreoretinopathy, anterior capsule cataract, corneal fibrosis, corneal scarring due to surgery, trabeculectomy-induced fibrosis, progressive subretinal fibrosis, multifocal granulomatous chorioretinitis, and other eye fibrosis.

Relating to the skin, they may prevent or inhibit fibrosis resulting from conditions including but not limited to Dupuytren's contracture, scleroderma, keloid scarring, psoriasis, hypertrophic scarring due to burns, atherosclerosis, restenosis, and psuedoscleroderma caused by spinal cord injury.

Relating to the mouth and/or esophagus, they may prevent or inhibit fibrosis resulting from conditions including but not limited to periodontal disease scarring, gingival hypertrophy secondary to drugs, and congenital esophageal stenosis.

Relating to the pancreas, they may prevent or inhibit fibrosis resulting from conditions including but not limited to pancreatic fibrosis, stromal remodeling pancreatitis, and stromal fibrosis.

Relating to the gastrointestinal tract, they may prevent or inhibit fibrosis resulting from conditions including but not limited to collagenous colitis, villous atrophy, crypt hyperplasia, polyp formation, fibrosis of Crohn's disease, and healing gastric ulcer.

Relating to the brain, they may prevent or inhibit fibrosis resulting from conditions including but not limited to glial scar tissue. Relating to the breast, they may prevent or inhibit fibrosis resulting from conditions including but not limited to fibrocystic disease and desmoplastic reaction to breast cancer.

Relating to the bone marrow, they may prevent or inhibit fibrosis resulting from conditions including but not limited to fibrosis in myelofibrosis, myelodysplasia, and neoplastic diseases.

Relating to the bone, they may prevent or inhibit fibrosis resulting from conditions including but not limited to rheumatoid arthritis, systemic lupus erythematosus (SLE), psoriatic arthritis, ankylosing spondylitis, and rheumatoid pannus formation.

Relating to the genitourinary system, they may prevent or inhibit fibrosis resulting from conditions including but not limited to endometriosis, uterine fibroids, ovarian fibroids, and Peyronie's disease.

Relating to the thyroid and parathyroid, they may prevent or inhibit fibrosis resulting from conditions including but not limited to fibrosis associated with hyperparathyroidism, hypoparathyroidism, chronic thyroiditis, Riedel thyroiditis, chronic lymphocytic thyroiditis (Hashimoto's thyroiditis), and acute infectious thyroiditis.

Relating to the musculoskeletal system, they may prevent or inhibit fibrosis resulting from conditions including but not limited to fibrosis associated with musculoskeletal disorders such as carpal tunnel syndrome, muscle or ligament or other connective tissue damage following injury, autoimmunity, or infection, or muscle fibrosis associated with muscular dystrophies such as Duchenne muscular dystrophy, and aging.

Relating to radiation-induced damage, they may prevent or inhibit fibrosis related to, but not limited to, treatment of head and neck cancer, ovarian cancer, prostate cancer, lung cancer, gastrointestinal cancer, colon cancer, and breast cancer.

EXAMPLES

The following examples illustrate aspects of the invention; no example is intended to encompass the invention as a whole. Furthermore, although some examples may present discrete embodiments of the invention, aspects of such examples may be combined with other variations of the invention as described above or in different examples unless such combinations would be clearly inoperable to one of skill in the art.

Unless otherwise specified, for instance when discussing data derived from mouse samples, sialidases tested in these examples were human sialidases.

Example 1

Sialidase Effects on LAP Assay

To determine the effect of sialidases on latency associated peptide (LAP), 400 ng/ml human recombinant LAP (246-LP/CF, R&D Systems, Minneapolis, MN) was incubated with and without 200 ng/ml of human recombinant sialidases NEU1 (TP300386, Origene, Rockville, MD), NEU2 (TP319858, Origene), NEU3 (TP316537, Origene), or NEU4 (TP303948, Origene), or *C. perfringens* neuraminidase (N2876-2.5UN, Sigma-Aldrich, St. Louis, MO), or 1 μl of 0.1N HCl (H613-05, Avantor Performance Materials LLC., Center Valley, PA) in a total volume of 20 μl of phosphate buffered saline (PBS; #SH30256.01, GE Lifesciences, Marlborough, MA) pH 6.9. The PBS was adjusted to pH 6.9, approximately corresponding to an extracellular pH in normal tissue, with 12N HCl (H613-05, Avantor Performance Materials LLC). The reaction mixtures were incubated at 37° C. for 2 hours in 1.7 ml clear microtubes (22-281, Genesee Scientific, San Diego, CA). Following incubation, 5 μl of 4× Laemmli's buffer (GTX16355, GeneTex, Nottingham Business Park Nottingham, UK) containing 20 mM dithiothreitol was added to the reaction mixtures, and these were heated at 100° C. for 5 minutes. 15 μl of the heated reaction mixture was electrophoresed on a 4-20% Tris/glycine polyacrylamide pre-cast gel (12001-058, VWR, Radnor, PA) in Tris/glycine/SDS running buffer (13.5 g Tris base, 7.2 g glycine, 5 g SDS/liter) at room temperature for 90-120 minutes.

Proteins were transferred to polyvinylidene difluoride (Immobilon P; Millipore, Bedford, MA) membranes in Tris/glycine/SDS buffer containing 20% methanol following the manufacturer's protocol. Membranes were blocked for 1 hour at room temperature with 1× carbo-block solution (SP-5040, Vector, Burlingame, CA) diluted in water, and were then incubated for 30 minutes at room temperature with 2 μg/ml of biotinylated *Sambucus nigra* lectin (SNA) (B-1305, Vector) in PBS pH 6.9. Membranes were then washed with PBS containing 0.1% Tween-20 over 30 minutes and were then incubated for 1 hour at room temperature with horseradish peroxidase-Streptavidin (405103, Biolegend, San Diego, CA) diluted 1:5,000 in PBS-bovine serum albumin (BSA). SuperSignal West Pico Chemiluminescence Substrate (34087, Thermo Scientific, Rockford, IL) was used following the manufacturer's protocol to visualize the peroxidase, using a ChemiDoc XRS+ System (Bio-Rad, Hercules, CA). Statistical analysis was done with Prism software (Graphpad, La Jolla, CA).

Figure 2A:
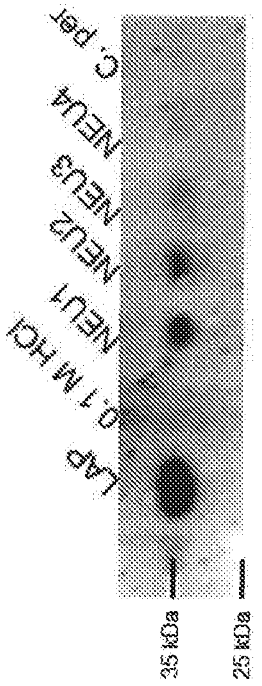
FIG. 2A is a Western blot of recombinant human LAP protein stained with *Sambucus nigra* lectin, which detects sialic acids on glycoconjugates.
Figure 2B:
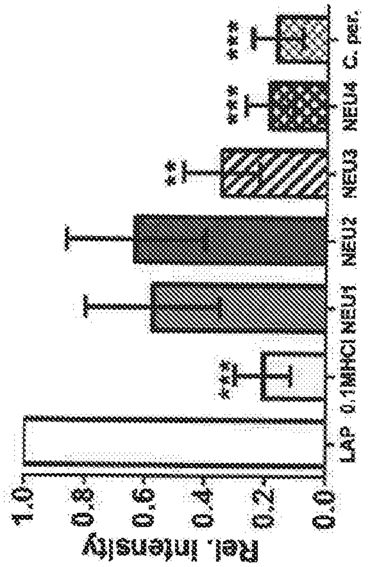
FIG. 2B is a graph of quantified *Sambucus nigra* sialic acid staining of recombinant human LAP protein from FIG. 2A. Values are mean±SEM, n=3. $=p\leq 0.01$, $*=p\leq 0.001$ compared to LAP (1-way ANOVA, Bonferroni's test).

Results are presented in FIGS. 2A-B. The data show NEU3 and NEU4 exposure significantly decreased SNA lectin binding to LAP, indicating a decrease in the number of polysaccharides containing sialic acid having an α(2,6)-linkage. Values are mean±SEM, n=3. $^{}=p\leq 0.01$, $^{*}=p\leq 0.001$ (1-way ANOVA, Bonferroni's test).

Example 2

NEU3 Induced L-TGF-β1 Activation Assay

To determine if NEU3 can cause latent transforming growth factor-β1 (L-TGF-β1) to release active TGF-β1, 200 ng/ml recombinant human L-TGF-β1 (299-LT/CF, R&D Systems) was incubated with varying concentrations of recombinant human NEU3 (TP316537, Origene) in a total volume of 100 μl of PBS pH 6.9 in a 96-well microplate (651261, Greiner Bio-one, Monroe, NC). The microplates were covered with aluminum foil and incubated at 37° C. for 2 hours. Following incubation, the reaction mixtures were assayed using a TGF-β1 ELISA kit (DY240, R&D Systems) following the manufacturer's protocol with the exception that the reaction mixtures were not processed for acid treatment, so as to measure only active TGF-β1 and not total TGF-β1. The absorbance was read with a SynergyMX plate reader (BioTek, Winooski, VT).

Figure 3:
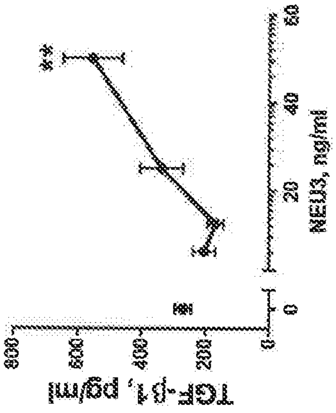
FIG. 3 is a graph quantifying an ELISA assay, specific to active TGF-β1, performed on CHO-synthesized recombinant human L-TGF-β1 treated with recombinant human NEU3. Values are mean±SEM, n=6. $**=p\leq 0.01$ compared to 0 NEU3 (1-way ANOVA, Bonferroni's test).

Results are presented in FIG. 3. The data show NEU3 exposure activated L-TGF-β1 by removing sialic acid from the LAP protein. The LAP protein then released active TGF-β1. Values are mean±SEM, n=6. **=p≤0.01 (1-way ANOVA, Bonferroni's test).

Example 3

NEU3 Inhibitors Prevent L-TGF-β1 Activation by NEU3

To determine the ability of compounds 1-31 to inhibit human recombinant NEU3 in-vitro, compounds were dissolved in 5 ml water to 20 mM in 15 ml tubes (89039-664, VWR, Radnor, PA), with the exception that 4-hydroxypyridine-2-carboxylic acid, nicotinic acid, and 4-aminopicolinic acid were dissolved in 50 μl DMSO to 2 M, and this was then added to 4.95 ml of water to make a 20 mM stock, and O-(tetrahydro-2H-pyran-2yl) hydroxylamine and salicylic acid were dissolved in 50 μl methanol to 2 M, and this was then added to 4.95 ml of water to make a 20 mM stock. All stocks were stored at 4° C. and used within 2 weeks of preparation. A 10-fold dilution series of the compounds starting at 2 mM were made in PBS pH 6.9 in 1.7 ml clear microtubes (22-281, Genesee Scientific). 100 μl of diluted compound was added to the well of a 96 well plate and then 50 μl of 400 ng/ml recombinant human sialidase NEU3 (TP316537, Origene) in PBS pH 6.9 was added to each well (50 μl PBS pH 6.9 for the control), and the plate was incubated for 30 minutes at 37° C. 50 μl of 800 ng/ml L-TGF-β1 (299-LT/CF, R&D Systems) in PBS pH 6.9 was then added to the well. The plate was covered with aluminum foil and incubated for 2 hours at 37° C., and released active TGF-β1 was assayed as described above.

Figure 4A:
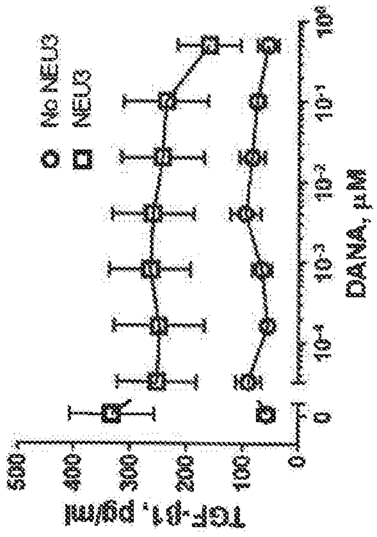
FIGS. 4A-4BH are graphs quantifying the inhibition of NEU3-catalyzed TGF-β1 activation as measured by a TGF-β1 ELISA kit. Values are mean±SEM, n≥3.
Figure 4B:
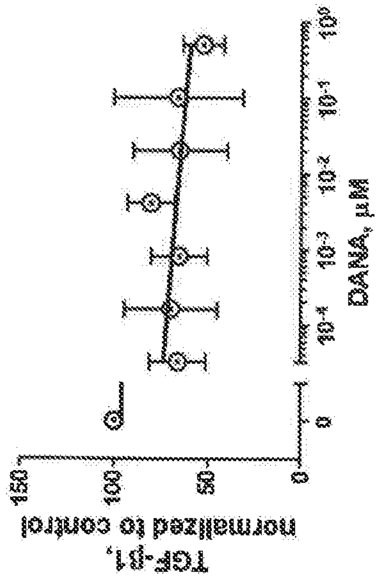
Figure 4C:
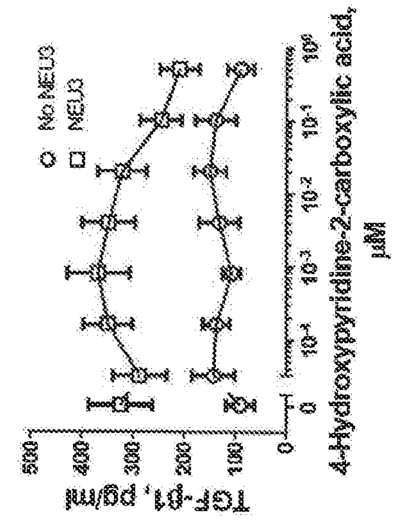
Figure 4D:
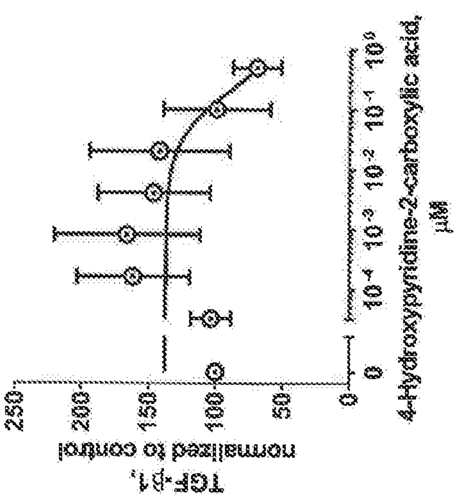
Figure 4E:
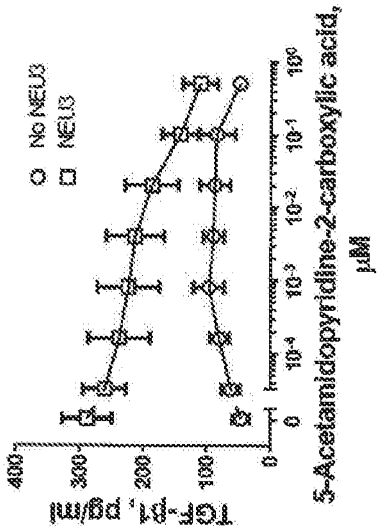
Figure 4F:
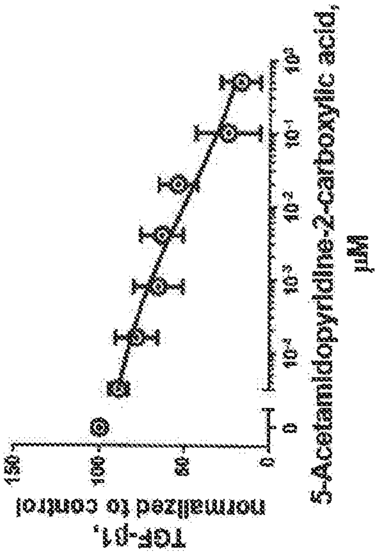
Figure 4G:
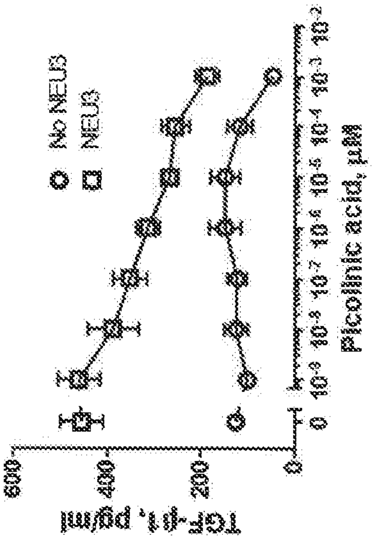
Figure 4H:
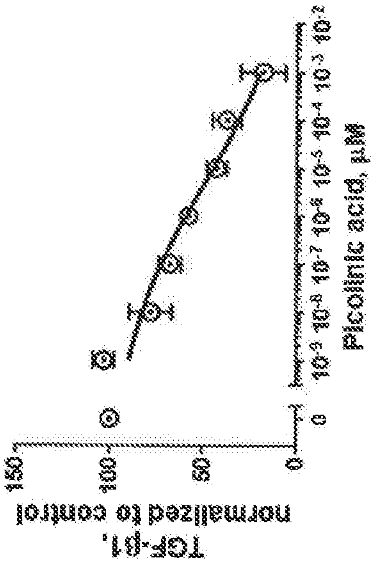
Figure 4J:
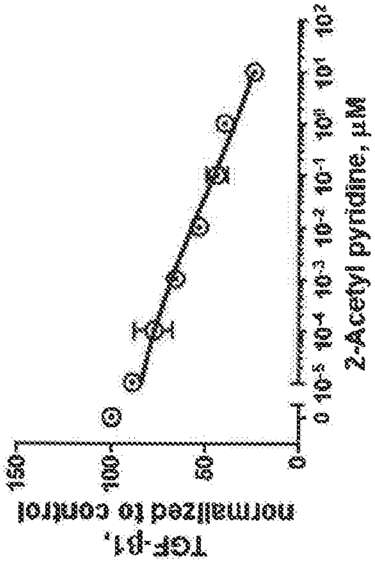
Figure 4I:
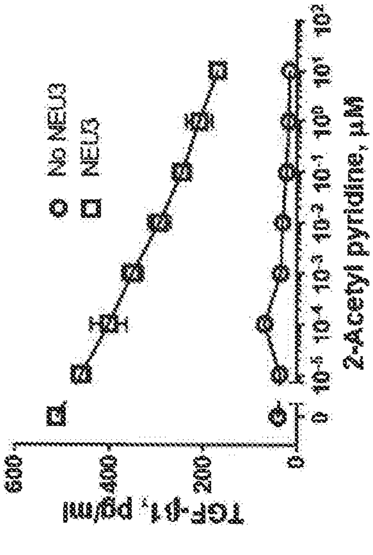
Figure 4L:
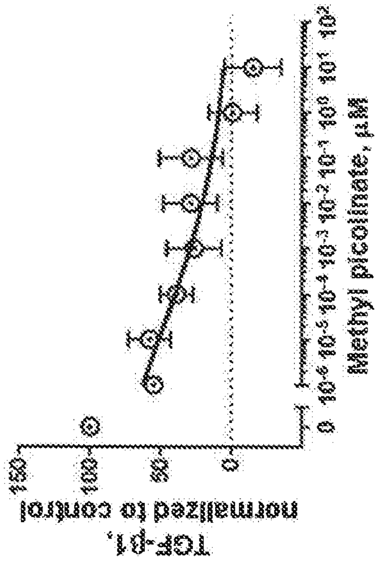
Figure 4K:
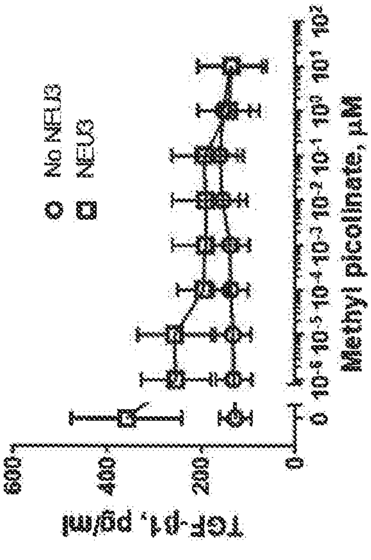
Figure 4M:
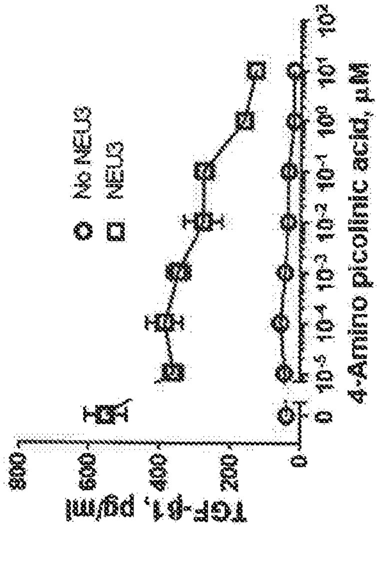
Figure 4N:
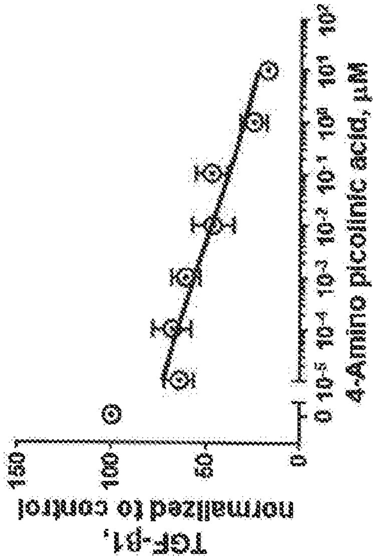
Figure 4O:
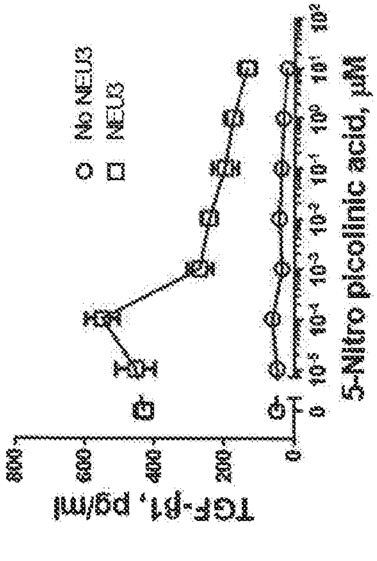
Figure 4P:
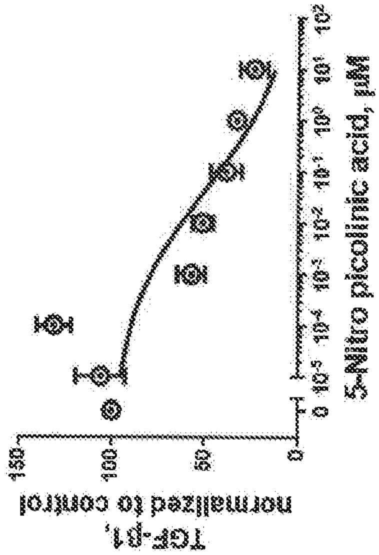
Figure 4Q:
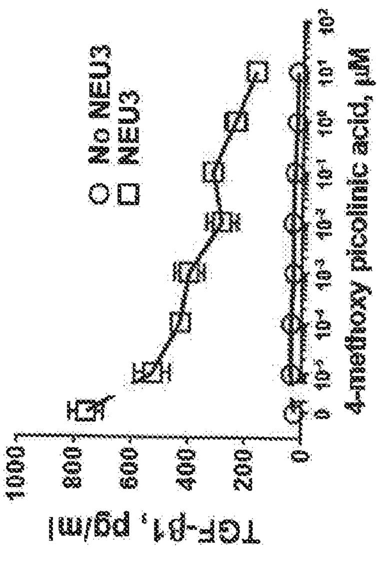
Figure 4R:
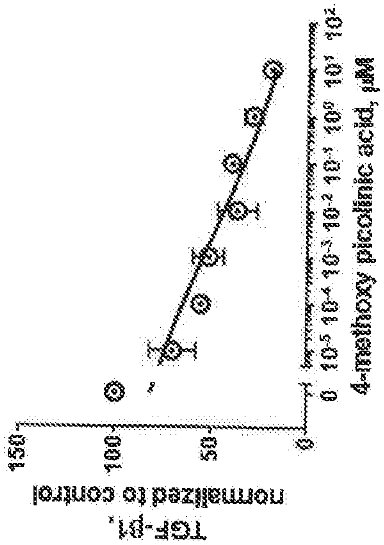
Figure 4S:
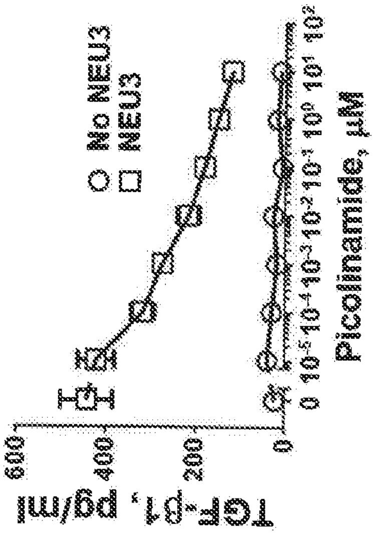
Figure 4T:
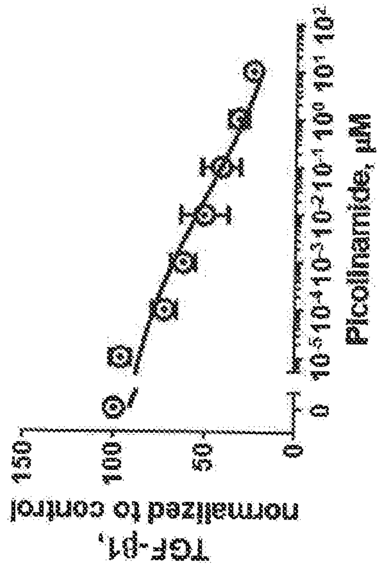
Figure 4U:
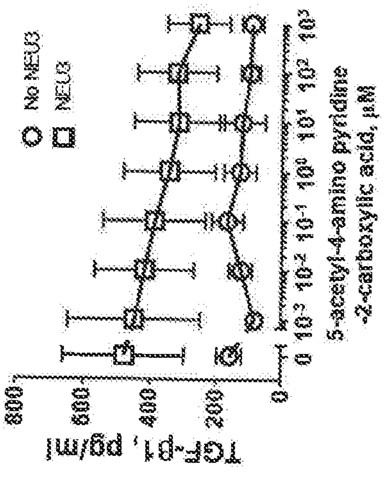
Figure 4V:
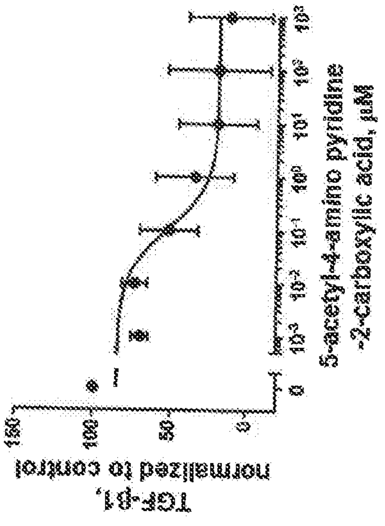
Figure 4W:
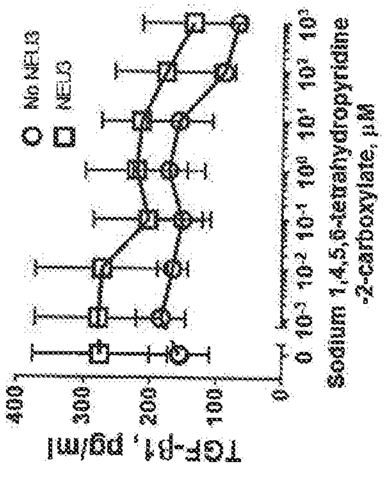
Figure 4X:
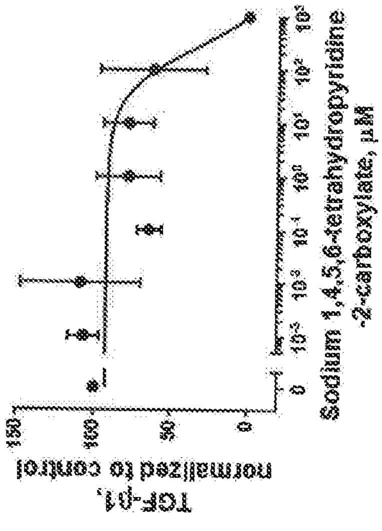
Figure 4Y:
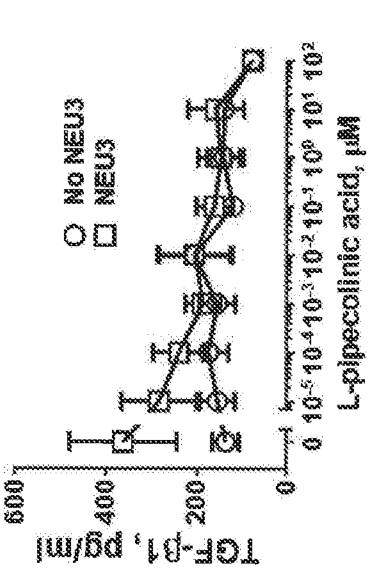
Figure 4Z:
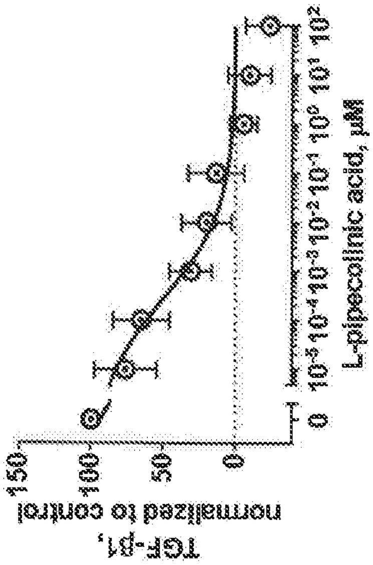
Figure 4A:
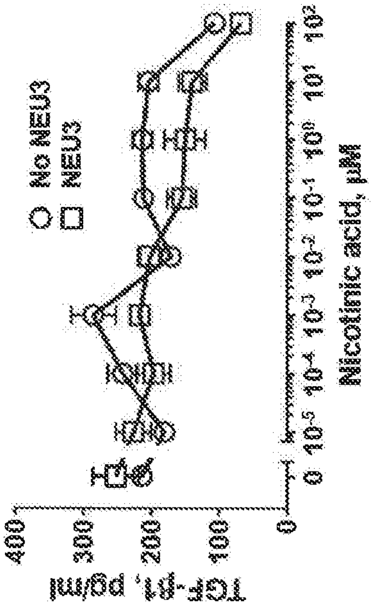
Figure 4A:
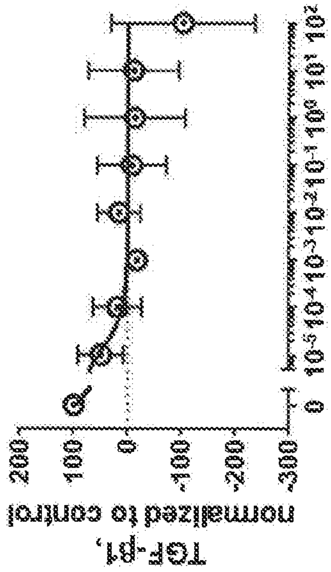
Figure 4A:
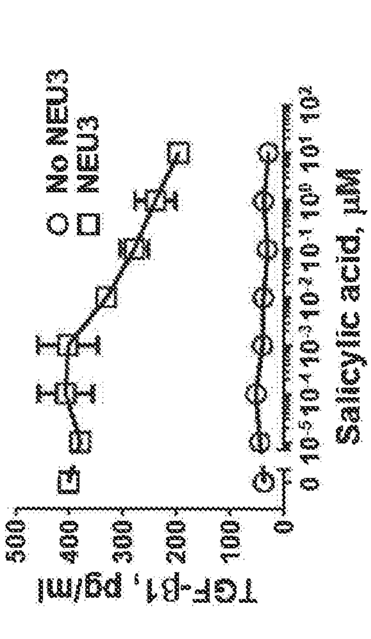
Figure 4A:
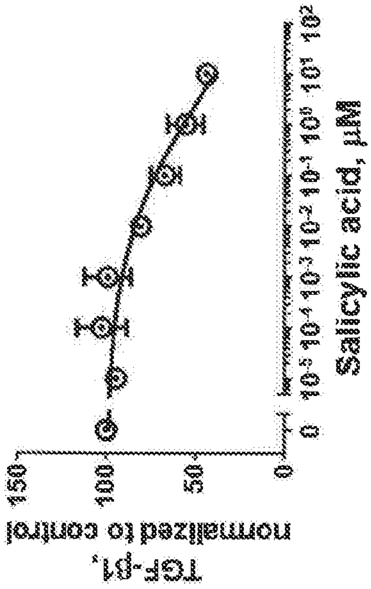
Figure 4A:
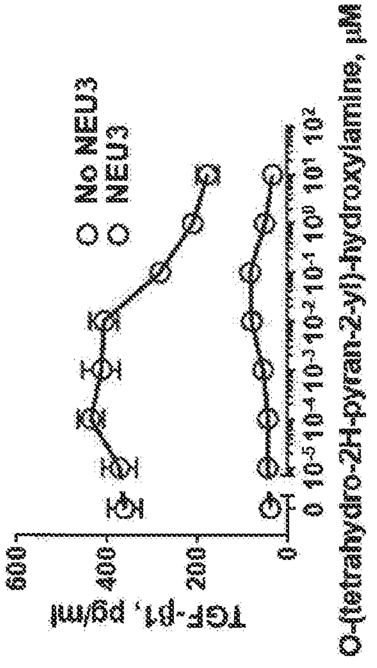
Figure 4A:
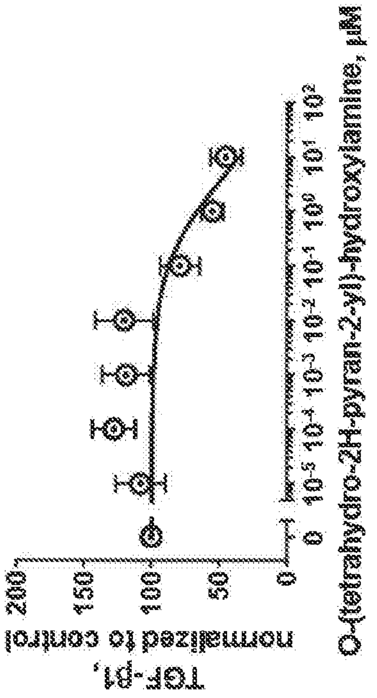
Figure 4A:
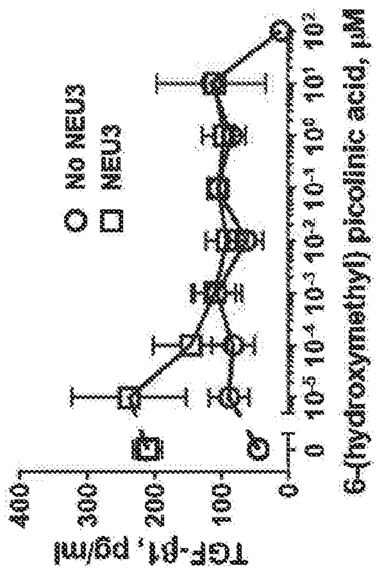
Figure 4A:
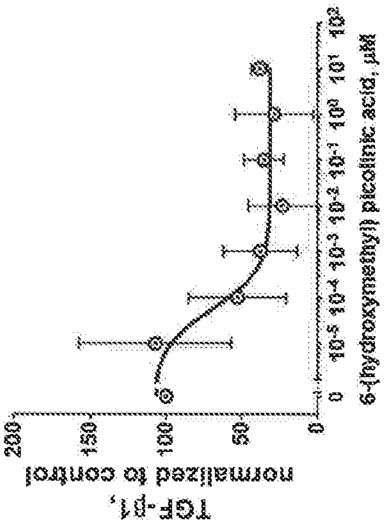
Figure 4A:
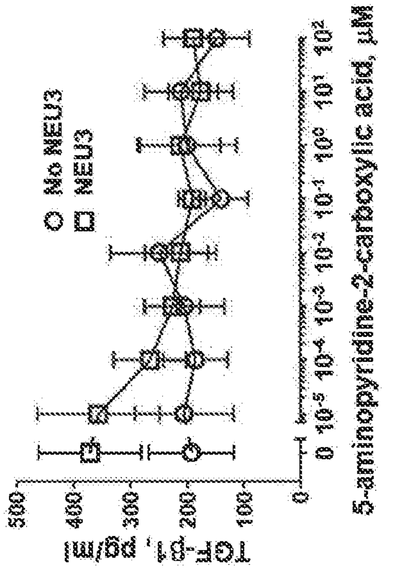
Figure 4A:
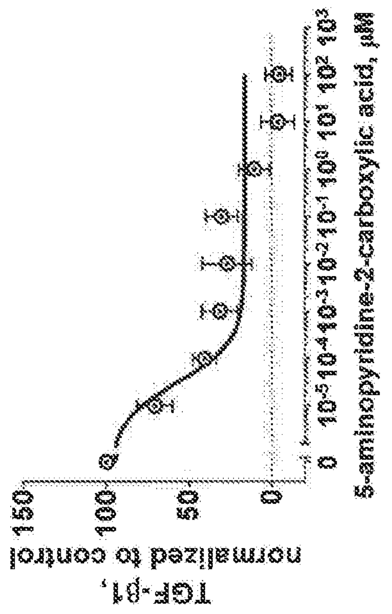
Figure 4A:
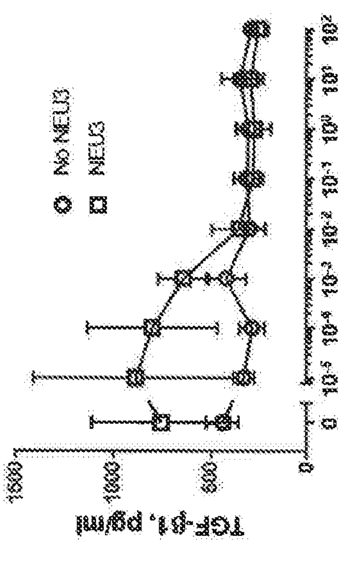
Figure 4A:
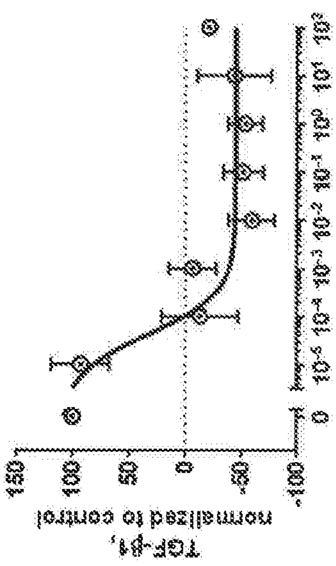
Figure 4A:
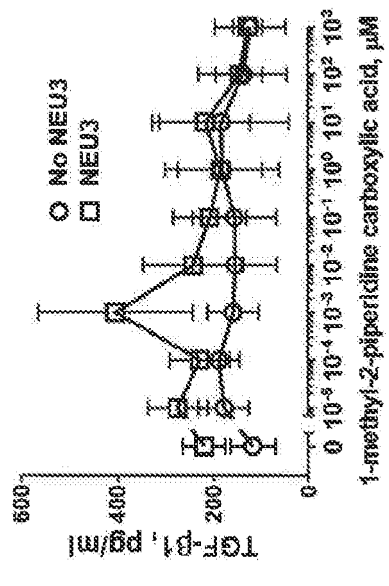
Figure 4A:
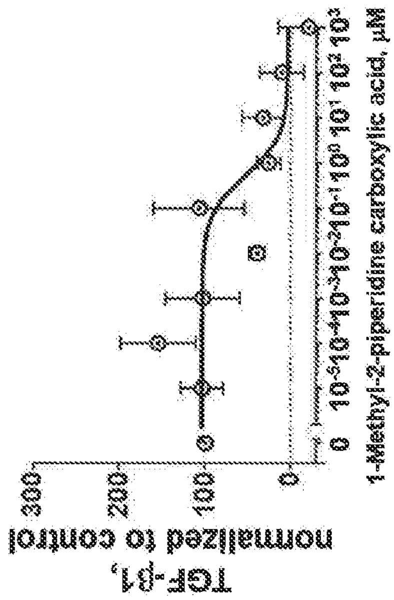
Figure 4A:
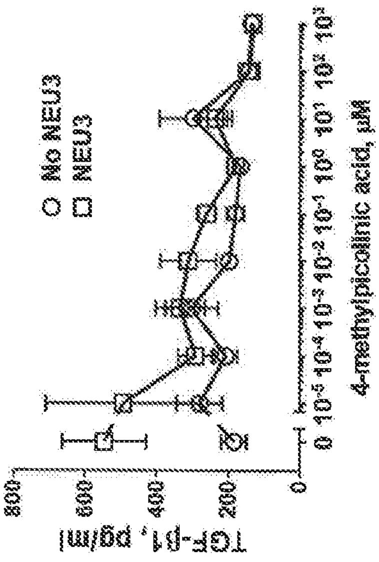
Figure 4A:
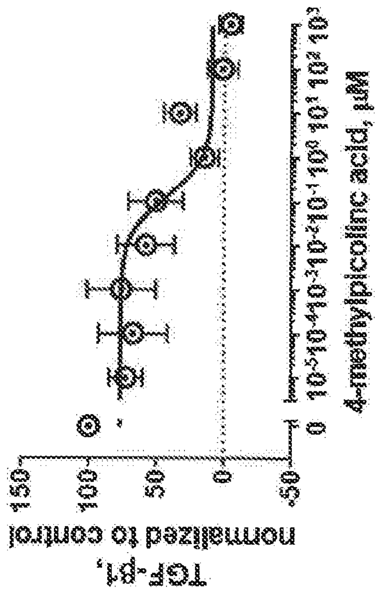
Figure 4A:
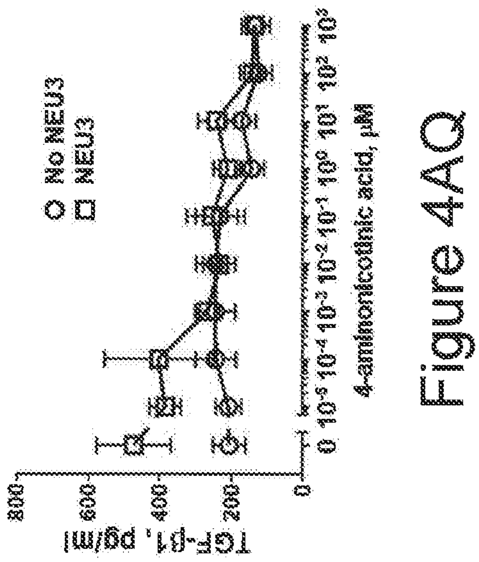
Figure 4A:
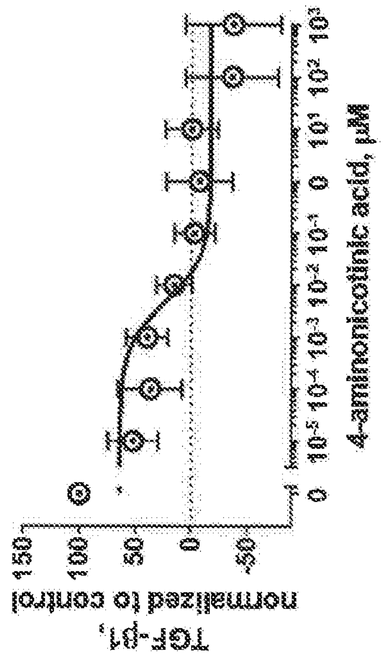
Figure 4A:
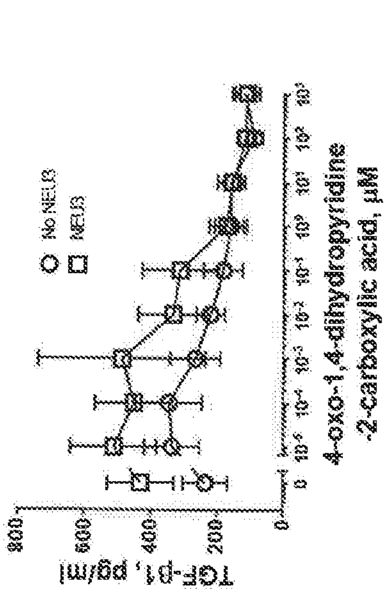
Figure 4A:
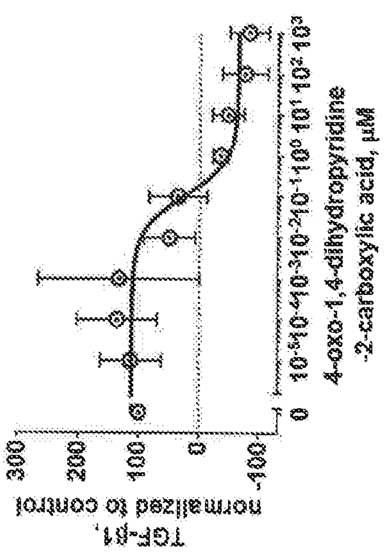
Figure 4A:
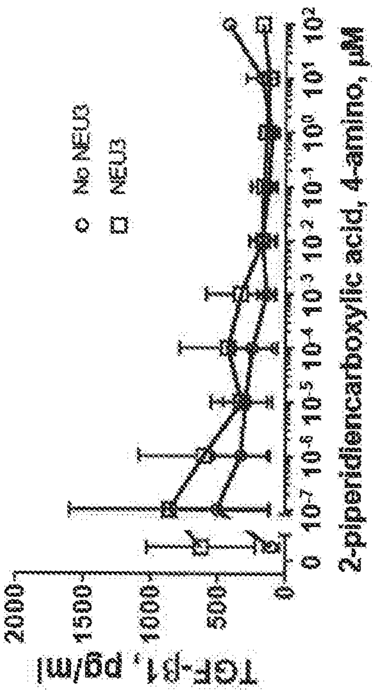
Figure 4A:
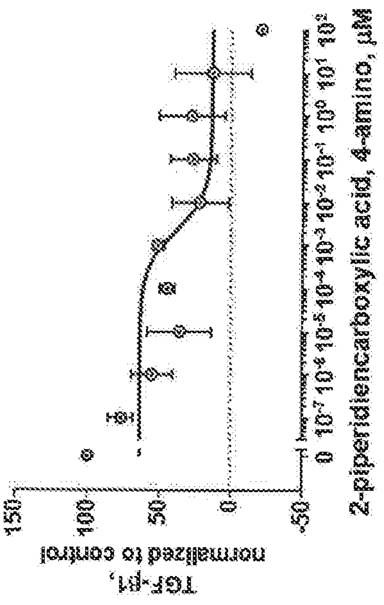
Figure 4A:
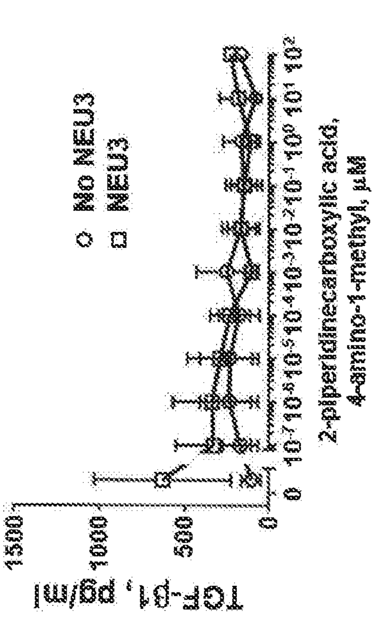
Figure 4A:
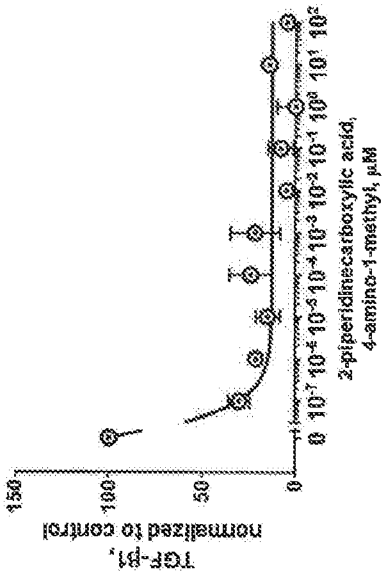
Figure 4A:
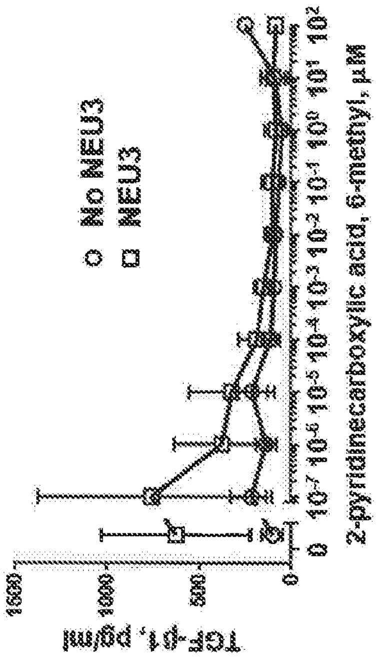
Figure 4A:
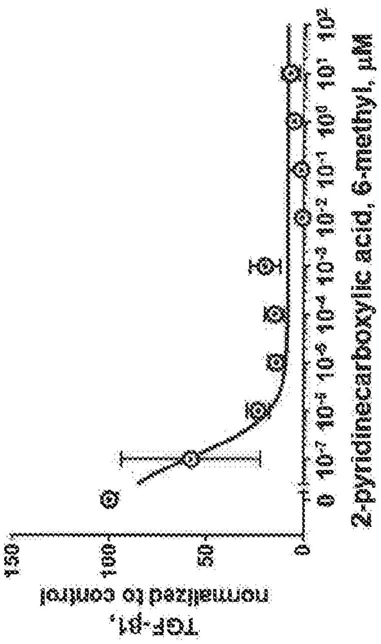
Figure 4B:
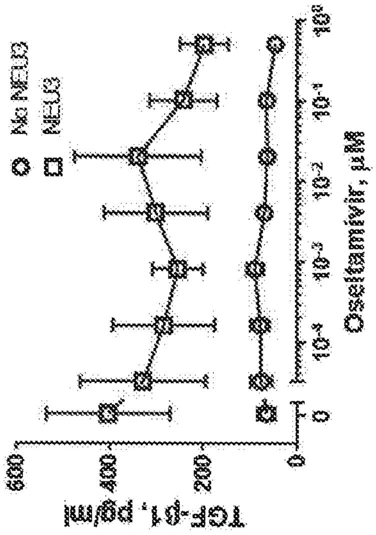
Figure 4B:
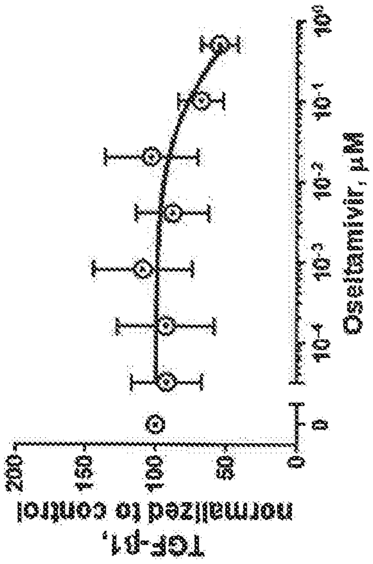
Figure 4B:
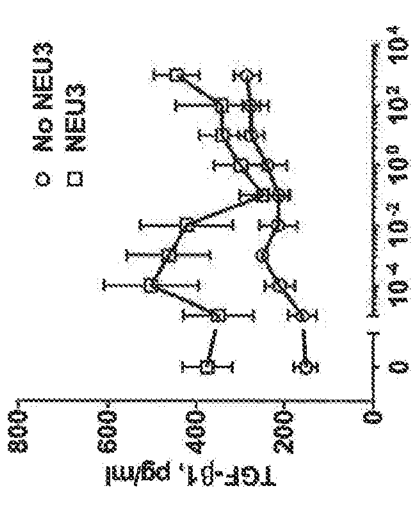
Figure 4B:
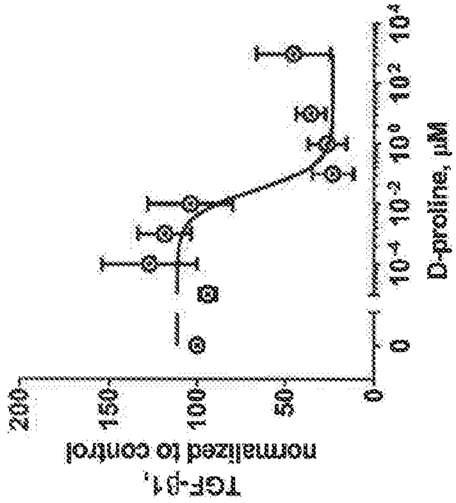
Figure 4B:
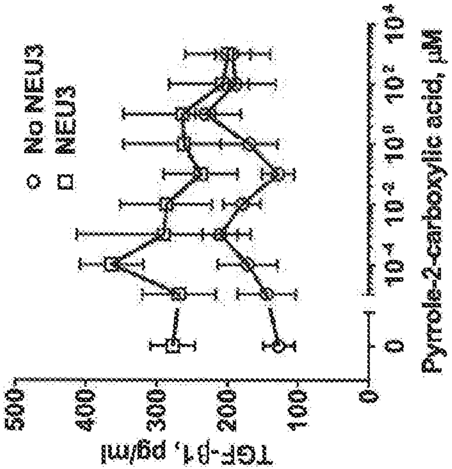
Figure 4B:
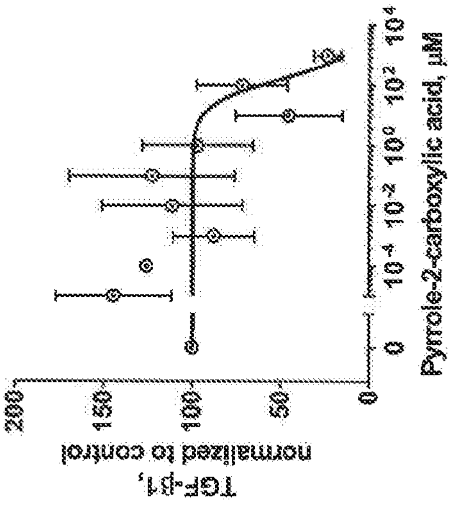
Figure 4B:
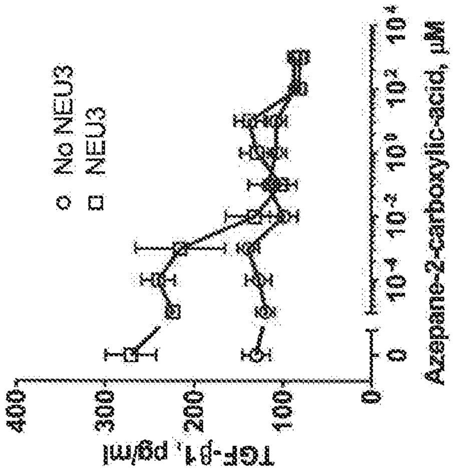
Figure 4B:
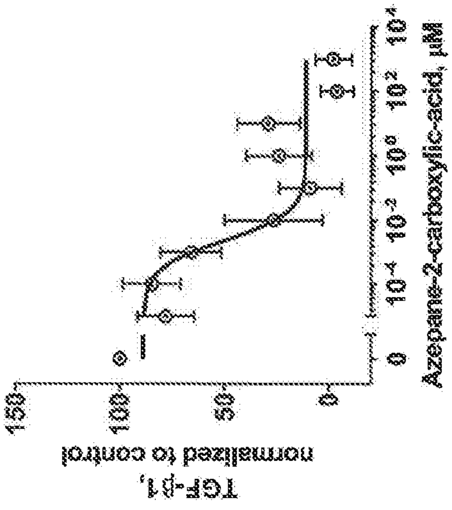

Results are presented in FIGS. 4A-BH. NEU3 inhibition ranged from >100 μM to <1 nM. Values are mean±SEM, n≥3.

Example 4

The Effect of NEU3 on IL-6 Production by PBMC Assay

Human peripheral blood was collected from healthy volunteers who gave written consent and with specific approval from the Texas A&M University human subjects review board. Peripheral blood mononuclear cells (PBMC) were isolated from the blood using Ficoll-Paque density gradient centrifugation (95021-205, GE Healthcare, Cincinnati, OH) following the manufacture's protocol. PBMC were cultured at $5\times10^4$ cells/ml in 96-well flat bottom tissue culture plates (type 62406-081; VWR, Radnor, PA) with RPMI-1640 (12001-560, VWR) supplemented with 10% bovine calf serum (BCS) (10158-358, VWR), 100 U/ml penicillin, 100 μg/ml streptomycin, (12001-692, VWR) and 2 mM glutamine (12001-698, VWR) in a final volume of 200 μl per well. Cells were also cultured at $5\times10^4$ cells/ml in serum-free medium (RPMI-1640 supplemented with 10 mM HEPES (12001-708, VWR), 1× non-essential amino acids (12001-634, VWR), 1 mM sodium pyruvate (12001-636, VWR), 2 mM glutamine (12001-698, VWR), 100 U/ml penicillin, 100 μg/ml streptomycin (12001-692, VWR), and 1×ITS-3 (12771, Sigma-Aldrich, St. Louis, MO)) in a final volume of 200 μl per well. When the cells were plated, human recombinant sialidases NEU1 (TP300386, Origene, Rockville, MD), NEU2 (TP319858, Origene), NEU3 (TP316537, Origene), or NEU4 (TP303948, Origene) were added to a final concentration of 0 or 100 ng/ml. In other experiments, recombinant human NEU3 was added to a final concentration of 0-500 ng/ml. The sialidases were diluted in 100 μl of the same medium the cells were in, and added to 100 μl of cells at $1\times10^5$ cells/ml to make the total volume in a well 200 μl with $1\times10^4$ cells/well. The cells were then incubated at 37° C. in a humidified incubator with 5% $CO_2$. The culture supernatants were collected after two or five days and assayed using an IL-6 ELISA kit (430501, Biolegend, San Diego, CA) following the manufacturer's protocol, reading absorbance with a SynergyMX plate reader (BioTek, Winooski, VT). Statistics were analyzed using Prism software (Graphpad, La Jolla, CA). At least three different donors were used for each assay.

Figure 5A:
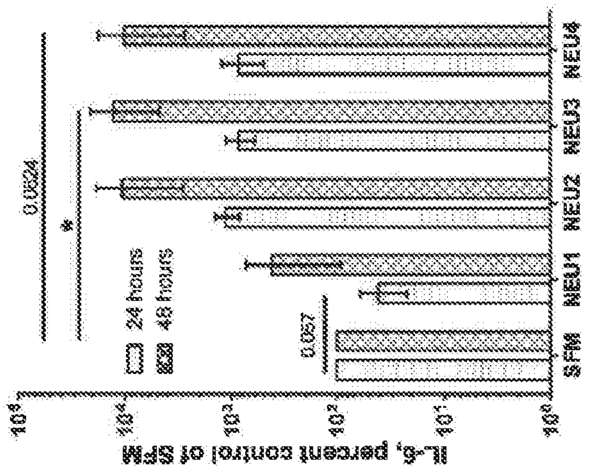
FIG. 5A is a graph quantifying extracellular accumulation of IL-6 in human PBMC cultures after treatment with NEU1, NEU2, NEU3, or NEU4. Values are mean±SEM, n=3. $*=p\leq 0.05$ (t-test).
Figure 5C:
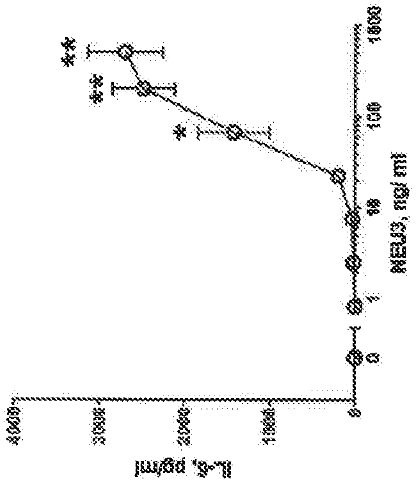
FIGS. 5B and 5C are graphs quantifying extracellular accumulation of IL-6 in human PBMC cultures after treatment with NEU3 in serum-free medium.
Figure 5B:
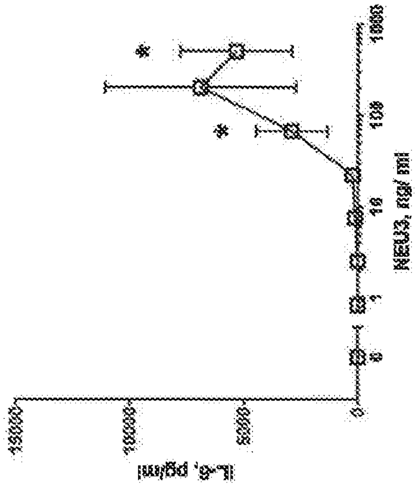
Figure 5E:
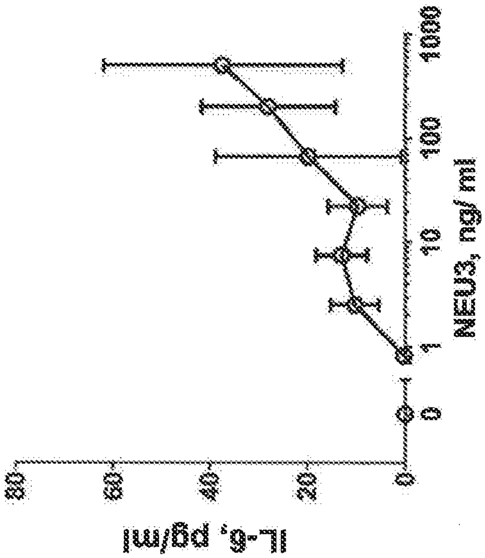
FIGS. 5D and 5E are graphs quantifying extracellular accumulation of IL-6 in human PBMC cultures after treatment with NEU3 in medium with serum.
Figure 5D:
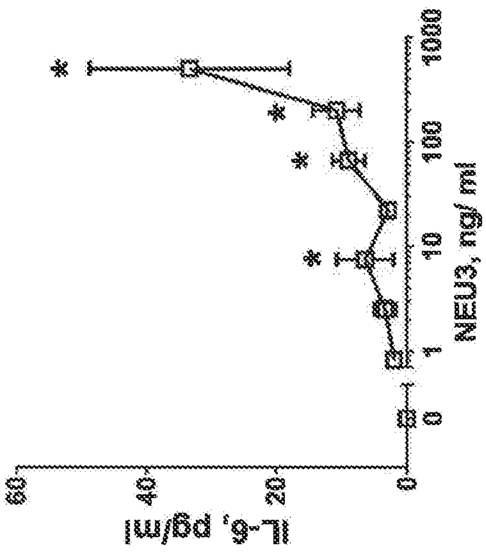

Results are presented in FIGS. 5A-C. FIG. 5A shows only NEU3 significantly increased extracellular IL-6 accumulation as compared to serum-free media (SFM) control. FIG. 5B-C show IL-6 accumulation as a function of NEU3 concentration in serum-free medium after 48 hours (FIG. 5B) and 5 days (FIG. 5C). Values are mean±SEM, n=3. *=p≤0.05, =p≤0.01 (t-test). FIG. 5D-E show IL-6 accumulation as a function of NEU3 concentration in medium with serum after 48 hours (FIG. 5D) and 5 days (FIG. 5**E). Values are mean±SEM, n=3. *=p≤0.05 (t-test).

Example 5

Effect of Compounds on the Ability of NEU3 to Induce Extracellular Accumulation of IL-6 by Human Immune Cells To determine the ability of compounds to inhibit NEU3-induced IL-6 production by human PBMC, 10-fold dilution series of compounds starting at 4 mM were made in serum-free medium (made as described above) in 1.7 ml clear microtubes (22-281, Genesee Scientific). 50 μl of diluted compound was added to the well of a 96 well plate and then 50 μl of 400 ng/ml recombinant human sialidase NEU3 (TP316537, Origene) in serum-free medium was added to each well (50 μl serum-free medium for control), and the plate was incubated for 30 minutes at 37° C. in a humidified incubator with 5% $CO_2$. 100 μl of PBMC at $1\times10^5$ cells/ml was then added to the well to make the total volume in a well 200 μl with $1\times10^4$ cells/well, and this was incubated at 37° C. in a humidified incubator with 5% $CO_2$ for 48 hours. IL-6 in the culture supernatant was then assayed as described above. At least three different donors were used for each assay.

Figure 6B:
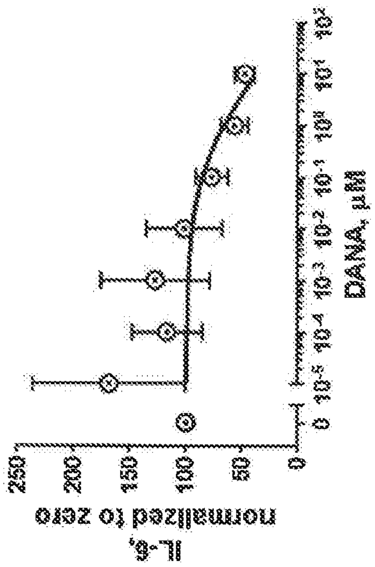
FIGS. 6A-6AZ are graphs quantifying extracellular accumulation of IL-6 in human PBMC cultures after treatment with NEU3 and selected compounds after 48 hours. Values are mean±SEM, n≥3.
Figure 6D:
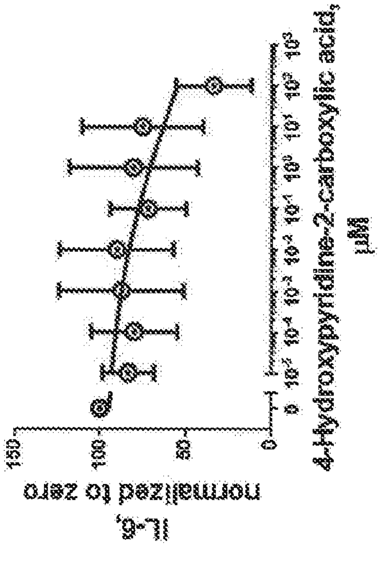
Figure 6A:
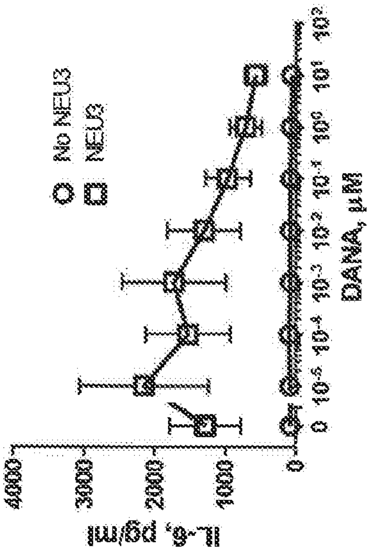
Figure 6C:
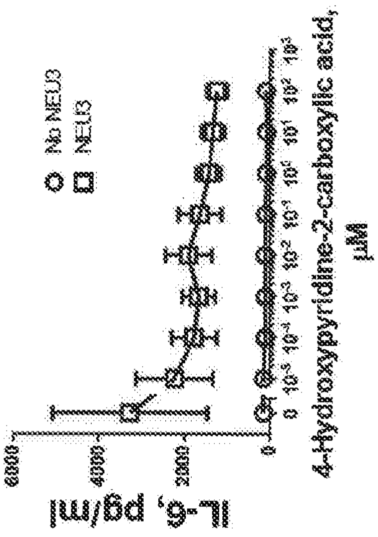
Figure 6E:
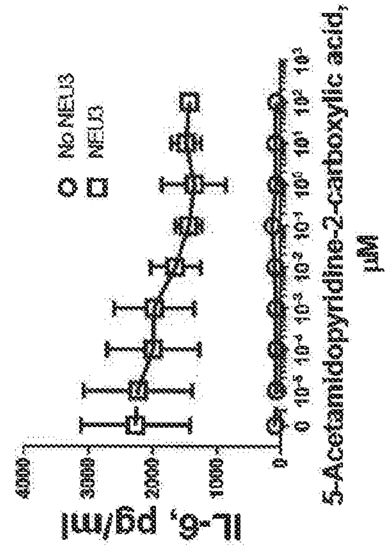
Figure 6F:
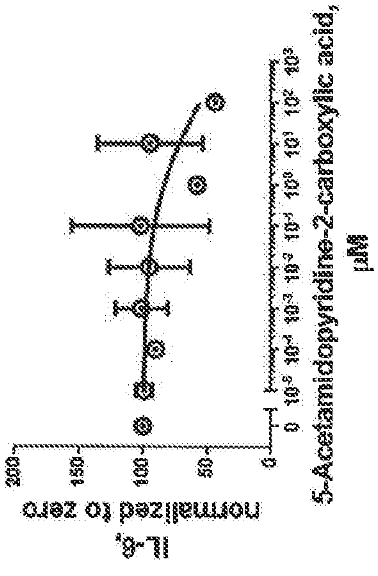
Figure 6G:
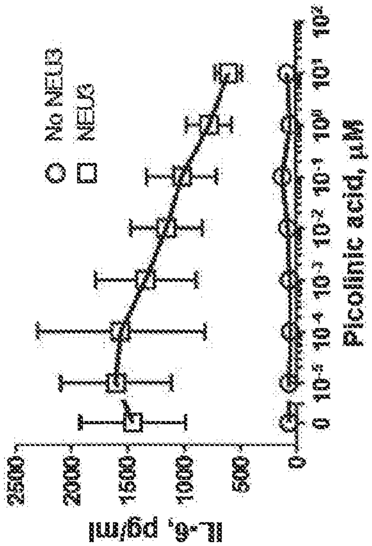
Figure 6H:
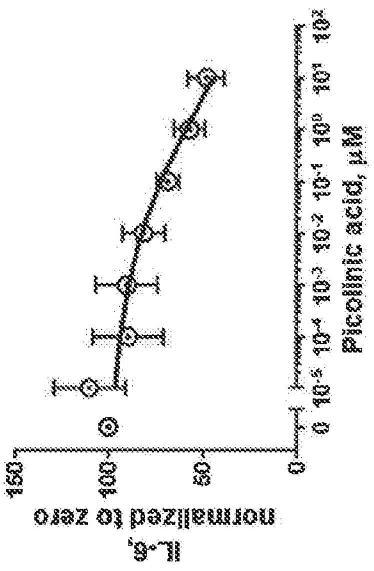
Figure 6J:
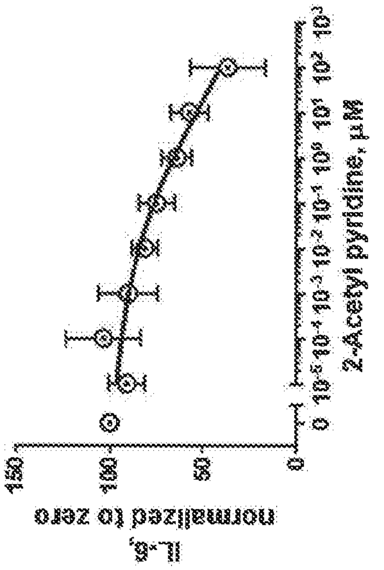
Figure 6L:
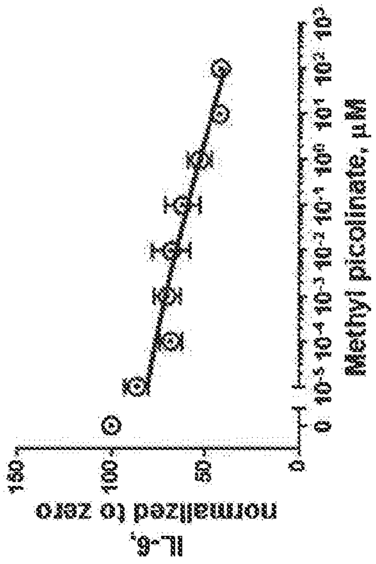
Figure 6I:
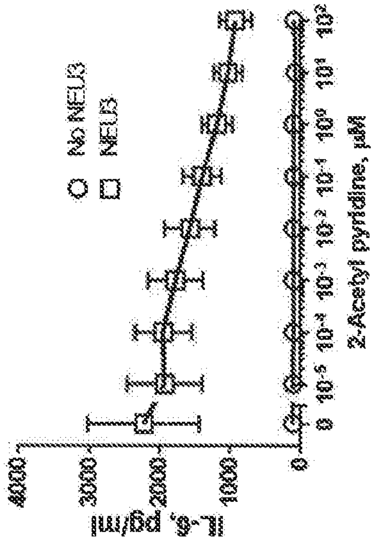
Figure 6K:
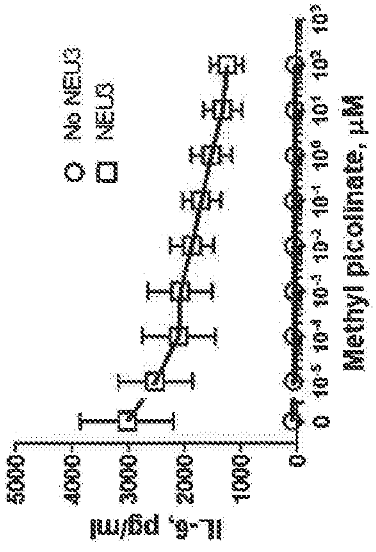
Figure 6M:
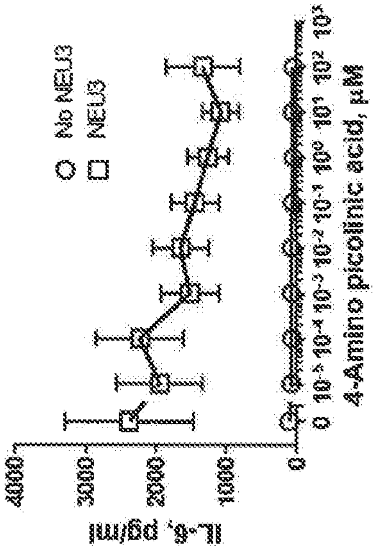
Figure 6N:
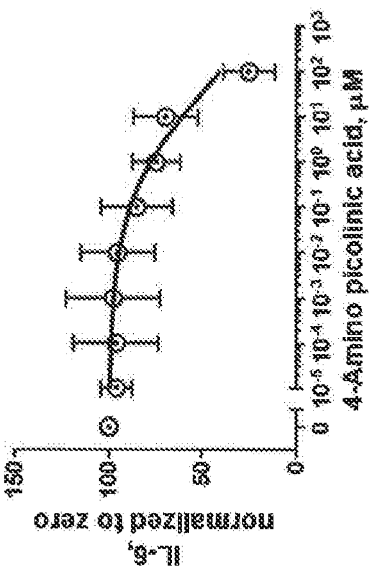
Figure 6O:
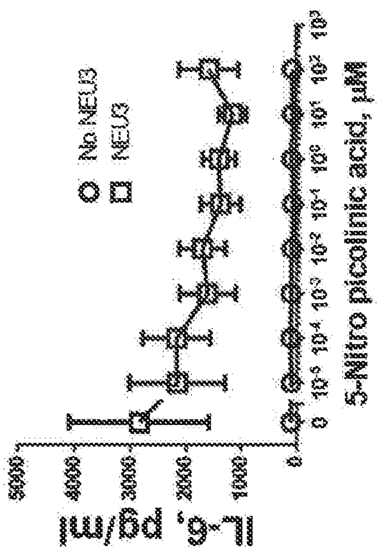
Figure 6P:
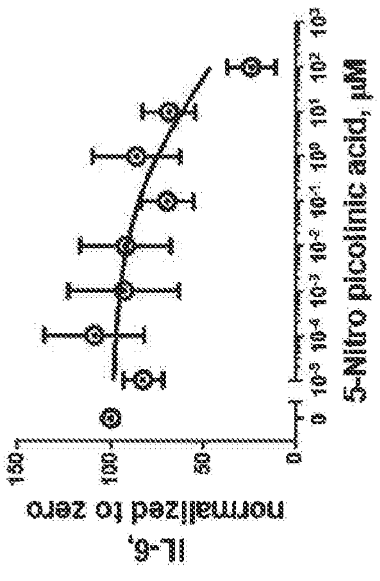
Figure 6Q:
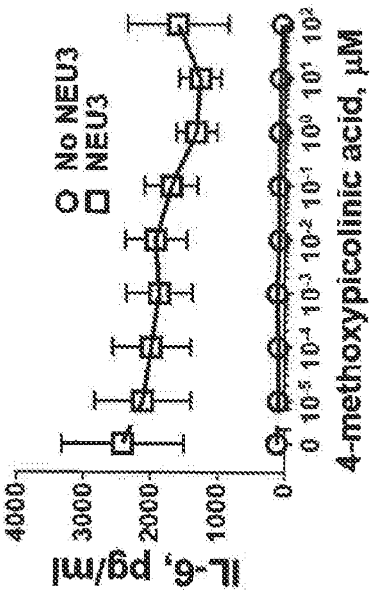
Figure 6R:
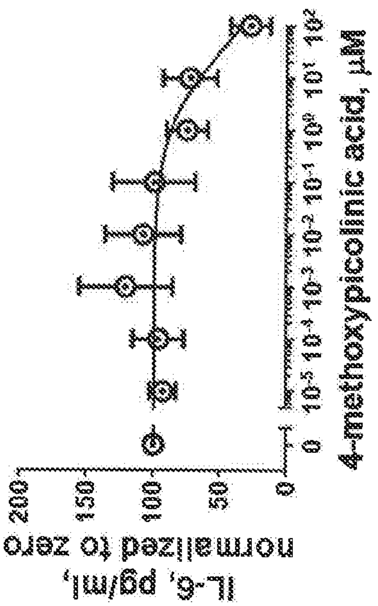
Figure 6S:
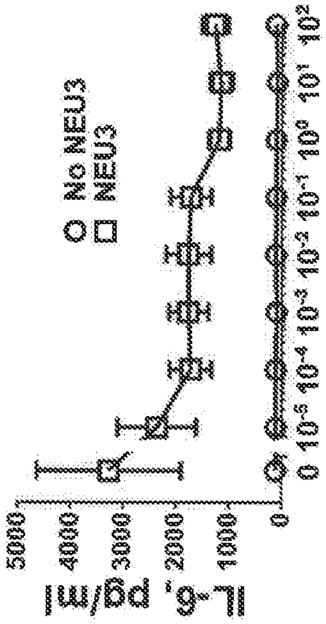
Figure 6T:
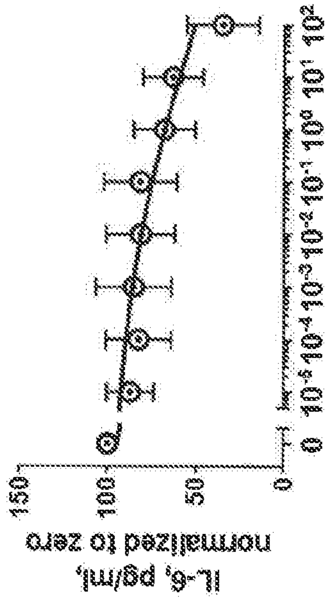
Figure 6U:
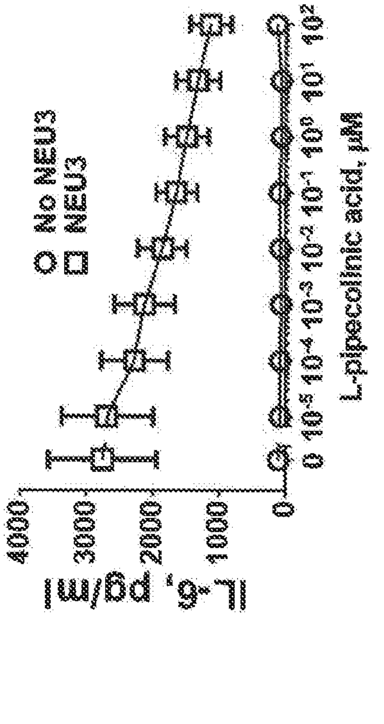
Figure 6V:
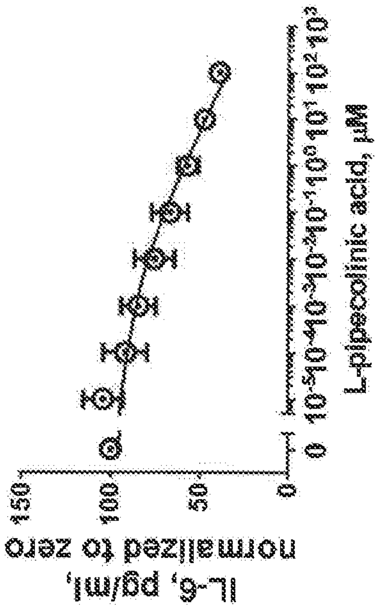
Figure 6W:
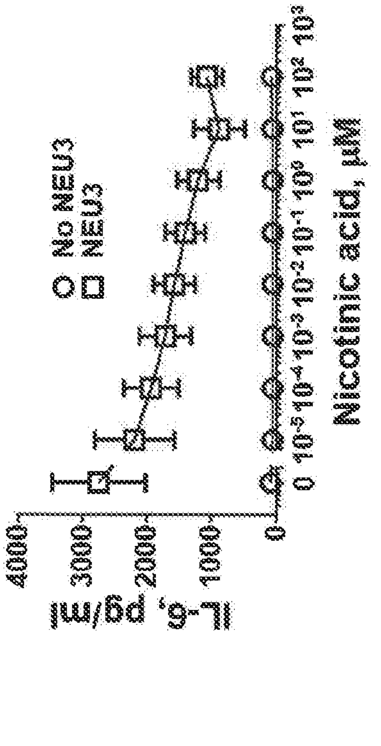
Figure 6X:
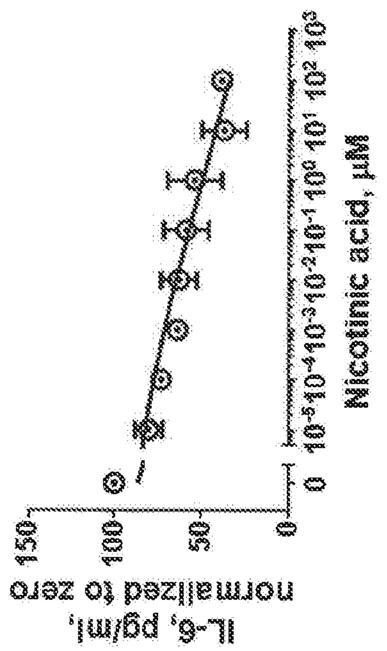
Figure 6Y:
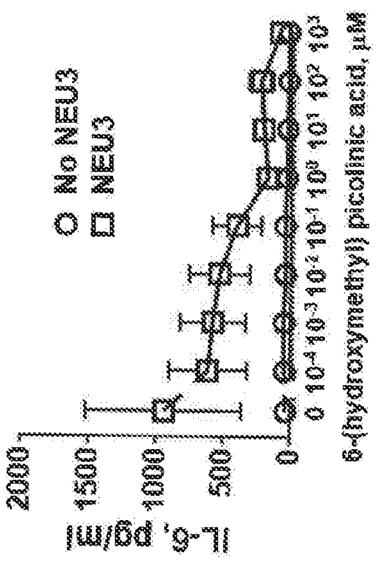
Figure 6Z:
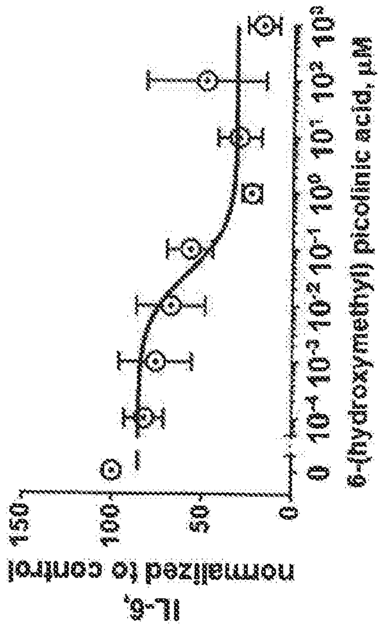
Figure 6A:
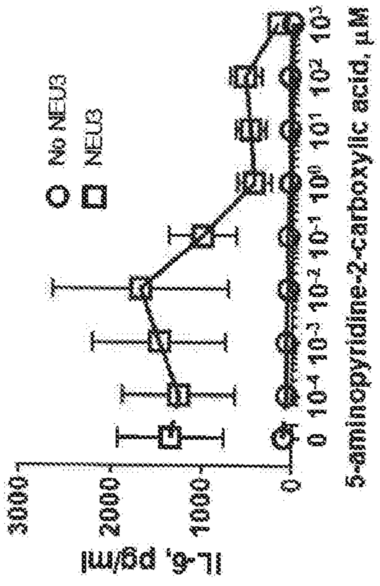
Figure 6A:
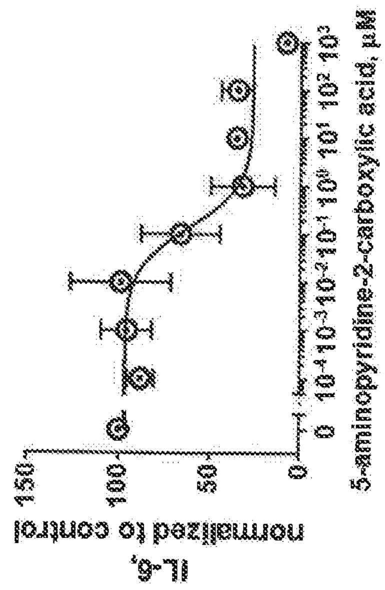
Figure 6A:
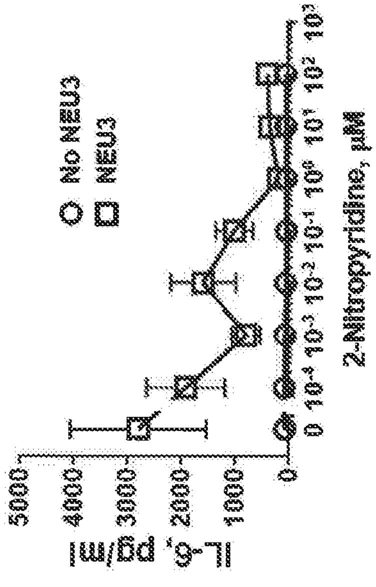
Figure 6A:
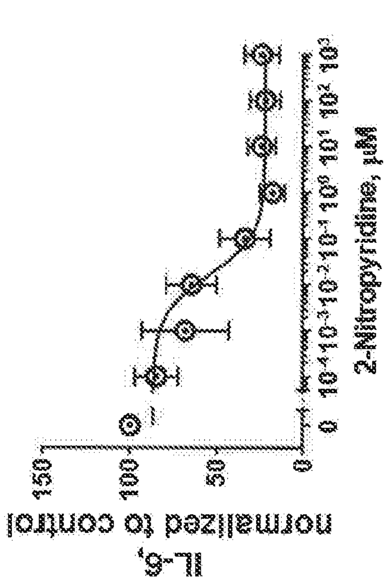
Figure 6A:
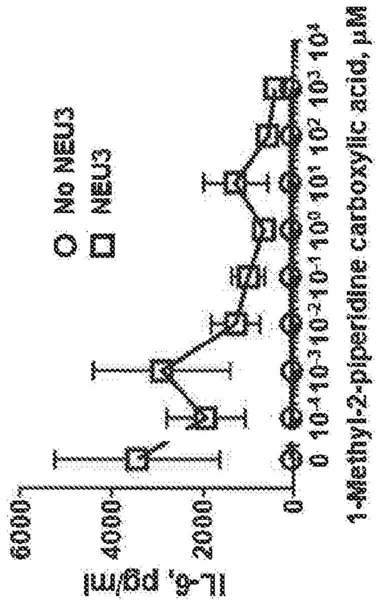
Figure 6A:
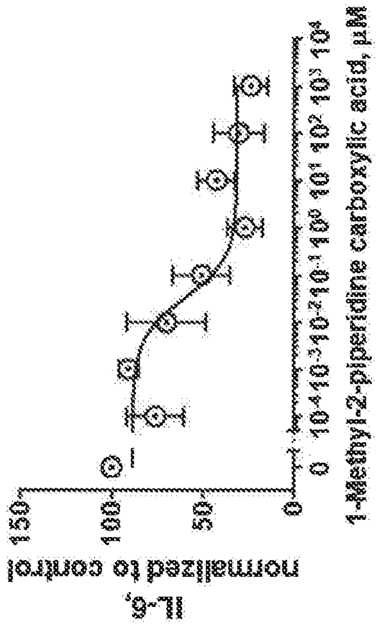
Figure 6A:
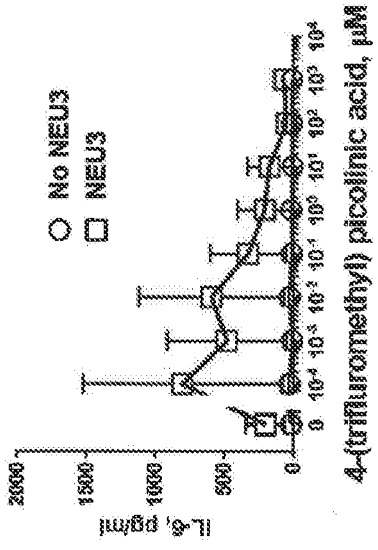
Figure 6A:
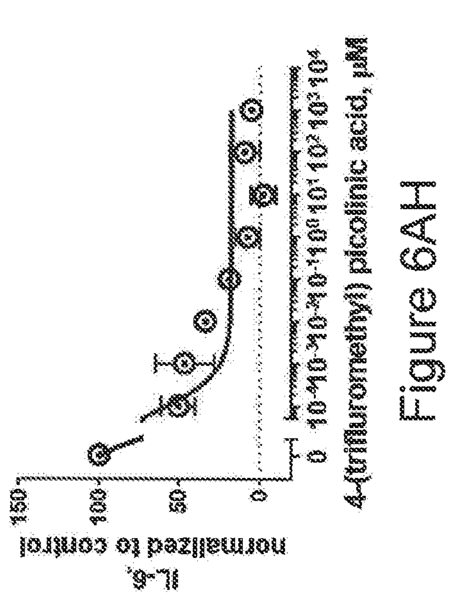
Figure 6A:
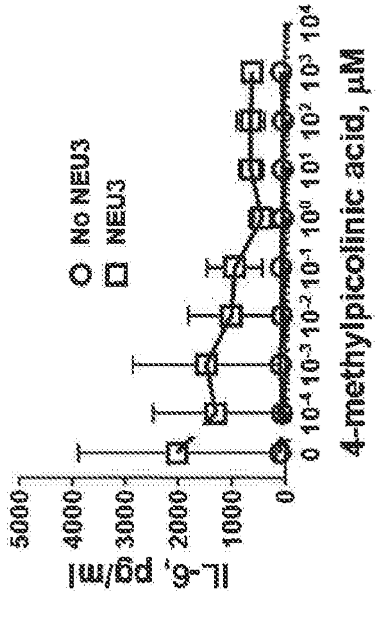
Figure 6A:
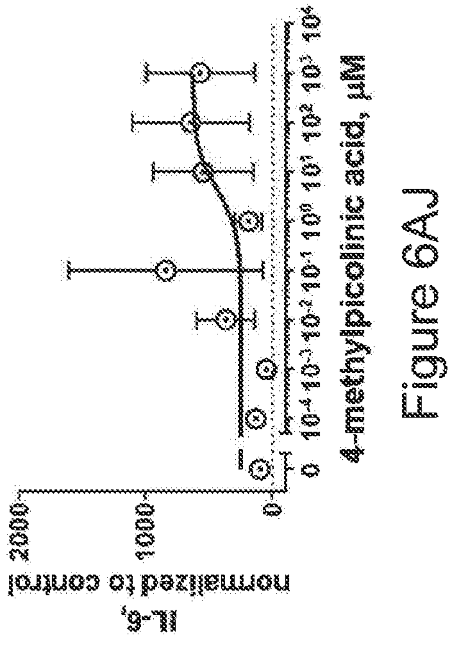
Figure 6A:
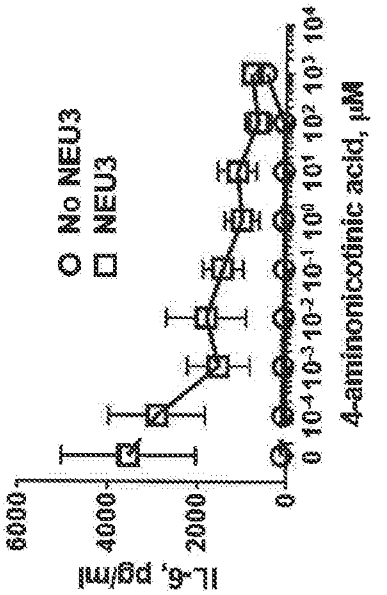
Figure 6A:
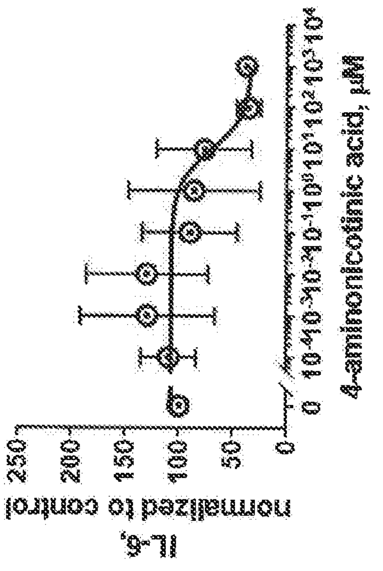
Figure 6A:
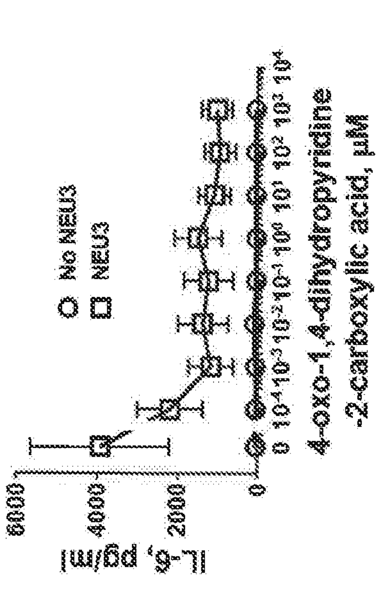
Figure 6A:
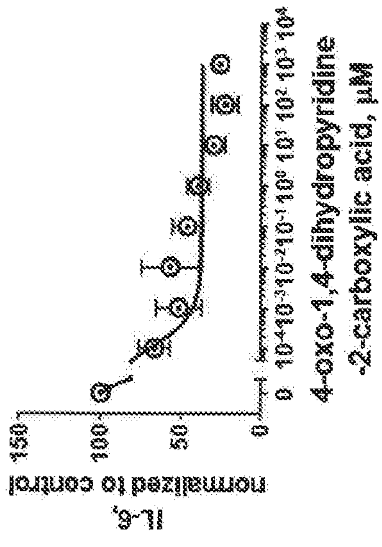
Figure 6A:
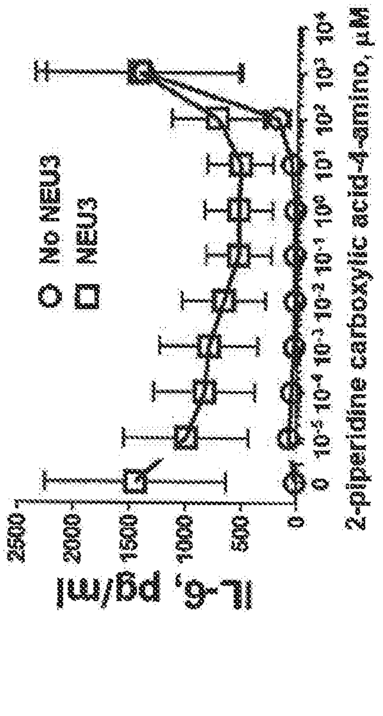
Figure 6A:
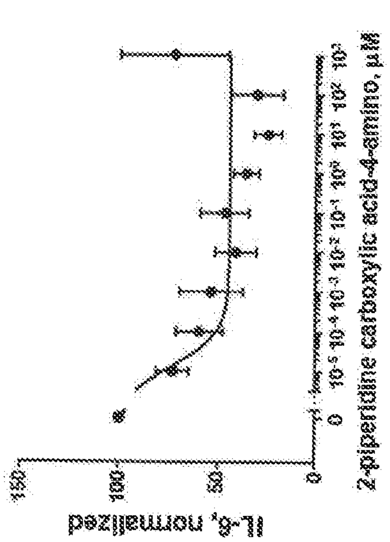
Figure 6A:
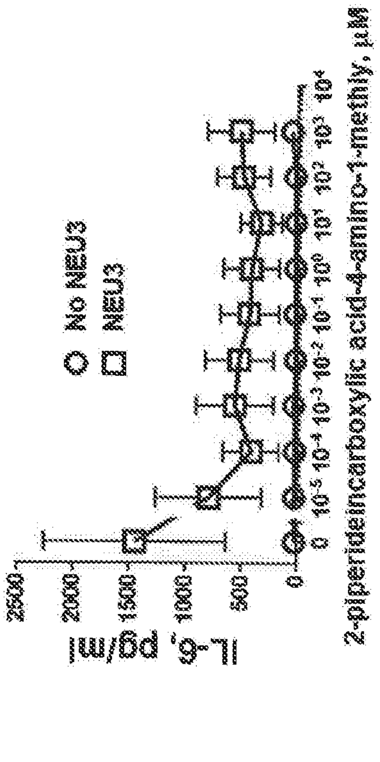
Figure 6A:
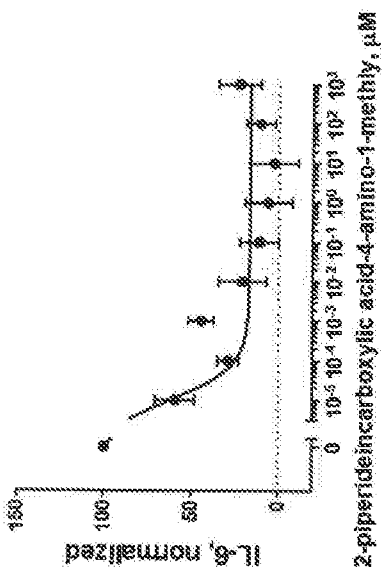
Figure 6A:
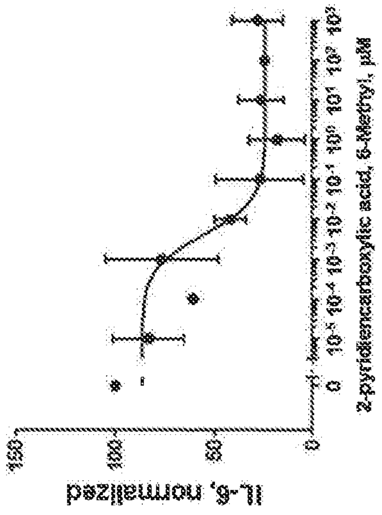
Figure 6A:
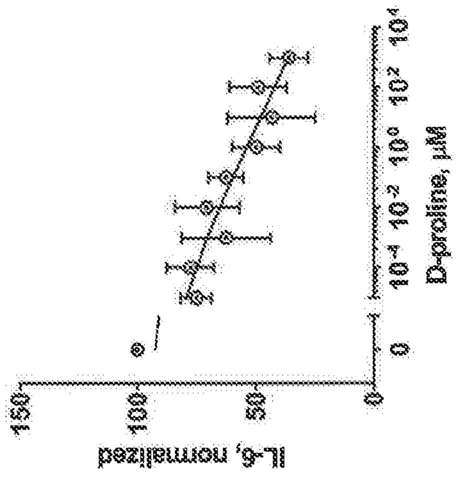
Figure 6A:
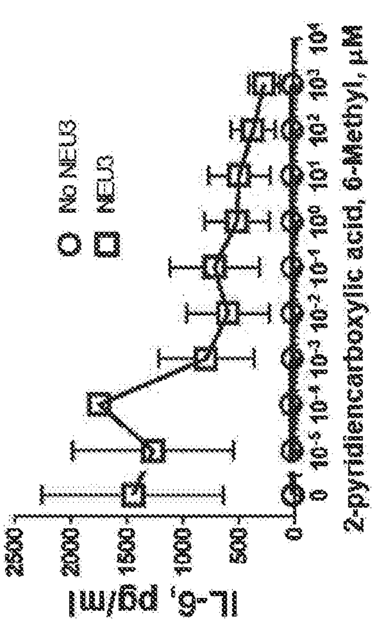
Figure 6A:
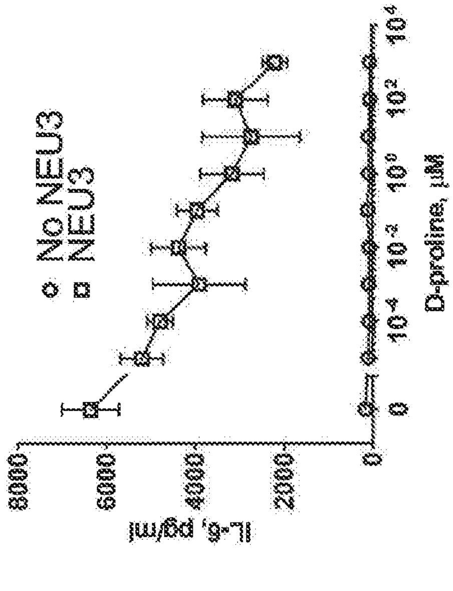
Figure 6A:
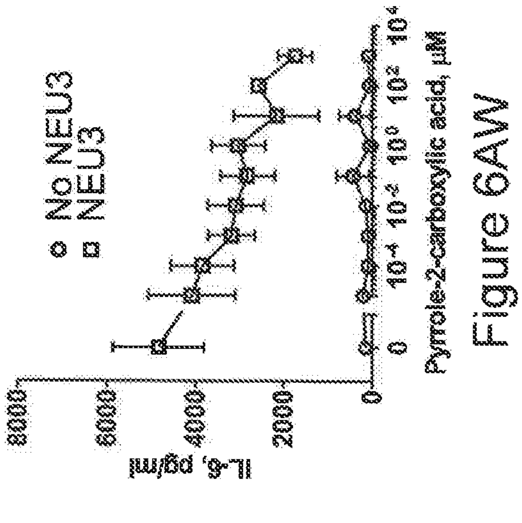
Figure 6A:
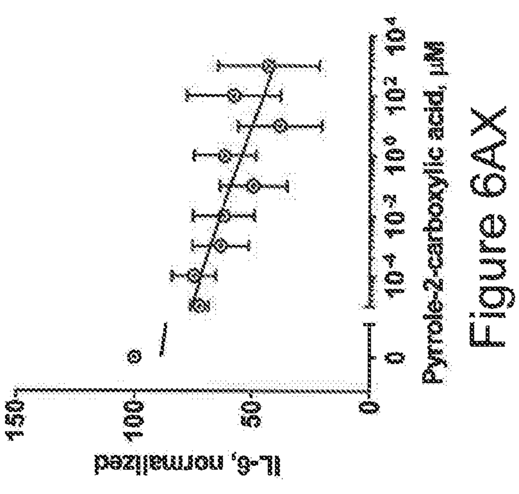
Figure 6A:
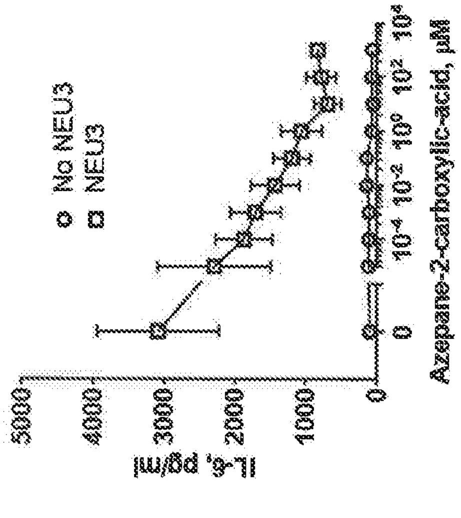
Figure 6A:
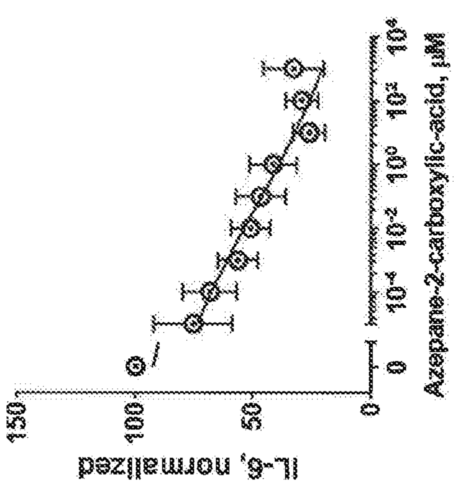

Results are presented in FIGS. 6A-AZ. The data show that NEU3 inhibitors reduced NEU3-induced extracellular IL-6 accumulation. Values are mean±SEM, n≥3.

Example 6

NEU3 Inhibitors Inhibit Mouse NEU3

To determine if selected NEU3 inhibitors could be used in mice to inhibit mouse NEU3, we made recombinant mouse NEU3 in HEK 293 Freestyle human embryonic kidney cells.

HEK 293 Freestyle cells (Life Technologies, Grand Island, NY) were cultured in FreeStyle 293 media (12338-018, Life Technologies, Grand Island, NY). $1\times10^5$ cells were mixed with 2 μg of 100 μg/ml of murine Neu3 expression clone (MR223297, Origene), in 100 μl PBS (GE Lifesciences), and were transfected by electroporation using a 4D-Nucelofactor System (Lonza) following the manufacturer's protocol. The transfected cells were kept at room temperature for 15 minutes for recovery, after which the cells were cultured in 25 ml Freestyle 293 media with 250 μg/ml of G418 antibiotic (345812, Calbiochem EMD Chemicals Inc. San Diego, CA) to select for transfected cells, in a 200 ml cell culture flask (431464U, Corning) at 37° C. humidified with 5% $CO_2$. After 10 days, the cells were isolated, lysed, and c-Myc tagged recombinant mouse NEU3 protein was purified using a Myc-Trap A kit (ytak-20, Chromotek, Hauppauge, NY) following the manufacturer's protocol. The eluted protein was stored in 50 μl of 10% glycerol, 100 mM glycine, 25 mM Tris-HCl pH 7.3.

To determine if NEU3 inhibitors would be effective in mice, NEU3 inhibitors were tested against recombinant mouse NEU3. Inhibitors were dissolved in 5 ml water to 20 mM in 15 ml tubes (89039-664, VWR, Radnor, PA). All stocks were stored at 4° C. and used within 2 weeks of preparation. A 10-fold dilution series of the compounds starting at 2 mM were made in PBS pH 6.9 in 1.7 ml clear microtubes (22-281, Genesee Scientific). 100 μl of diluted compound was added to the well of a 96 well plate and then 50 μl of 400 ng/ml recombinant mouse NEU3 in PBS pH 6.9 was added to each well (50 μl PBS pH 6.9 for the control), and the plate was incubated for 30 minutes at 37° C. 50 μl of 800 ng/ml L-TGF-β1 (299-LT/CF, R&D Systems) in PBS pH 6.9 was then added to the well. The plate was covered with aluminum foil and incubated for 2 hours at 37° C., and released active TGF-β1 was assayed as described above.

Figure 7B:
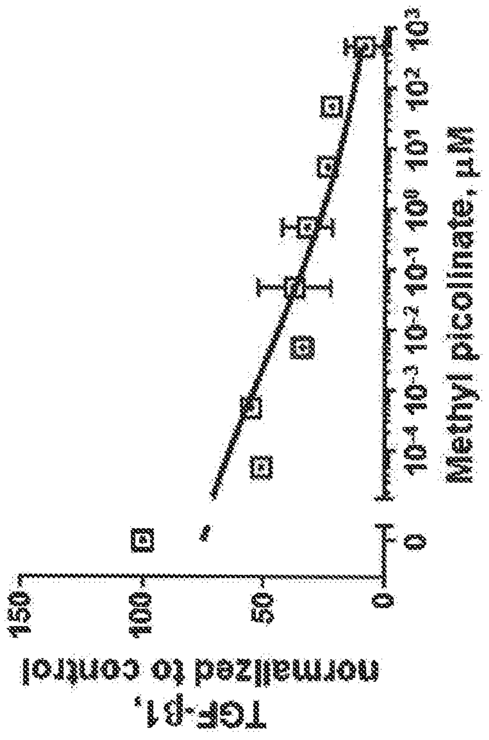
FIGS. 7A-7B are graphs quantifying the inhibition of recombinant mouse NEU3-catalyzed TGF-β1 activation as measured by a TGF-β1 ELISA kit by 2-acetyl pyridine (FIG. 7A) and methyl picolinate (FIG. 7B). Values are mean±SEM, n=3.
Figure 7A:
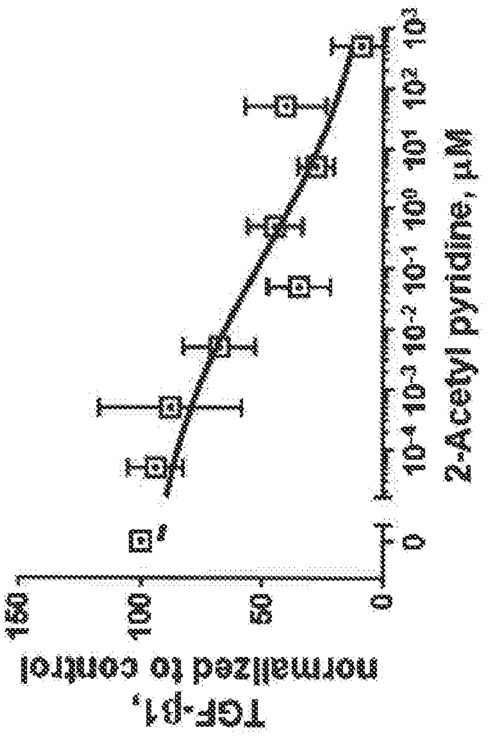

Results are presented in FIGS. 7A-B. Both 2-acetyl pyridine (FIG. 7A) and methyl picolinate (FIG. 7B) inhibited NEU3's activation of TGF-β1.

Example 7

NEU3 Inhibitors Reduce Bleomycin-Induced Pulmonary Fibrosis in Mice

To determine if selected compounds affect pulmonary fibrosis in mice, 8-10 week old 26-30 g male C57BL/6 mice (Jackson, Bar Harbor, ME) were given an oropharyngeal aspiration of 3 units/kg bleomycin (2246-10, 50, BioVision Incorporated, Milpitas, CA) in 50 μl of 0.9% saline to induce symptoms of pulmonary fibrosis or oropharyngeal saline as a control following *Current protocols in mouse biology* 2, 167-175, (2012). Starting 10 days after bleomycin had been administered, some of the bleomycin-treated mice were given daily intraperitoneal injections of 100 μl of PBS or 1 mg/kg 2-acetyl pyridine (sc-254121, Santa Cruz Biotechnology, Inc. Dallas, TX) or 1 mg/kg methyl picolinate (sc-228575, Santa Cruz Biotechnology, Inc.) or 0.1 mg/kg of 2-piperidinecarboxylic acid, 4-amino-1-methyl (A00285-13785-026, Sundia, Shanghai, China) in 100 μl PBS. At day 21, mice were sacrificed by $CO_2$ inhalation, and bronchoalveolar lavage (BAL) fluid and cytospins of BAL cells were obtained as previously described in *Current protocols in mouse biology* 2, 167-175 (2012); *Proceedings of the National Academy of Sciences of the United States of America* 112, 11929-11934 (2015); *Proceedings of the National Academy of Sciences of the United States of America* 111, 18291-18296 (2014); *Proceedings of the National Academy of Sciences of the United States of America* 112, 8385-8390 (2015); and *Public Library of Science ONE* 9, e93730 (2014) (all hereby incorporated by reference). The total cells from cytospins were quantified as described previously in *Current protocols in mouse biology* 2, 167-175, (2012); and *Public Library of Science ONE* 9, e93730 (2014). The lungs were removed and inflated with Surgipath frozen section compound (3801480, Leica, Buffalo Grove, IL) and preserved at −80° C. 6-10 μm cryosections of lungs were placed on glass slides (48311-703, VWR). The experiment was performed in accordance with the recommendations in the Guide for the Care and Use of Laboratory Animals of the National Institutes of Health. The Texas A&M University Animal Use and Care Committee approved the protocol.

Cryosections were stained for collagen with 0.1% Sirius red (09400, Polysciences, Warrington, PA), in saturated picric acid (26853-07, Electron Microscopy Sciences, Hatfield, PA) for 15 minutes at room temperature. The sections were washed in 0.5% acetic acid in water (v/v) for 10 minutes with two washes at room temperature. After dehydrating the sections in ethanol, the sections were mounted in Permount mounting medium (17986-01, Electron Microscopy Sciences). The sections were imaged on a Nikon Microphot-FX (Nikon, Tokyo, Japan), and staining was quantified with ImageJ.

Immunohistochemistry on BAL cytospins was performed as described previously in *Public Library of Science ONE* 9, e93730 (2014); *Proceedings of the National Academy of Sciences of the United States of America* 111, 18291-18296 (2014); and *Proceedings of the National Academy of Sciences of the United States of America* 112, 8385-8390 (2015) using anti-CD11b (101202, clone M1/70 BioLegend, San Diego, CA) to detect blood and inflammatory macrophages, anti-CD11c (M100-3, clone 223H7, MBL International, Woburn, MA) to detect alveolar macrophages and dendritic cells, anti-CD45 (103102, clone 30-F11, BioLegend) for total leukocytes, anti-Ly-6G (127602, clone 1A8, BioLegend) to detect neutrophils, and anti-Ly-6C (128001, clone HK1.4, BioLegend) to detect a variety of inflammatory immune system cells, and with isotype-matched irrelevant antibodies (BioLegend) as controls.

Figures 8A, 8B, 8C, 8D, 8E, 8F:
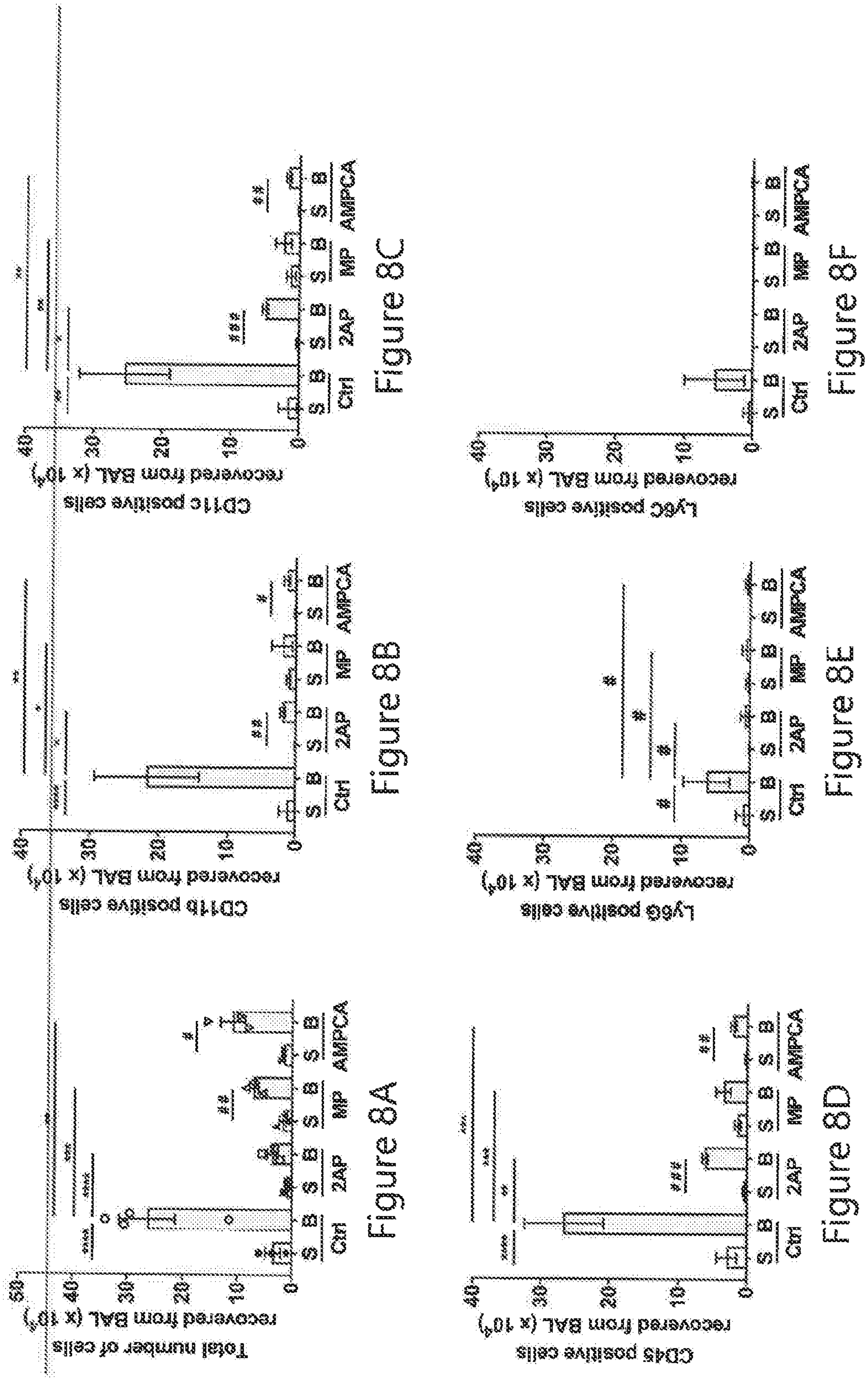
FIGS. 8A-8F are graphs quantifying the number of cells found in mouse bronchoalveolar lavage fluid after treatment with bleomycin.
Figure 9A:
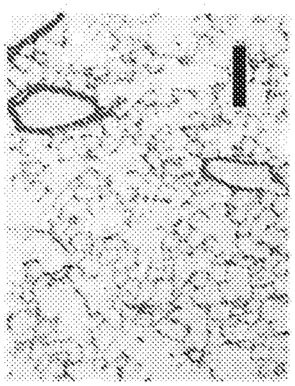
FIGS. 9A-9H are a set of photomicrographs of sections of mouse lungs from mice treated with saline, bleomycin, saline+2-acetylpyridine, bleomycin+2-acetyl pyridine, saline+methyl picolinate, bleomycin+methyl picolinate, saline+2-piperidinecarboxylic acid, 4-amino-1-methyl and bleomycin+2-piperidinecarboxylic acid, 4-amino-1-methyl, stained with Sirius red to show collagen.
Figure 9B:
Figure 9C:
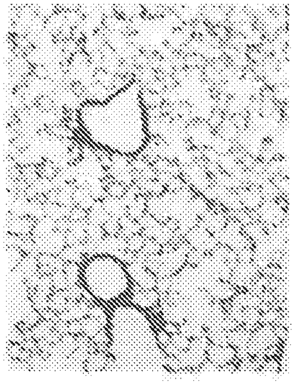
Figure 9D:
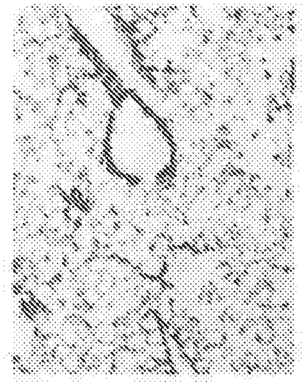
Figure 9E:
Figure 9F:
Figure 9G:
Figure 9H:
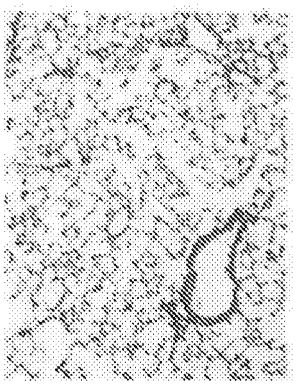

FIGS. 8A-F show that daily intraperitoneal injections of NEU3 inhibitors starting at day 10 decreased fibrosis in the mouse bleomycin model at day 21. FIG. 8A shows the total number of cells collected in bronchoalveolar lavage (BAL) from the mice with bleomycin-induced fibrosis as compared to those without fibrosis. NEU3 inhibitors reduced the number of cells collected from bleomycin-treated mice. FIG. 8B-F shows the total number of CD11b+, CD11c+, CD45, Ly6G, and Ly6C cells collected from the BAL. CD11b+ is a marker for inflammatory neutrophils and macrophages. CD11c+ is a marker for resident lung macrophages and dendritic cells. Together, these results indicate that 2-acetyl pyridine, methyl picolinate, and 2-piperidinecarboxylic acid-4-amino-1-methyl can reduce fibrosis-associated inflammation in a mouse model. Values are mean±SEM, n=3. *=p≤0.05, =p≤0.01, *=p≤0.001 (1-way ANOVA, Bonferroni's test), #=p≤0.05, ##=p≤0.01, ###=p≤0.001 (t-test).

Figure 10:
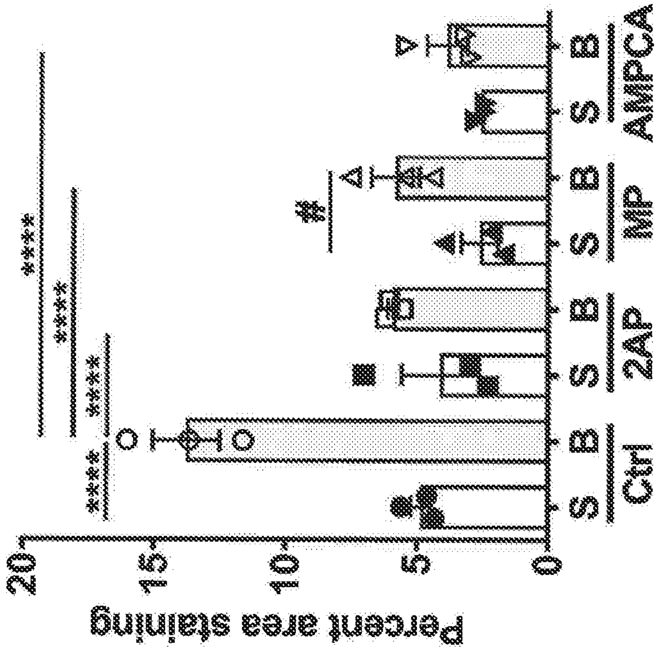
FIG. 10 is a graph quantifying the amount of stain in the photomicrographs of FIGS. 9A-H. Values are mean±SEM, n=3. ****=p≤0.0001 (1-way ANOVA, Bonferroni's test), #=p≤0.05 (t-test).
Figure 11:
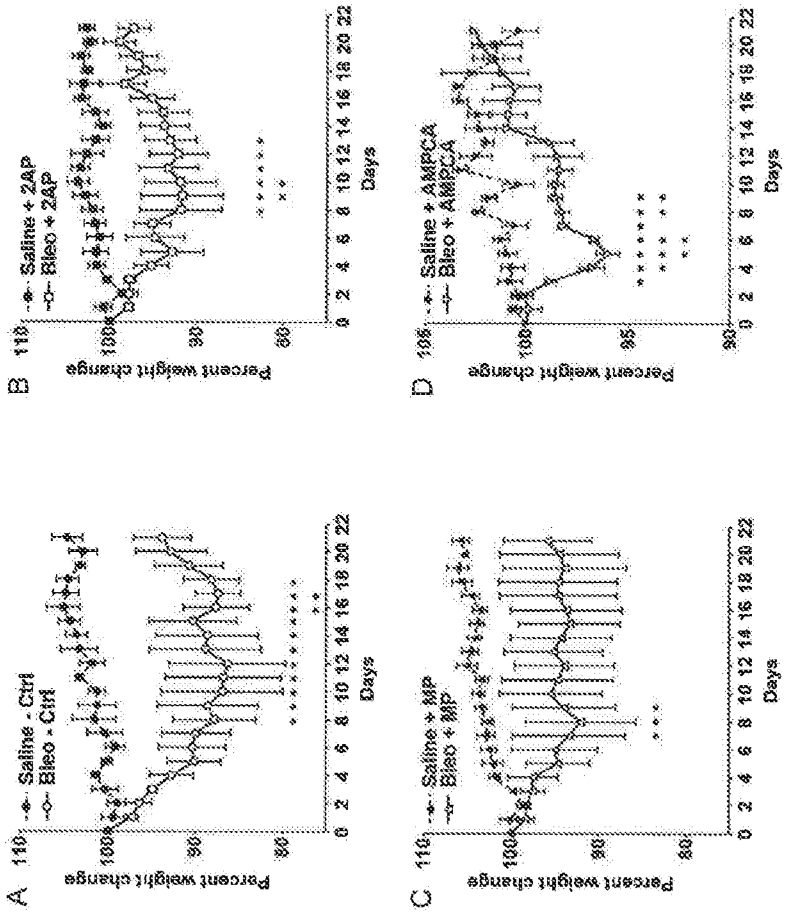
FIGS. 11A-D are graphs measuring the percent weight change over a period of 21 days of mice treated with saline, bleomycin (bleo), saline+2-acetylpyridine (2AP), bleomycin+2-acetyl pyridine, saline+methyl picolinate (MP), bleomycin+methyl picolinate, saline+2-piperidinecarboxylic acid, 4-amino-1-methyl and bleomycin+2-piperidinecarboxylic acid (AMPCA), 4-amino-1-methyl.

FIGS. 9A-H show eight sets of cryosections stained for collagen with Sirius red. FIG. 10 shows quantification of the Sirius red staining. Compared to saline control, bleomycin induced collagen deposition in the lungs (fibrosis), and this collagen deposition was reduced by treatment with 2-acetyl pyridine (2AP), methyl picolinate (MP), or 2-piperidinecarboxylic acid-4-amino-1-methyl (AMPCA), indicating that inhibiting NEU3 inhibits fibrosis.

FIGS. 11A-D shows percent weight change of mice. Compared to saline control, bleomycin induced decrease in weights of mice, and this decrease in weights was attenuated by treatment with 2-acetyl pyridine, methyl picolinate, or 2-piperidinecarboxylic acid-4-amino-1-methyl.

Example 8

Effect of High Fat Diet Induced Weight Change in Neu3 Knockout Mice

Having found that NEU3 inhibitors inhibit bleomycin-induced lung fibrosis and that bleomycin-induced lung inflammation and fibrosis is reduced in Neu3 knockout mice (Neu3 we wished to determine if Neu3 is involved in high-fat diet (HFD) induced liver inflammation, and if inhibiting one or more sialidases could inhibit high fat diet induced liver inflammation in mice.

12-16 week old male C57BL/6 (#000664; Jackson Laboratory, Farmington, CT) were fed standard rodent chow (15% kcal fat, Teklad 8604, Envigo, Madison WI) and obese C57BL/6 mice (#380050; Jackson) were fed a high fat diet (60% kcal fat, D12492 formula; Research Diets New Brunswick, NJ). 12 week old male C57BL/6 background Neu3 knockout mice ($Neu3^{-/-}$) strain B6.129-$Neu3^{tm1Yamk}$ (Yamaguchi, K., et al., *Reduced Susceptibility to Colitis-Associated Colon Carcinogenesis in Mice Lacking Plasma Membrane-Associated Sialidase*. PLoS ONE, 2012. 7(7): p. e41132) were also fed standard and HFD chow. Mice were placed on the specified diets for 4 weeks before the start of procedures. Mice were maintained on their specific diets for 5 weeks (35 days). Mice were weighed between 9:00 AM and noon. Animals were housed with a 12-hour/12-hour light-dark cycle (lights on at 7 AM) with free access to food and water. All procedures were performed between 09:00 and 11:00 AM. This protocol was done with specific approval of the Texas A&M University institutional animal care and use committee.

To determine if Neu3 is involved in high fat diet-induced liver macrophage accumulation, at day 35 of the experiment, following euthanasia, liver tissue was removed, and fixed in Zn-buffered formalin solution (0.1% $ZnSO_4$; 4% formaldehyde) for 2 days, then placed in 10% and then 30% sucrose solution in PBS for 2 days each (all compounds from VWR). Fixed tissues were then kept in 70% ethanol until paraffin processing and sectioning at 5 μm. Before antibody staining, fixed tissue sections were de-paraffinized with xylene, then rehydrated through a graded series of alcohols and distilled water. Sections were then incubated at 98° C. for 20 minutes in 10 mM sodium citrate (pH 6.0) to expose antigens. Sections were stained with 5 μg/ml antibodies against Mac2 (rat mAb, clone M3/38, BioLegend, San Diego, CA) to detect inflammatory and tissue macrophages, F4/80 (rabbit mAb, D2S9R, Cell Signaling Technology, Danvers, MA) to detect tissue resident macrophages, CD64 (rabbit mAb 50086-R001, SinoBiological, Wayne, PA) to detect RcγRI expression, and CLEC4F (goat Ab, AF2784, Novus Biologicals, Littleton, CO) to specifically detect Kupffer cells, as described in Pilling D, et al., *Serum Amyloid P and a Dendritic Cell-Specific Intercellular Adhesion Molecule-*3-*Grabbing Nonintegrin Ligand Inhibit High-Fat Diet-Induced Adipose Tissue and Liver Inflammation and Steatosis in Mice* Am J Pathol. 2019 December; 189(12):2400-2413.

Figure 12:
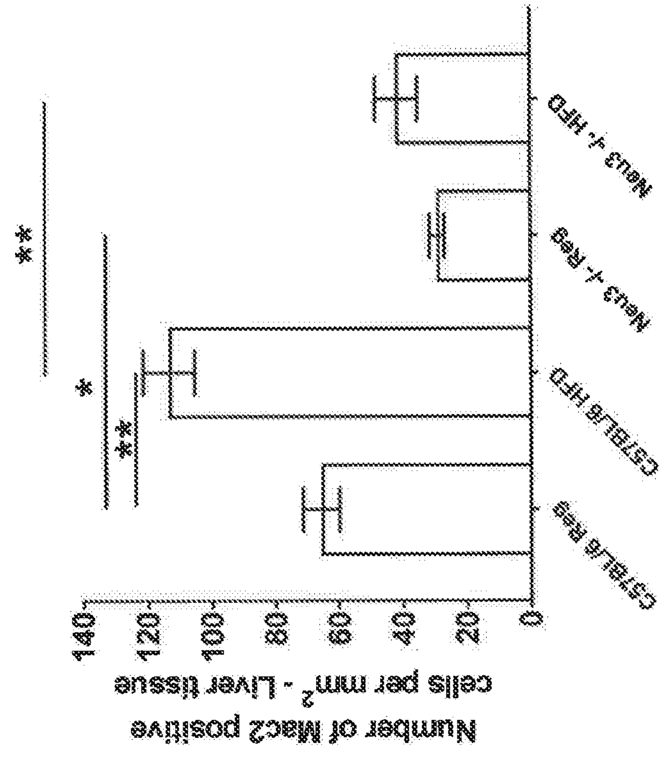
FIG. 12 is a graph quantifying the number of Mac2 positive cells per square millimeter of liver tissue in C57BL/6 and $Neu3^{-/-}$ mice on regular (control) or high fat diets (HFD). Liver sections were stained with Mac 2 antibodies to detect macrophages. Values are mean±SEM, n=3. * indicates p<0.05, **p<0.01 (1-way ANOVA, Dunnett's test).

Different types of liver macrophages can promote tissue regeneration or drive inflammation and fibrosis depending on signals present in the liver environment. Elevated levels of Mac2 (Galectin-3) present on macrophages are associated with liver inflammation and fibrosis. FIG. 12 shows that compared to C57BL/6 mice fed regular rodent chow, HFD C57BL/6 mice had significantly higher numbers of Mac2 positive cells in the liver. Compared to C57BL/6 mice, Neu3 mice fed regular chow had significantly lower Mac2 positive cells in the liver. There were also significantly lower numbers of Mac2 positive cells in the livers of HFD $Neu3^{-/-}$ mice compared to the livers of HFD C57BL/6 mice.

Figure 13A:
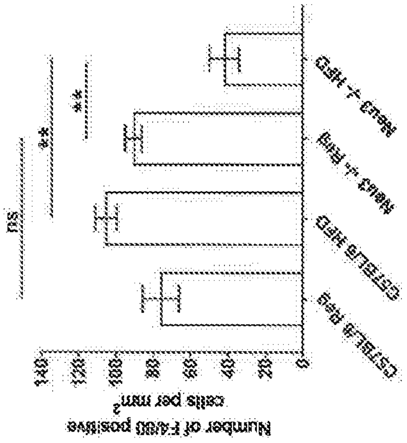
FIGS. 13A-C are graphs quantifying the number of cells per square millimeter of liver tissue in C57BL/6 and $Neu3^{-/-}$ mice on regular (control) or high fat diets (HFD) positive for: A) F4/80, B) CD64, and C) CLEC4f Values are mean±SEM, n=3. * indicates p<0.05, **p<0.01 (1-way ANOVA, Dunnett's test).
Figure 13B:
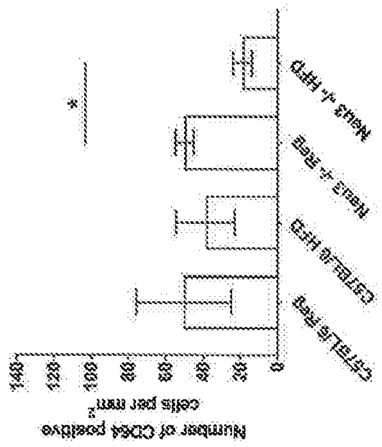
Figure 13C:
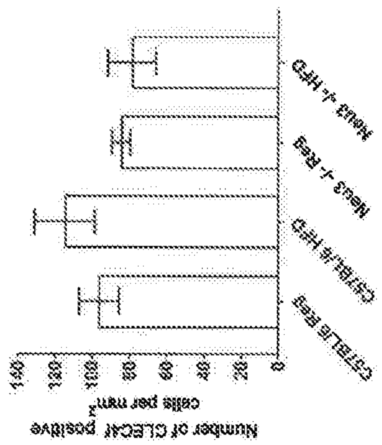

FIGS. 13A-C show that compared to HFD C57BL/6 mice, HFD $Neu3^{-/-}$ mice had significantly fewer F4/80 positive liver macrophages, but there was no difference in the number of Clec4f positive Kupffer cells. These data suggest that loss of Neu3 decreases HFD-induced liver inflammation.

Example 9

DANA Decreases HFD-Induced Lipid Accumulation in Liver 12 week old male C57BL/6 mice (#000664; Jackson Laboratory, Farmington, CT) were fed standard rodent chow (15% kcal fat, Teklad 8604, Envigo, Madison WI) and 12-16 week old male C57BL/6 mice (#380050; Jackson) were fed a high fat diet (60% kcal fat, D12492 formula; Research Diets New Brunswick, NJ). Mice were placed on the specified diets for 6 weeks before the start of treatment. To determine if the sialidase inhibitor DANA (#252926-10MG, Millipore-Sigma, Burlington, MA) decreases high-fat diet induced weight gain, mice were treated every 48 hours with intraperitoneal injections of phosphate-buffered saline (PBS) or DANA at 10 mg/kg in PBS, formulated as 4 mg/ml in PBS. Mice were maintained on their specific diets and received injections every 48 hours for 5 weeks (35 days). Animals were housed with a 12-hour/12-hour light-dark cycle (lights on at 7 AM) with free access to food and water. All injections were performed between 9:00 and 11:00 AM. This protocol was done with specific approval of the Texas A&M University institutional animal care and use committee.

To determine the amount of steatosis (accumulation of fat in the cells of the liver), frozen sections were prepared by placing freshly isolated pieces of liver in Surgipath frozen section compound, freezing on dry ice, and storing at −80° C. 10-12 μm cryosections of liver were placed on glass slides and were stained with oil red O to detect the accumulation of lipids as described in Mehlem, A., et al., *Imaging of neutral lipids by oil red O for analyzing the metabolic status in health and disease*, Nat. Protoc., 2013. 8(6): p. 1149-54.

Figure 14:
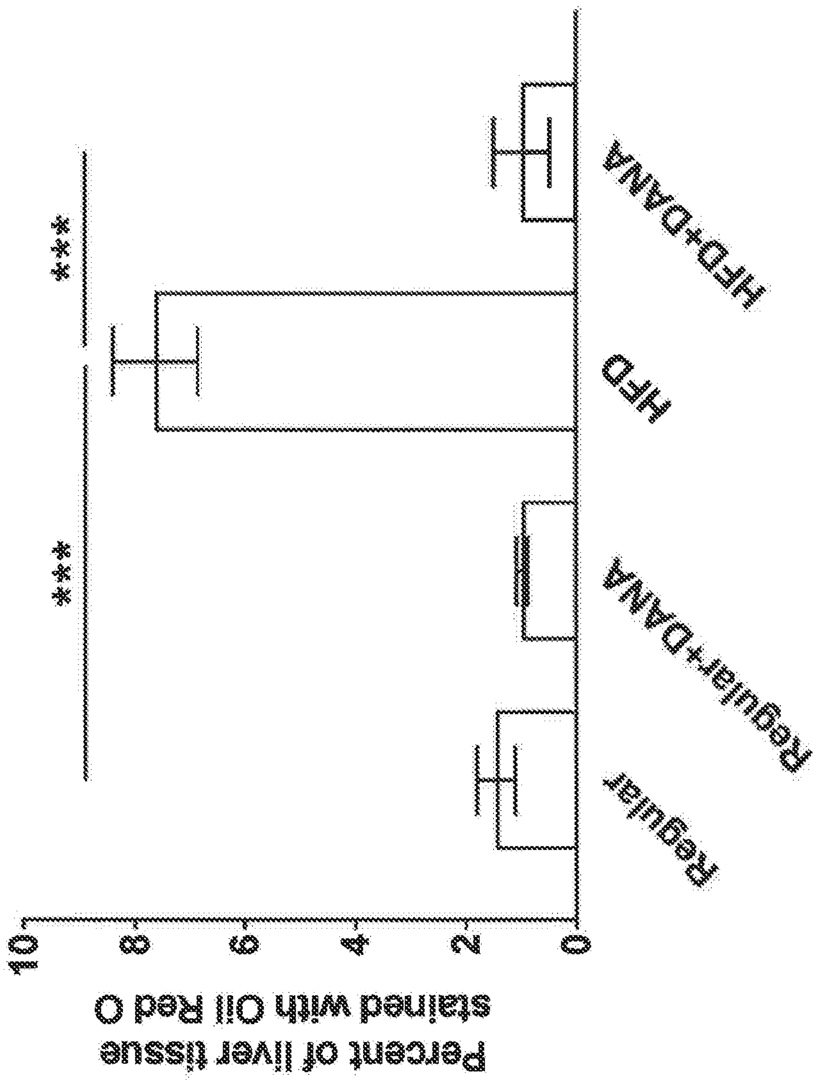
FIG. 14 is a graph quantifying the amount of fat in the livers of C57BL/6 mice on regular (control) or high fat diets (HFD) given either DANA or saline. Liver sections were stained with oil red O to detect neutral lipid accumulation. The percentage of area stained was quantified as a percentage of the total area of the liver. Values are mean±SEM, n=3. ***p<0.001 (1-way ANOVA, Dunnett's test).

FIG. 14 shows that compared to C57BL/6 mice fed regular rodent chow and treated with saline, HFD C57BL/6 mice treated with saline had significantly higher oil red O staining in the liver. Compared to HFD C57BL/6 mice treated with saline, HFD C57BL/6 mice treated with DANA had a significant reduction in oil red O staining. There was no significant difference in oil red O staining between C57BL/6 mice on regular diet treated with saline or DANA. These results indicate that DANA reduces HFD-induced neutral lipid accumulation in the liver.

Example 10

Figure 15:
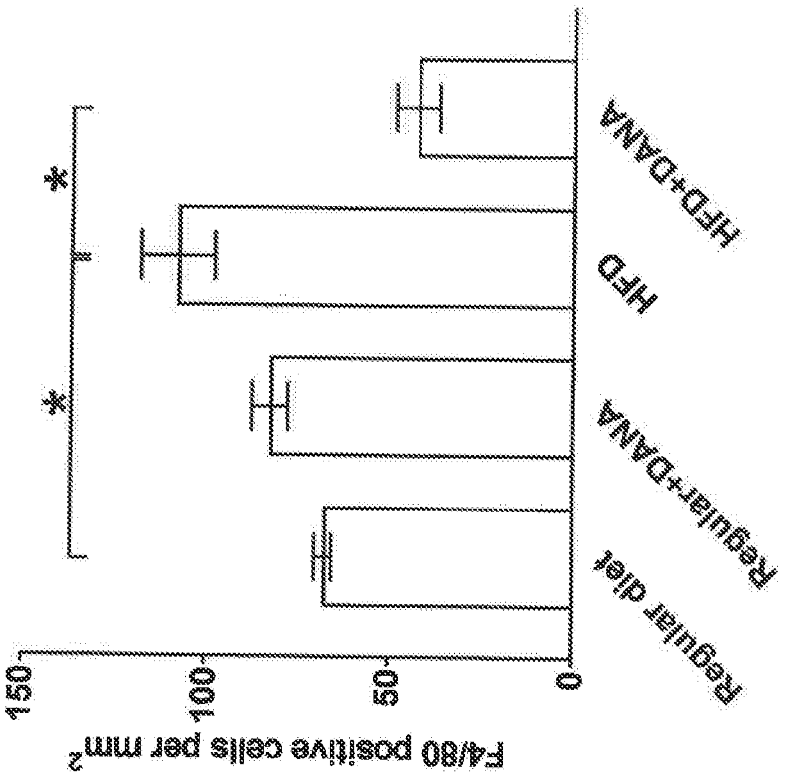
FIG. 15 is a graph quantifying the number of F4/80 positive cells per square millimeter of liver tissue in C57BL/6 mice on regular (control) or high fat diets (HFD) given either DANA or saline. Liver sections were stained with anti-F4/80 antibodies to detect macrophages. Values are mean±SEM, n=3. * indicates p<0.05 (1-way ANOVA, Dunnett's test).

DANA Decreases HFD-Induced Tissue Resident F4/80 Positive Macrophages in the Liver As in Example 9, mice were maintained on their specific diets and received injections of buffer or DANA every 48 hours for 5 weeks (35 days). Following euthanasia, liver tissue was removed, fixed, and then sectioned as described above. FIG. 15 shows that compared to C57BL/6 mice fed regular rodent chow and treated with saline, HFD C57BL/6 mice treated with saline had significantly higher numbers of F4/80 positive liver resident macrophages. HFD mice treated with DANA had a significant reduction in F4/80 positive cells compared to HFD mice treated with saline. There was no significant difference in F4/80 staining between C57BL/6 mice on a regular diet treated with saline or DANA. These results indicate that DANA reduces the HFD-induced increase in the number of F4/80 positive macrophages in the liver.

Example 11

Effect of DANA Injections on Mouse Weight

Figure 16:
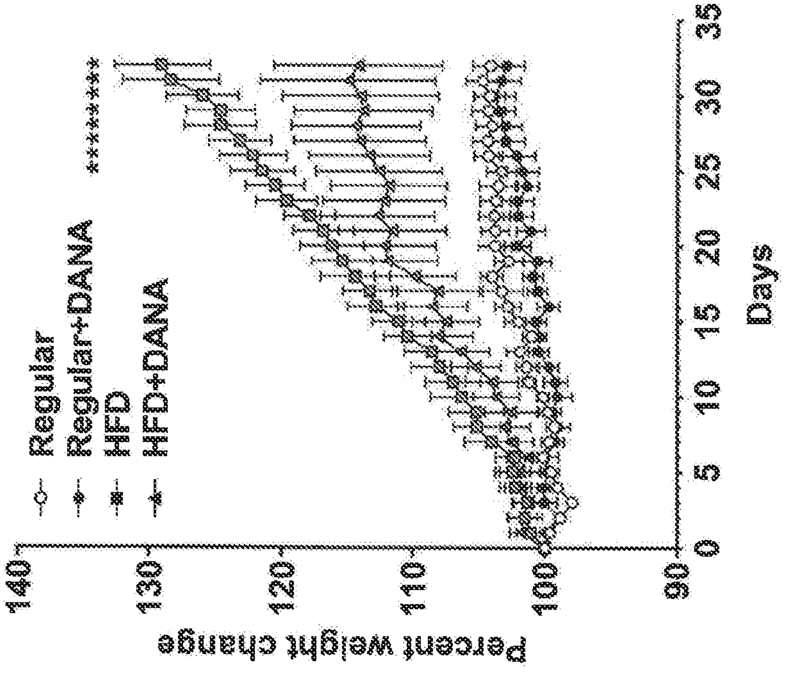
FIG. 16 is a graph quantifying the weight change of C57BL/6 mice on regular (control) or high fat diets (HFD) given either DANA or saline. Mice received injections of PBS or DANA every 48 hours for 35 days. Mice were weighed daily. Values are mean±SEM, n=6 mice per group. * indicates p<0.05 comparing HFD with HFD+DANA, at each time point (t-test).

FIG. 16 shows that intraperitoneal injections of DANA as described in Example 9 reduce high fat diet induced weight gain. Control mice fed regular chow and treated with either PBS or DANA injections had no significant differences in weight. In the mice fed the high fat diet (HFD), compared to the PBS injected mice, there was a significant reduction in weight gain observed in mice treated with DANA injections after 21 days of treatment. The results presented in FIG. 16 indicate that sialidase inhibitors such as DANA may improve the ability to regulate weight in diet-induced obesity.

Example 12

Effect of DANA Injections on Mouse Glucose Levels

Obesity is associated with type 2 diabetes, a condition where the cells of the body do not efficiently respond to insulin, a process called insulin resistance. This situation leads to elevated levels of glucose in the blood system, and following an increase in blood glucose (such as after a meal or an injection of glucose), the body takes longer than normal to reduce blood glucose levels. To determine if DANA could reduce blood glucose levels, on day 33 of the experiment described in Example 15, mice were fasted for 16 hours starting at 5 PM. On day 34, mice received an IP injection of 1.5 g/kg glucose (Amresco, Solon, OH) formulated as 525 mg/ml in PBS. Blood glucose levels were measured before glucose administration (0 minutes), and at 20, 40, 60, 90, and 120 minutes after the injection using commercial blood glucose test strips (CVS Pharmacy, Woonsocket, RI).

Figure 17:
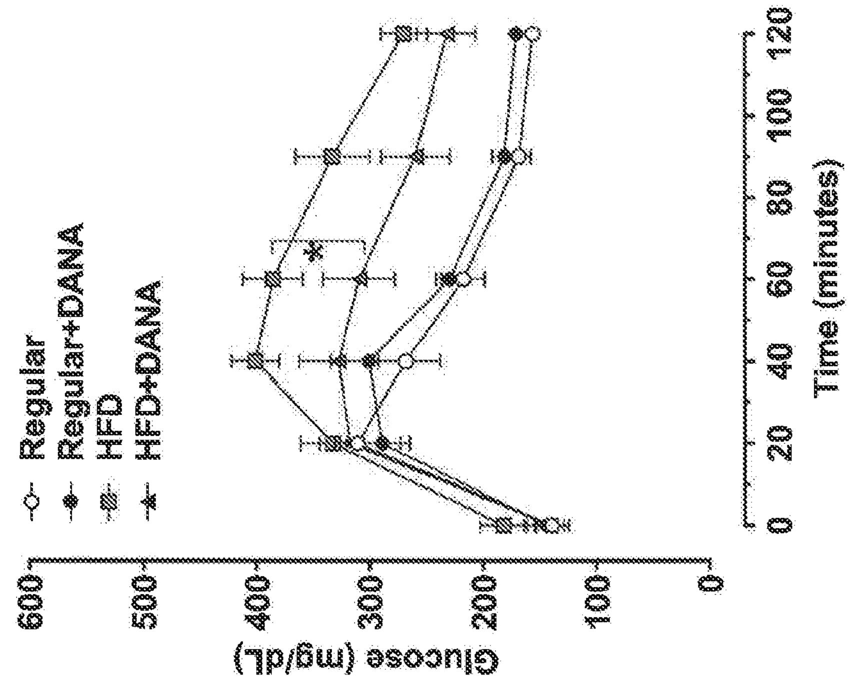
FIG. 17 is a graph quantifying the glucose levels of C57BL/6 mice on regular (control) or high fat diets (HFD) given either DANA or saline. Values are mean±SEM, n=5-6. * indicates p<0.05 comparing HFD and HFD+DANA (t test).

FIG. 17 shows that control mice fed standard rodent chow and treated with either DANA or PBS injections had no significant differences in fasting glucose levels (t=0 minutes) or glucose levels after the glucose injection. However, HFD fed mice injected with DANA had significantly lower blood glucose levels at 60 minutes compared to control HFD mice.

Figure 18:
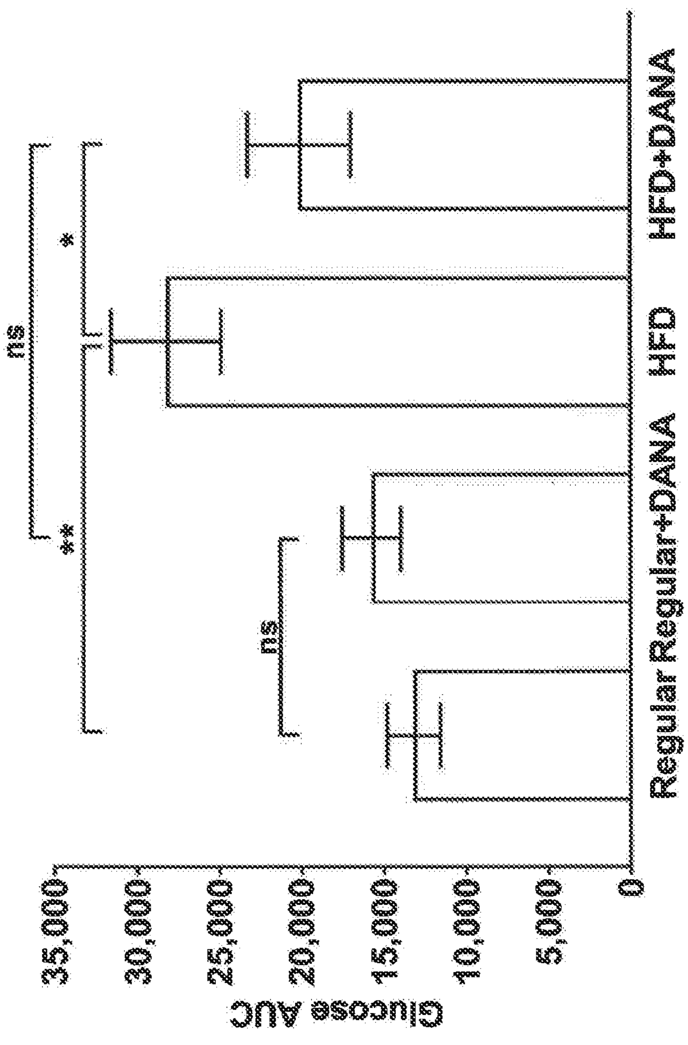
FIG. 18 is a graph quantifying glucose tolerance of C57BL/6 mice over 120 minutes as assessed by area under the curve (AUC) analysis of FIG. 17. Values are mean±SEM, n=5-6. "ns" indicates not significant. * indicates p<0.05, **p<0.01 (1-way ANOVA, Dunnett's test).

FIG. 18 shows HFD mice treated with DANA had significantly lower total glucose levels compared to the HFD control group. The results presented in FIGS. 17 and 18 indicate that DANA injections may improve the ability to regulate glucose levels in obesity.

Example 13

Effect of DANA Injections on Mouse Organ Weights

Obesity is associated with increased size (weight) of many organs, including white fat and liver. To determine if the sialidase inhibitor DANA could prevent a high fat diet-induced increase in organ weights, at day 35 of the experiment described in Example 9, following euthanasia, organs including epididymal white adipose and inter-scapular brown adipose tissue, liver, spleen, lungs, and kidneys were weighed.

Figure 19:
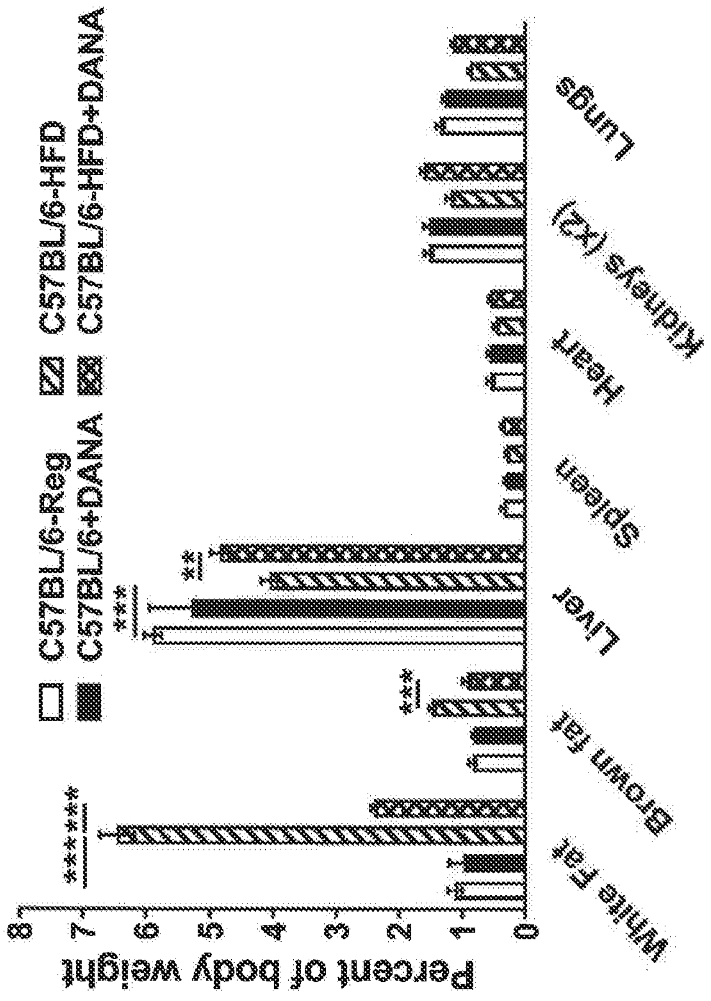
FIG. 19 is a graph quantifying organ weights of C57BL/6 mice on regular (control) or high fat diets (HFD) given either DANA or saline. Following euthanasia, organs including epididymal white and inter scapular brown adipose tissue, liver, spleen, lungs, and kidneys were weighed. Values are percent of body weight for each mouse. Values are mean±SEM, n=3. p<0.01, * p<0.001 comparing HFD and HFD+DANA (1-way ANOVA, Holm-Sidak test).

FIG. 19 shows that control mice fed regular rodent chow and treated with either DANA or PBS injections had no significant differences in any organ weights. As a percentage of body weight, control HFD mice had significantly higher white and brown adipose tissue weights compared to mice on regular chow. HFD mice treated with DANA injections had significantly lower white fat and brown fat weights compared to control HFD mice.

The above disclosed subject matter is to be considered illustrative, and not restrictive, and the appended claims are intended to cover all such modifications, enhancements, and other embodiments which fall within the true spirit and scope of the present disclosure. For example, although the disclosure focuses on inhibiting human sialidases, the sialidase inhibitors disclosed may be effective against other mammalian sialidases, particularly those with a protein sequence or structure similar to human sialidase. Efficacy of sialidase inhibitors against other mammalian sialidases may be readily determined using the methods set forth in this disclosure. In addition, methods of affecting fibrocytes, fibrosis, inflammation, steatosis, obesity, and cancer using such sialidase inhibitors may be adapted from this disclosure.

The invention claimed is:

1. A method of treatment of a fibrotic disorder, the method comprising administering a pharmaceutical formulation comprising a compound of formula (I)

I

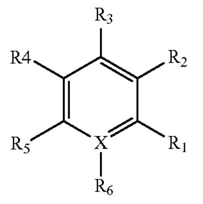

or its salt, wherein:

$R_1$ is selected from $CONH_2$, $COCH_3$, and $C_{1-6}$alkyl ester;

$R_2$, $R_3$, $R_4$, and $R_5$ are hydrogen; and

X is nitrogen.

2. The method of claim 1, wherein an activity of human NEU3 in desialylating LAP is inhibited.

3. The method of claim 1, wherein an activity of human NEU3 in desialylating SAP is inhibited.

4. The method of claim 2, wherein formation or activation of fibrocytes is inhibited.

5. The method of claim 3, wherein formation or activation of fibrocytes is inhibited.

6. The method of claim 1, wherein the compound is methyl picolinate.

7. The method of claim 1, wherein the compound is 2-acetyl pyridine.

8. The method of claim 1, further comprising administering the formulation in an amount and for a time sufficient to decrease a level or activity of TGF-β1 in a human.

9. The method of claim 1, further comprising administering the formulation in an amount and for a time sufficient to decrease a level or activity of a sialidase in a human.

10. The method of claim 1, wherein the compound is picolinamide.

11. A method of treatment of a fibrotic disorder, the method comprising:

administering a pharmaceutical formulation comprising a compound of formula (I)

I

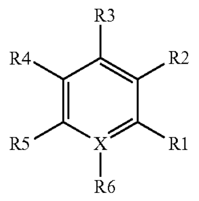

or its salt, wherein:

$R_1$ is selected from COOH, $CONH_2$, $COCH_3$, and $C_{1-6}$alkyl ester;

$R_2$, $R_3$, $R_4$, and $R_5$ are hydrogen; and

X is nitrogen; and administering the formulation in an amount and for a time sufficient to decrease a level or activity of a sialidase in a human.

* * * * *